United States Patent
Bauer et al.

(10) Patent No.: US 11,666,757 B2
(45) Date of Patent: *Jun. 6, 2023

(54) SYSTEMS, DEVICES, AND METHODS FOR IMPROVING HEMODYNAMIC PERFORMANCE THROUGH ASYMPTOMATIC DIAPHRAGM STIMULATION

(71) Applicant: VisCardia, Inc., Beaverton, OR (US)

(72) Inventors: Peter T. Bauer, Portland, OR (US); Edward Chinchoy, Studio City, CA (US); Jay Snell, Los Angeles, CA (US)

(73) Assignee: VisCardia, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/477,432

(22) Filed: Sep. 16, 2021

(65) Prior Publication Data

US 2022/0001174 A1    Jan. 6, 2022

Related U.S. Application Data

(63) Continuation of application No. 16/399,896, filed on Apr. 30, 2019, now Pat. No. 11,147,968, which is a
(Continued)

(51) Int. Cl.
*A61N 1/36* (2006.01)
*A61N 1/362* (2006.01)
(Continued)

(52) U.S. Cl.
CPC ............ *A61N 1/3601* (2013.01); *A61B 5/024* (2013.01); *A61B 5/113* (2013.01); *A61B 5/287* (2021.01);
(Continued)

(58) Field of Classification Search
CPC ................ A61N 1/3601; A61N 1/3627; A61N 1/36585; A61B 5/024; A61B 5/113;
(Continued)

(56) References Cited

U.S. PATENT DOCUMENTS

| 4,411,268 A | 10/1983 | Cox |
|---|---|---|
| 5,098,442 A | 3/1992 | Grandjean |

(Continued)

FOREIGN PATENT DOCUMENTS

| CA | 1256507 A1 | 6/1989 |
|---|---|---|
| EP | 1588735 A1 | 10/2005 |

(Continued)

OTHER PUBLICATIONS

Roos, Markus, et al; Improved cardiac performance through pacing-induced diaphragmatic stimulation: a novel electrophysiological approach in heart failure management? European Society of Cardiology. Clinical Research. Pacing and Cardiac Resynchronization Therapy. Europace (2009) 11, 191-199. Lucerne, Switzerland (Dec. 8, 2008).

(Continued)

*Primary Examiner* — Mallika D Fairchild
(74) *Attorney, Agent, or Firm* — Loza & Loza, LLP; David S. Sarisky

(57) ABSTRACT

Hemodynamic performance of a heart may be improved by determining, from a location associated with a diaphragm, an occurrence of a valid cardiac event; and then delivering asymptomatic electrical stimulation therapy directly to the diaphragm at termination of a diaphragmatic stimulation delay period that is timed relative to the occurrence of the valid cardiac event. The diaphragmatic stimulation delay period may be automatically established by sensing a plurality of cardiac events directly from a diaphragm; and for each of the sensed cardia events, determining whether the (Continued)

sensed cardiac event represents a valid cardiac event or a non-valid cardiac event. The diaphragmatic stimulation delay period is then calculated based on a plurality of sensed cardia events that are determined to be valid.

16 Claims, 21 Drawing Sheets

Related U.S. Application Data continuation of application No. 15/288,130, filed on Oct. 7, 2016, now Pat. No. 10,335,592, which is a continuation-in-part of application No. 14/107,976, filed on Dec. 16, 2013, now Pat. No. 9,498,625.

(60) Provisional application No. 61/739,704, filed on Dec. 19, 2012.

(51) Int. Cl.
  *A61B 5/024* (2006.01)
  *A61B 5/113* (2006.01)
  *A61B 5/00* (2006.01)
  *A61N 1/365* (2006.01)
  *A61B 5/287* (2021.01)
  *A61B 5/349* (2021.01)

(52) U.S. Cl.
  CPC ............ *A61B 5/349* (2021.01); *A61B 5/4836* (2013.01); *A61B 5/686* (2013.01); *A61B 5/6867* (2013.01); *A61B 5/721* (2013.01); *A61N 1/3627* (2013.01); *A61N 1/36585* (2013.01); *A61B 2562/063* (2013.01)

(58) Field of Classification Search
  CPC ..... A61B 5/4836; A61B 5/686; A61B 5/6867; A61B 5/721; A61B 5/3627; A61B 5/36585; A61B 2562/063
  See application file for complete search history.

(56) References Cited

U.S. PATENT DOCUMENTS

| | | | |
|---|---|---|---|
| 5,188,098 A | | 2/1993 | Hoffman et al. |
| 5,300,094 A | | 4/1994 | Kallok et al. |
| 5,358,519 A | | 10/1994 | Grandjean |
| 5,397,280 A | | 3/1995 | Skurka |
| 5,632,716 A | | 5/1997 | Bui et al. |
| 5,693,000 A | | 12/1997 | Crosby et al. |
| 5,758,654 A | | 6/1998 | Burton-Krahn et al. |
| 5,814,086 A * | | 9/1998 | Hirschberg ........... A61N 1/3601 607/42 |
| 6,415,183 B1 | | 7/2002 | Scheiner et al. |
| 6,979,297 B2 | | 12/2005 | Andresen et al. |
| 7,039,538 B2 | | 5/2006 | Baker, Jr. |
| 7,072,708 B1 | | 7/2006 | Andresen et al. |
| 7,074,195 B2 | | 7/2006 | Nelson et al. |
| 7,096,060 B2 | | 8/2006 | Arand et al. |
| 7,096,064 B2 | | 8/2006 | Deno et al. |
| 7,113,820 B2 | | 9/2006 | Schlegel et al. |
| 7,171,269 B1 | | 1/2007 | Addison et al. |
| 7,174,203 B2 | | 2/2007 | Arand et al. |
| 7,225,021 B1 | | 5/2007 | Park et al. |
| 7,248,923 B2 | | 7/2007 | Maile et al. |
| 7,277,757 B2 | | 10/2007 | Casavant et al. |
| 7,302,290 B2 | | 11/2007 | Bauer |
| 7,357,775 B1 | | 4/2008 | Koh |
| 7,424,321 B2 | | 9/2008 | Wariar et al. |
| 7,435,221 B1 | | 10/2008 | Bharmi et al. |
| 7,437,699 B2 | | 10/2008 | Morita et al. |
| 7,467,012 B1 * | | 12/2008 | Park ..................... A61B 5/0809 600/483 |
| 7,559,903 B2 | | 7/2009 | Moussavi et al. |
| 7,668,589 B2 | | 2/2010 | Bauer |
| 7,725,181 B1 | | 5/2010 | Bomzin et al. |
| 7,819,814 B2 | | 10/2010 | Gavriely et al. |
| 7,979,128 B2 | | 7/2011 | Tehrani et al. |
| 7,994,655 B2 | | 8/2011 | Bauer et al. |
| 8,065,002 B2 | | 11/2011 | Arand et al. |
| 8,105,241 B2 | | 1/2012 | Nelson et al. |
| 8,137,283 B2 | | 3/2012 | Syeda-Mahmood et al. |
| 8,140,164 B2 | | 3/2012 | Tehrani et al. |
| 8,185,190 B2 | | 5/2012 | Bauer |
| 8,200,336 B2 | | 6/2012 | Tehrani et al. |
| 8,233,987 B2 | | 7/2012 | Gelfand et al. |
| 8,244,358 B2 | | 8/2012 | Tehrani et al. |
| 8,244,359 B2 | | 8/2012 | Gelfand et al. |
| 8,265,759 B2 | | 9/2012 | Tehrani et al. |
| 8,348,852 B2 | | 1/2013 | Bauer et al. |
| 8,409,108 B2 | | 4/2013 | Bauer et al. |
| 8,412,323 B2 | | 4/2013 | Bauer |
| 8,433,412 B1 | | 4/2013 | Westlund et al. |
| 8,548,588 B1 | | 10/2013 | Bauer |
| 8,577,448 B2 | | 11/2013 | Bauer et al. |
| 8,706,236 B2 | | 4/2014 | Ignagni et al. |
| 8,909,341 B2 | | 12/2014 | Gelfand et al. |
| 2002/0103521 A1 | | 8/2002 | Swoyer et al. |
| 2002/0188329 A1 | | 12/2002 | Struble |
| 2003/0187337 A1 | | 10/2003 | Tarassenko et al. |
| 2003/0195571 A1 | | 10/2003 | Burnes et al. |
| 2004/0088015 A1 | | 5/2004 | Casavant et al. |
| 2004/0127792 A1 | | 7/2004 | Siejko et al. |
| 2004/0230105 A1 | | 11/2004 | Geva et al. |
| 2005/0027323 A1 | | 2/2005 | Mulligan et al. |
| 2005/0043644 A1 | | 2/2005 | Stahmann et al. |
| 2005/0065563 A1 | | 3/2005 | Scheiner |
| 2005/0080348 A1 | | 4/2005 | Stahmann et al. |
| 2005/0085865 A1 | | 4/2005 | Tehrani |
| 2005/0085869 A1 | | 4/2005 | Tehrani et al. |
| 2005/0090870 A1 | | 4/2005 | Hine et al. |
| 2005/0222515 A1 | | 10/2005 | Polyshchuk et al. |
| 2006/0079942 A1 | | 4/2006 | Deno et al. |
| 2006/0122661 A1 | | 6/2006 | Mandell |
| 2006/0122662 A1 | | 6/2006 | Tehrani et al. |
| 2006/0155202 A1 | | 7/2006 | Arand et al. |
| 2007/0021795 A1 | | 1/2007 | Tehrani |
| 2007/0038137 A1 | | 2/2007 | Arand et al. |
| 2007/0055151 A1 | | 3/2007 | Shertukde et al. |
| 2007/0191725 A1 | | 8/2007 | Nelson |
| 2008/0021510 A1 | | 1/2008 | Mi et al. |
| 2008/0125820 A1 | | 5/2008 | Stahmann et al. |
| 2008/0167695 A1 | | 7/2008 | Tehrani et al. |
| 2008/0177191 A1 | | 7/2008 | Patangay et al. |
| 2008/0188904 A1 | | 8/2008 | Tehrani et al. |
| 2008/0215106 A1 | | 9/2008 | Lee et al. |
| 2008/0255465 A1 | | 10/2008 | Nelson |
| 2008/0287820 A1 | | 11/2008 | Ignagni et al. |
| 2008/0288010 A1 | | 11/2008 | Tehrani et al. |
| 2008/0288015 A1 * | | 11/2008 | Tehrani ................ A61N 1/3601 607/42 |
| 2009/0024176 A1 | | 1/2009 | Yun et al. |
| 2009/0048640 A1 | | 2/2009 | Bauer et al. |
| 2009/0112107 A1 | | 4/2009 | Nelson et al. |
| 2009/0112108 A1 | | 4/2009 | Nelson et al. |
| 2009/0122108 A1 | | 5/2009 | Yoshida et al. |
| 2009/0165559 A1 | | 7/2009 | Lec |
| 2009/0192561 A1 | | 7/2009 | Bauer |
| 2010/0094148 A1 | | 4/2010 | Bauer et al. |
| 2010/0094376 A1 | | 4/2010 | Penner |
| 2010/0331903 A1 | | 12/2010 | Zhang et al. |
| 2011/0015702 A1 | | 1/2011 | Ternes et al. |
| 2011/0230932 A1 | | 9/2011 | Tehrani et al. |
| 2011/0288609 A1 | | 11/2011 | Tehrani et al. |
| 2012/0103521 A1 | | 5/2012 | Cheng |
| 2012/0296388 A1 | | 11/2012 | Zhang et al. |
| 2013/0030488 A1 * | | 1/2013 | Cho ..................... A61N 1/36521 607/42 |
| 2013/0030498 A1 | | 1/2013 | Karamanoglu et al. |
| 2013/0289636 A1 | | 10/2013 | Karmanoglu et al. |
| 2013/0296973 A1 | | 11/2013 | Tehrani et al. |

(56) References Cited

U.S. PATENT DOCUMENTS

| | | | |
|---|---|---|---|
| 2014/0114371 A1 | 4/2014 | Westlund et al. | |
| 2014/0172040 A1 | 6/2014 | Bauer | |
| 2017/0143973 A1 | 5/2017 | Fehrani | |

FOREIGN PATENT DOCUMENTS

| | | | |
|---|---|---|---|
| JP | 2010537716 A | 12/2010 | |
| WO | 2009029172 A1 | 3/2009 | |
| WO | 2016033245 A1 | 3/2016 | |

OTHER PUBLICATIONS

Zuber, Michel, et al; Detection and Hemodynamic Significance of Cardiac Pacemaker-Induced Phrenic Nerve Stimulation. Department of Cardiology, Kantonsspital, Luzern, Switzerland. 2010 Wiley Periodicals, Inc. Lucerne, Switzerland (Aug. 13, 2009).
PCT Patent Application No. PCT/US2013/075489. International Preliminary Report on Patentability (dated Jul. 2, 2015).
Matuschak, et al. "Hemodynamic effects of synchronous high-frequency jet ventilation during acute hypovolemia." J Appl Physiol. 61(1): 44-53 (Jul. 1986).
Pinsky, et al. "Hemodynamic effects of cardiac cycle-specific increases in intrathoracic pressure." J Appl Physiol. 60(2):604-12 (Feb. 1986).
Pinsky, et al. "Augmentation of cardiac function by elevation of intrathoracic pressure." J Appl Physiol. 54(4):950-55 (Apr. 1983).
Pinsky, et al., "Determinants of cardiac augmentation by elevations in intrathoracic pressure." J Appl Physiol. 58(4):1189-98 (May 1985).
PCT/US2017/029905. International Search Report & Written Opinion (dated Aug. 8, 2017).
PCT/US2017/029939 International Search Report & Written Opinion (dated Aug. 10, 2017).
PCT/US2017/029924. International Search Report & Written Opinion (dated Oct. 2, 2017).
PCT/US2017/051021. International Search Report & Written Opinion (dated Dec. 12, 2017).
PCT/US2017/029924. Written Opinion of the International Preliminary Examining Authority (dated Apr. 6, 2018).
PCT/US2017/029939. Written Opinion of the International Preliminary Examining Authority (dated Apr. 6, 2018).
Beeler et al. "Improvement of cardiac function with device-based diaphragmatic stimulation in chronic heart failure patients: the randomized, open-label, crossover Epiphrenic II Pilot Trial." European Journal of Heart Failure (2014) 16. pp. 342-349. European Society of Cardiology.
PCT/US2017/051021. International Preliminary Reporton Patentability (dated Jan. 3, 2019).
PCT/US2017/029924. International Preliminary Reporton Patentability (dated Aug. 10, 2018).
PCT/US2017/029939. International Preliminary Reporton Patentability (dated Oct. 12, 2018).
PCT/US2017/029905. International Preliminary Report on Patentability (dated Aug. 22, 2018).
PCT/US2013/075489. International Search Report & Written Opinion (dated Mar. 11, 2014).
EP Application No. 13865191.4. Office Action (dated Sep. 29, 2017).
JP Application No. 2015-549544. Office Action (dated Sep. 21, 2017).
Pang et al. Monitoring respiratory activity in neonates using diaphragmatic electromyograph. Medical and Biological Engineering and Computing, vol. 33, 385-390 (1995).
PCT/US2017/029924. International Search Report & Written Opinion (dated Apr. 6, 2018).
PCT/US2017/051021. Written Opinion. (dated Aug. 24, 2018).

* cited by examiner

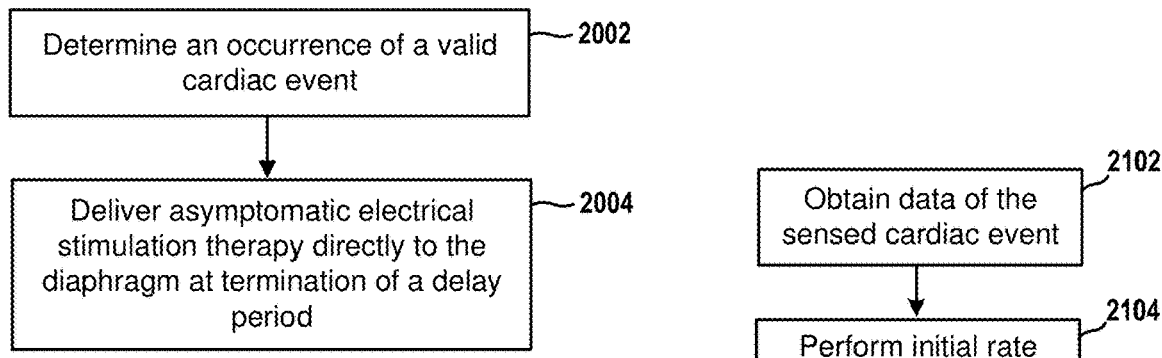
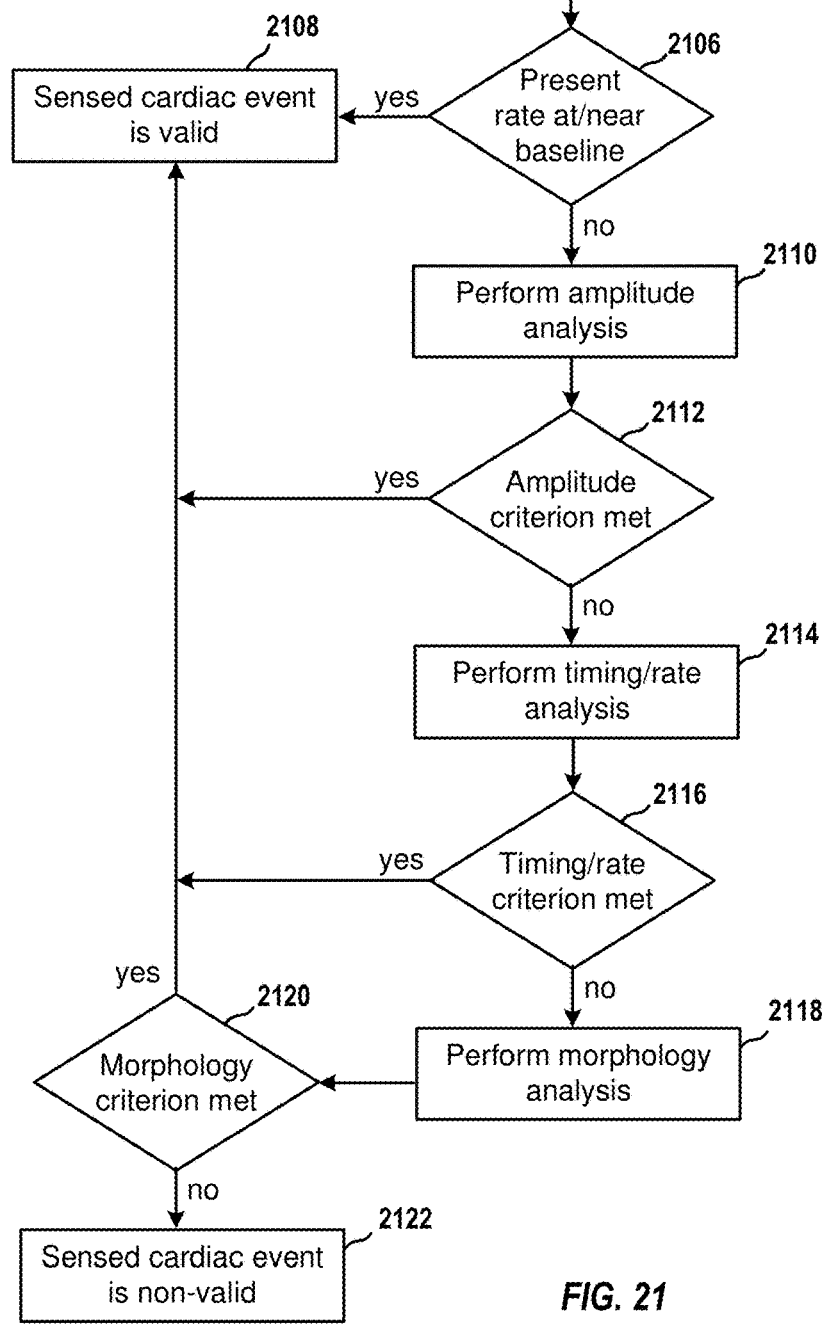
FIG. 20
FIG. 21

SYSTEMS, DEVICES, AND METHODS FOR IMPROVING HEMODYNAMIC PERFORMANCE THROUGH ASYMPTOMATIC DIAPHRAGM STIMULATION

CROSS-REFERENCE TO RELATED APPLICATIONS

This application is a continuation of U.S. patent application Ser. No. 16/399,896, filed Apr. 30, 2019, for Systems, Devices, and Methods for Improving Hemodynamic Performance Through Asymptomatic Diaphragm Stimulation," now U.S. Pat. No. 11,147,968, which is a continuation of U.S. patent application Ser. No. 15/288,130, filed Oct. 7, 2016, for "Systems, Devices, and Methods for Improving Hemodynamic Performance Through Asymptomatic Diaphragm Stimulation," now U.S. Pat. No. 10,335,592, which is a continuation-in-part of U.S. patent application Ser. No. 14/107,976, filed Dec. 16, 2013, for "Hemodynamic Performance Enhancement Through Asymptomatic Diaphragm Stimulation," now U.S. Pat. No. 9,498,625, which claims the benefit of and priority to U.S. Provisional Patent Application Ser. No. 61/739,704, filed Dec. 19, 2012, for "Hemodynamic Performance Enhancement Through Asymptomatic Diaphragm Stimulation to the Diaphragm/Heart Interface", the entire disclosures of which are incorporated herein by reference.

BACKGROUND

Patients with severe congestive heart failure can become refractory to standard medical therapy. A number of device-based therapies have been developed to improve hemodynamic performance due to reduced cardiac function and reduce patient symptoms, e.g., systolic function, in such patients. One of the most prominent examples is cardiac resynchronization therapy (CRT), which has proven to be an effective technique for decreasing morbidity and mortality and increasing quality of life in patients with severe and moderate heart failure and mechanical dyssynchrony. Implantation of a cardiac rhythm management (CRM) device, e.g., a biventricular (BiV) pacemaker, in such patients leads to a more synchronous contraction pattern of the right ventricle (RV), left ventricle (LV) and left atrium (LA). Assuming good placement of the ventricular pacing leads and optimized pacemaker settings, there is acute improvement in systolic performance resulting in chronic reverse remodeling of the heart.

Implantation of a CRM device, however, is an invasive procedure requiring placement of electrode-bearing leads either directly within the heart or on the surface of the heart. Furthermore, although CRT has been proven to effectively improve systolic function, electrical stimulation of the heart through endocardial leads can also cause unwanted stimulation of skeletal muscle. The left phrenic nerve, which provides innervation for the diaphragm, arises from the cervical spine and descends to the diaphragm through the mediastinum where the heart is situated. As the left phrenic nerve passes the heart, it courses along the pericardium, superficial to the left atrium and LV. When in close in proximity to pacing leads, the nerve can be stimulated by a pacing pulse, leading to involuntary contractions of the diaphragm. Phrenic nerve stimulation has been reported in as many as 24% of patients with implanted CRT devices and can also occur in patients with regular pacemakers. The induced diaphragmatic contraction is mostly symptomatic, so it will either be felt by the patient or is easy to palpate during physical examination.

Improved systolic function may be achieved by other devices and methods, depending on the underlying root cause for the severe systolic dysfunction and the benefit offered in treating specific root causes. Examples of other devices and methods include LV assist devices for patients with severely failing hearts awaiting heart transplantation, cardiac contractility modulation, and implantable counter pulsation therapy for patients with very low systolic strength and no dyssynchrony. Some of these devices and methods, such as IN assist devices, are as or more highly invasive than CRT devices requiring placement directly on or around the heart, or in the case of LV assist devices, transection through the cardiac walls or vessels to directly interface with the circulating blood pool.

In view of the foregoing, it would be beneficial to have a device and methodology of improving hemodynamic performance in heart failure patients to augment mechanical cardiac threes without increasing demands on cardiac musculature already suffering from reduced function. In cases where a CRM device, e.g., pacemaker or defibrillator, is already implanted in a patient, it would be beneficial to have a separate implantable device configured to operate in conjunction with the CRM device to improve hemodynamic performance.

SUMMARY OF THE INVENTION

Methods, apparatuses, and systems for improving hemodynamic performance of a heart are disclosed. In one embodiment of such methods, apparatuses, and systems, an occurrence of a valid cardiac event is determined from a location associated with a diaphragm. The location associated with the diaphragm may be a location in direct contact with the diaphragm, or a location adjacent the diaphragm, but not necessarily in direct contact with the diaphragm. Upon an occurrence of a valid cardiac event, asymptomatic electrical stimulation therapy is delivered directly to the diaphragm at termination of a delay period that is timed relative to the occurrence of the valid cardiac event. In this sense, asymptomatic electrical stimulation therapy is triggered by the occurrence of the valid cardiac event.

To implement the foregoing, an implantable medical system may include one or more electrical stimulation therapy elements, e.g., electrodes, configured for placement on or near a diaphragm, and at least one electrical circuit structure coupled to the one or more electrical stimulation therapy elements. The electrical circuit structure is configured to determine an occurrence of a valid cardiac event, and deliver or output asymptomatic electrical stimulation therapy directly to the diaphragm at termination of a delay period. To this end, the electrical circuit structure may be configured to receive signals corresponding to a cardiac event and may include a computer processor having one or more software modules configured to process the signal to determine if the cardiac event is a valid cardiac event. Alternatively, the electrical circuit structure may be configured to receive a signal from another implanted device, e.g., a cardiac rhythm management device, indicating an occurrence of a valid cardiac event.

In one embodiment, asymptomatic electrical stimulation therapy may be triggered by atrial cardiac events, in which case the delay period is based on a time between an occurrence of an atrial event and an occurrence of a following ventricular event. In one such configuration, the delay period is based on a time between an occurrence of an intrinsic atrial event and an occurrence of a following intrinsic ventricular event. An occurrence of a valid cardiac event may be determined by detecting a valid intrinsic atrial event at the location associated with the diaphragm. Alternatively, an occurrence of a valid cardiac event may be determined by receiving, at the location associated with the diaphragm, a signal from an implanted cardiac rhythm management device, which signal indicates that a valid intrinsic atrial event has been detected by the implanted cardiac rhythm management device.

In another configuration of atrial-event triggered diaphragmatic stimulation, the delay period is based on a time between an occurrence of an atrial pacing stimulus and an occurrence of a following intrinsic ventricular event. In this case, an occurrence of a valid cardiac event may be determined by detecting an atrial pacing stimulus at the location associated with the diaphragm. Alternatively, an occurrence of a valid cardiac event may be determined by receiving, at the location associated with the diaphragm, a signal from an implanted cardiac rhythm management device, which signal indicates that an atrial pacing stimulus has been delivered by the implanted cardiac rhythm management device.

In yet another configuration of atrial-event triggered diaphragmatic stimulation, the delay period is based on a time between an occurrence of an evoked atrial event and an occurrence of a following intrinsic ventricular event. In this case, an occurrence of a valid cardiac event may be determined by detecting an evoked atrial event at the location associated with the diaphragm. Alternatively, an occurrence of a valid cardiac event may be determined by receiving, at the location associated with the diaphragm, a signal from an implanted cardiac rhythm management device, which signal indicates that an evoked atrial event has been sensed by the implanted cardiac rhythm management device.

In another embodiment, asymptomatic electrical stimulation therapy may be triggered by ventricular cardiac events, in which case the delay period is based on a time between an occurrence of a type of ventricular event and an occurrence of a following ventricular event of the same type. In one configuration, the delay period is based on a time between an occurrence of an intrinsic ventricular event of a first type and an occurrence of a following intrinsic ventricular event of the first type. In this case, an occurrence of a valid cardiac event may be determined by detecting a valid intrinsic ventricular event at the location associated with the diaphragm. Alternatively, a valid cardiac event may be determined by receiving, at the location associated with the diaphragm, a signal from an implanted cardiac rhythm management device, which signal indicates that a valid intrinsic ventricular event has been detected by the implanted cardiac rhythm management device.

In another one configuration of ventricular-event triggered asymptomatic electrical stimulation, the delay period is based on a time between an occurrence of a ventricular pacing stimulus and an occurrence of a following ventricular pacing stimulus. In this case, an occurrence of a valid cardiac event may be determined by detecting a ventricular pacing stimulus at the location associated with the diaphragm. Alternatively, an occurrence of a valid cardiac event may be determined by receiving, at the location associated with the diaphragm, a signal from an implanted cardiac rhythm management device, which signal indicates that a ventricular pacing stimulus has been delivered by the implanted cardiac rhythm management device.

In yet another configuration of ventricular-event triggered asymptomatic electrical stimulation, the delay period is based on a time between an occurrence of an evoked ventricular event and an occurrence of a following evoked ventricular event. In this case, an occurrence of a valid cardiac event may be determined by detecting an evoked ventricular event at the location associated with the diaphragm. Alternatively, an occurrence of a valid cardiac event may be determined by receiving, at the location associated with the diaphragm, a signal from an implanted cardiac rhythm management device, which signal indicates that an evoked ventricular event has been sensed by the implanted cardiac rhythm management device In another embodiment of methods, apparatuses, and systems for improving hemodynamic performance of a heart, the delay period at which diaphragmatic stimulation is delivered is automatically adjusted. To this end, a plurality of cardiac events is sensed directly from a diaphragm, and for each of the sensed cardia events, it is determined whether the sensed cardiac event represents a valid cardiac event or a non-valid cardiac event. A diaphragmatic stimulation delay period is then established based on a plurality of sensed cardia events that are determined to be valid. Asymptomatic electrical stimulation therapy is then delivered directly to the diaphragm based on the established diaphragmatic stimulation delay period.

To implement the foregoing, an implantable medical device may include one or more sensors configured to sense a plurality of cardiac events directly from a diaphragm. The implantable medical device may further include at least one electrical circuit structure configured to determine whether a sensed cardiac event represents a valid cardiac event or a non-valid cardiac event, to establish a diaphragmatic stimulation delay period, and to deliver asymptomatic electrical stimulation therapy directly to the diaphragm. To this end, the electrical circuit structure may be coupled to the one or more sensors to receive signals corresponding to the plurality of sensed cardiac event, and to one or more stimulators, e.g., electrodes, through which the electrode structure delivers asymptomatic electrical stimulation therapy. The electrical circuit structure may further include a computer processor having one or more software modules configured to process the received signals to determine if the cardiac event is a valid cardiac event or a non-valid cardiac event, and one or more software modules configured to establish a diaphragmatic stimulation delay period, and stimulation circuitry configured to output asymptomatic electrical stimulation pulses under control of the processor.

In one configuration, whether a sensed cardiac event represents a valid cardiac event or a non-valid cardiac event is determined by comparing a present characteristic, e.g., amplitude, interval, etc. of a waveform of the sensed cardiac event to a baseline characteristic of a waveform of a valid cardiac event. A non-valid cardiac event is determined when the comparison outcome between the present characteristic and the baseline characteristic fails to satisfy a criterion. In another configuration, whether a sensed cardiac event represents a valid cardiac event or a non-valid cardiac event is determined by comparing a present timing between the sensed cardiac event and a prior sensed cardiac event to a baseline timing between successive baseline valid cardiac events. A non-valid cardiac event is determined when a comparison outcome between the present timing and the baseline timing fails to satisfy a criterion.

A diaphragmatic stimulation delay period may be established by determining a plurality of measures of time, wherein each of the plurality of measures of time corresponds to a measure of time between a pair of successive sensed cardia events that are determined to be valid. The measures of time may be, for example, the time or interval between successive valid ventricular events. In one configuration, the pair of successive sensed cardia events that are determined to be valid may be either of: 1) a valid atrial event followed by a valid ventricular event, or 2) a first valid ventricular event of a first type followed by a second valid ventricular event of the first type. A statistical value is then determined based on the determined plurality of measures of time, and the diaphragmatic stimulation delay period is set based on the statistical value. Depending on the type of diaphragmatic stimulation intended, the diaphragmatic stimulation delay period is set to a value less than the statistical value or greater than the statistical value. For example, to provide early diaphragmatic stimulation, the stimulation delay period is set to a value less than the statistical value, whereas to provide late diaphragmatic stimulation, the stimulation delay period is set to a value greater than the statistical value to provide.

Once established, the diaphragmatic stimulation delay period may be automatically adjusted to account for changes in hemodynamic demand. To this end, a subsequent statistical value is determined based on a plurality of subsequently determined measures of time. Again, each of the plurality of subsequent measures of time corresponds to a measure of time between a pair of successive sensed cardia events that are determined to be valid. The subsequent statistical value is compared to the statistical value upon which the diaphragmatic stimulation delay period is based, and the diaphragmatic stimulation delay period is either maintained at its current setting or adjusted to a different setting based on the comparison outcome. For example, the diaphragmatic stimulation delay period may be maintained when the comparison outcome indicates there is no difference or no significant difference between the subsequent statistical value and the statistical value upon which the diaphragmatic stimulation delay period is based. The diaphragmatic stimulation delay period may be decreased as a function of the comparison outcome when the comparison outcome indicates the subsequent statistical value is less than the statistical value upon which the diaphragmatic stimulation delay period is based. Lastly, the diaphragmatic stimulation delay period may be increased as a function of the comparison outcome when the comparison outcome indicates the subsequent statistical value is greater than the statistical value upon which the diaphragmatic stimulation delay period is based.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIG. 7A pictures a condition of asymptomatic-stimulation-produced caudal diaphragmatic motion, and FIG. 7B a condition of related, immediate-time-following, cranial diaphragmatic motion. The statements just made, which draw relationships between conditions pictured in FIGS. 7A, 7B, with respect to FIGS. 6A, 6B, respectively, are equally applicable to relationships that exist between FIGS. 7A, 7B, and FIGS. 9A, 9B, 9C, and 9D described below.

In FIGS. 6A, 6B, 9A, 9B, 9C, and 9D, the exposed anatomical contents are greatly simplified in order to avoid unnecessary complexity without compromising disclosure, and in this context, lower portions of the left-side phrenic nerve structure have been removed to clearly show the positioning of the implanted device.

Figure 6A:
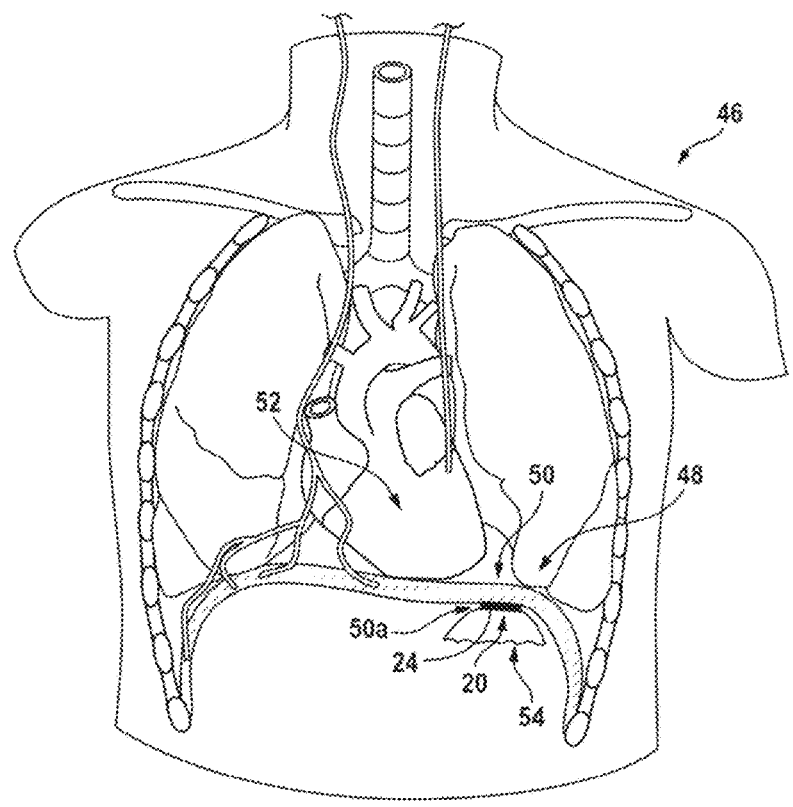
FIG. 6A is a frontal view of an internal portion of a subject's anatomy illustrating a proposed implant location for the first embodiment of the PIDS device shown in FIGS. 1-4.
Figure 6B:
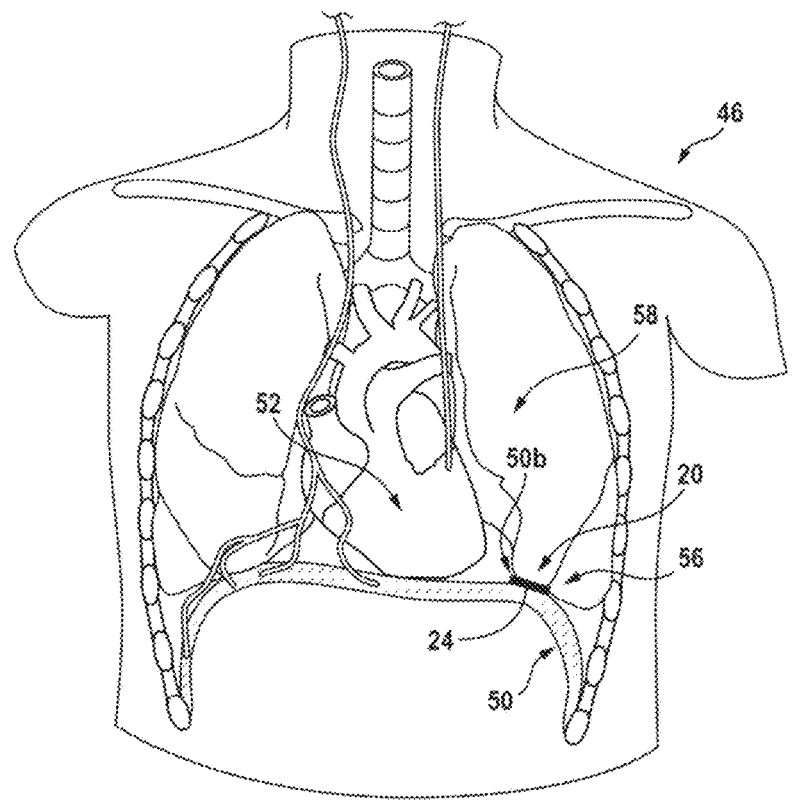
FIG. 6B is similar to FIG. 6A, except that it shows an alternative implant location for the first embodiment of the PIDS device shown in FIGS. 1-4.
Figure 7A:
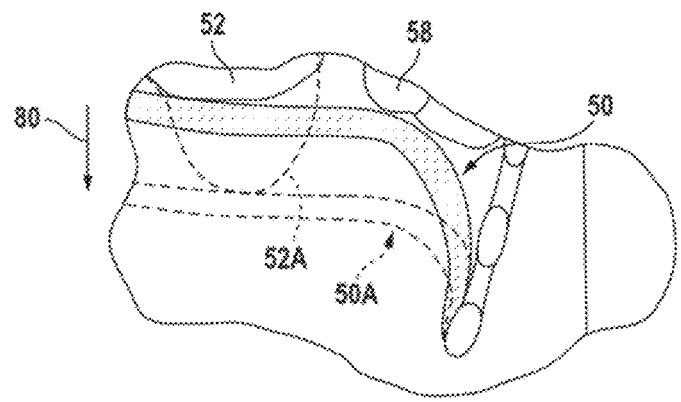
FIGS. 7A, 7B present enlarged-scale, fragmentary portions of the anatomical structure shown in FIGS. 6A, 6B (with the PIDS device of FIGS. 1-4 not shown for clarity) illustrating biphasic mechanical movement of the heart resulting from electrical stimulation, and resulting mechanical motion, of the diaphragm and heart.
Figure 7B:
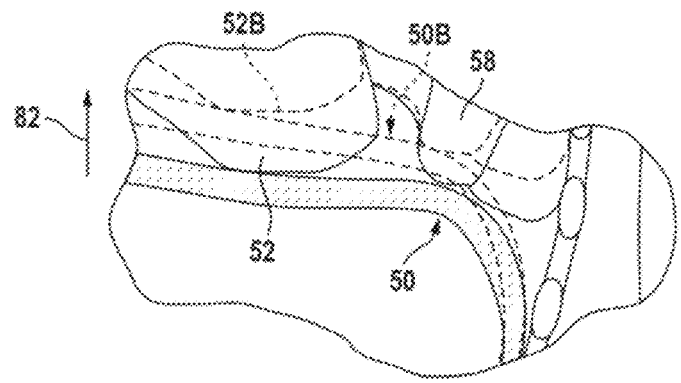

The various structural and anatomical elements shown in FIGS. 1-7B and in FIGS. 9A-9D, and the several moved anatomical positions, and changed anatomical configurations, pictured in FIGS. 7A and 7B, are not necessarily drawn to scale.

Figure 10A:
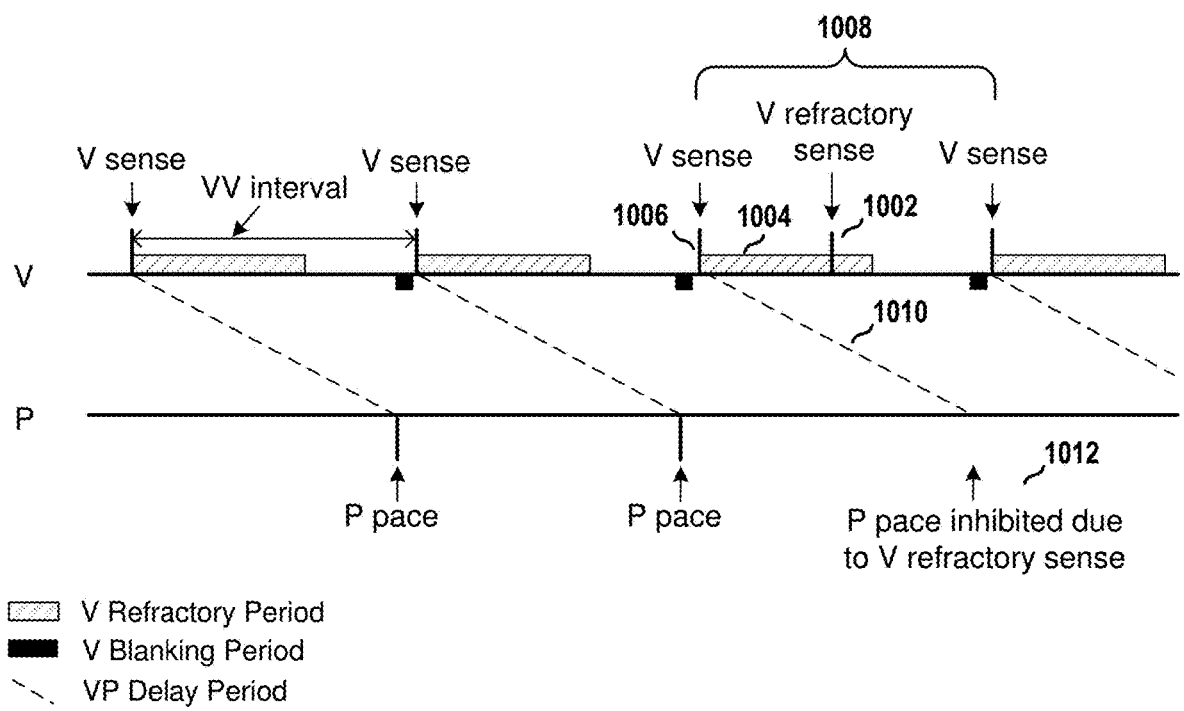
Figure 10B:
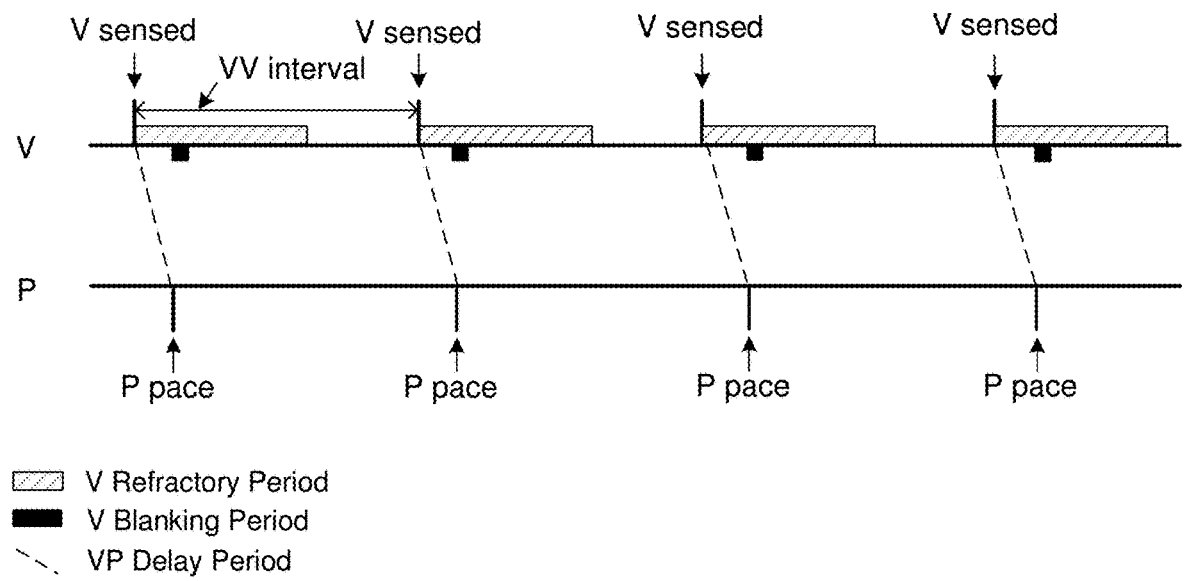

FIGS. 10A and 10B illustrate respectively, early diaphragmatic, and late diaphragmatic, electrical stimulation triggered by intrinsic ventricular events.

Figure 11:
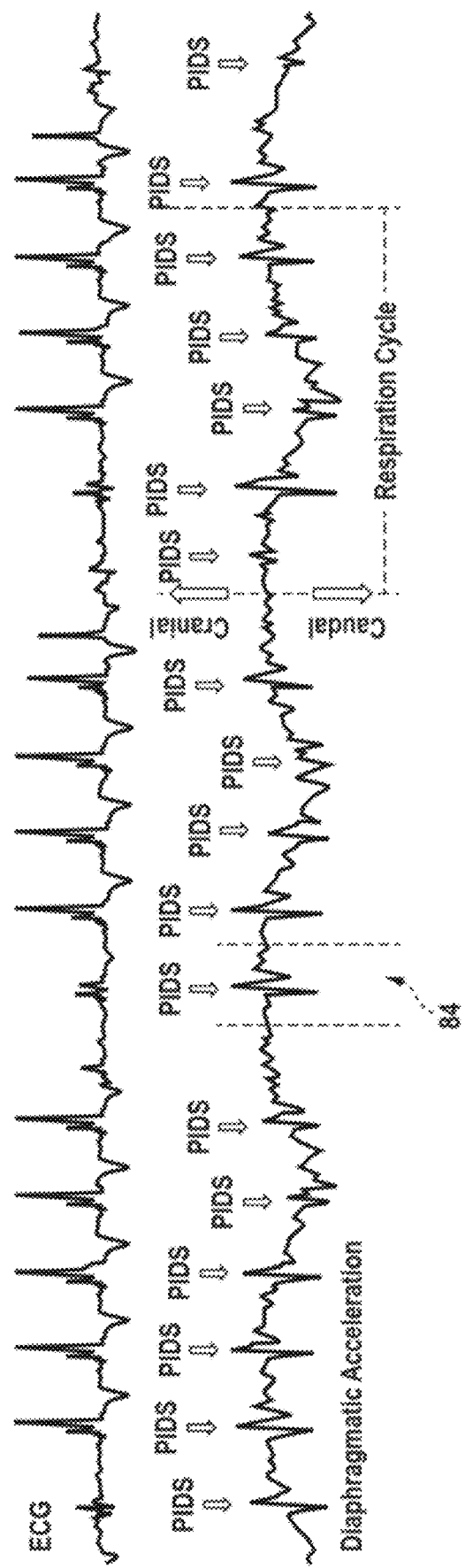

FIG. 11 is a two-trace, common-time-base, graphical presentation relating to electrical ventricular event sensing, associated cardiac-cycle-synchronized, diaphragmatic stimulation, and resulting diaphragmatic and left-ventricle biphasic mechanical motions.

Figure 12:
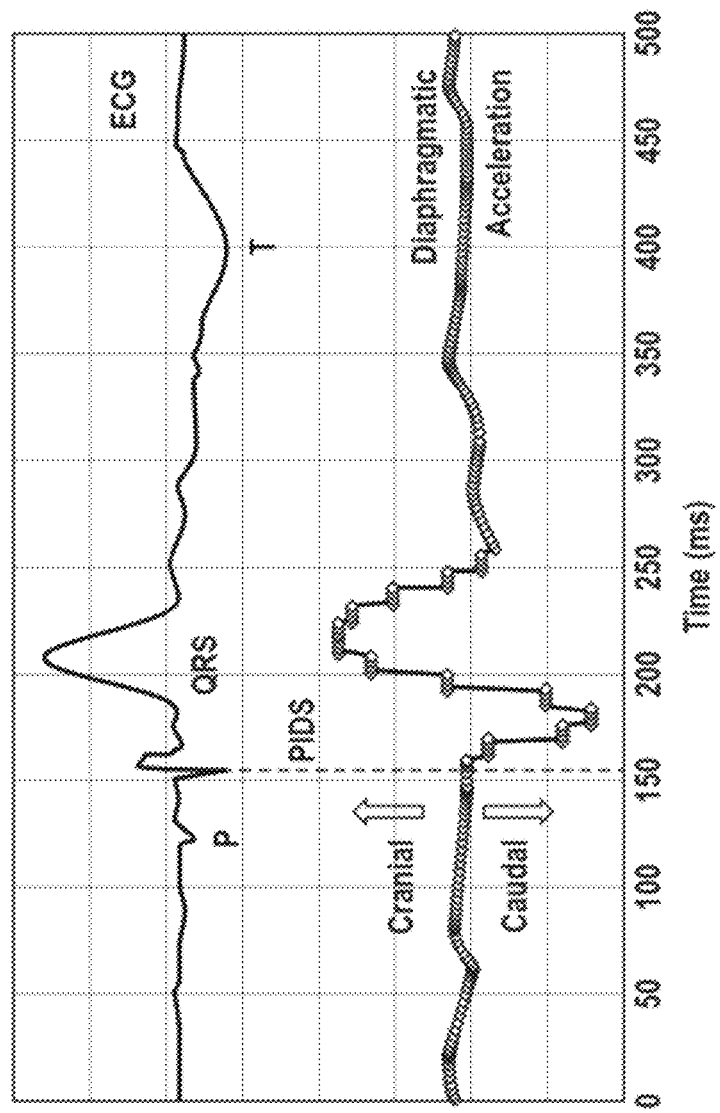

FIG. 12 furnishes an enlarged view of a single cardio cycle event pictured between a pair of spaced, vertical, short dashed lines in FIG. 11.

Figure 13:
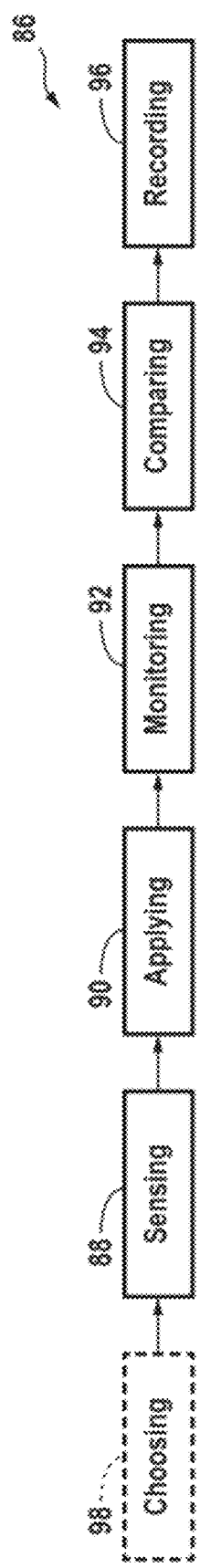

FIG. 13 is a high-level, block/schematic diagram illustrating both the basic, and one modified, form of the architecture of the methodology of the devices of FIGS. 1-5 and 8.

Figure 14A:
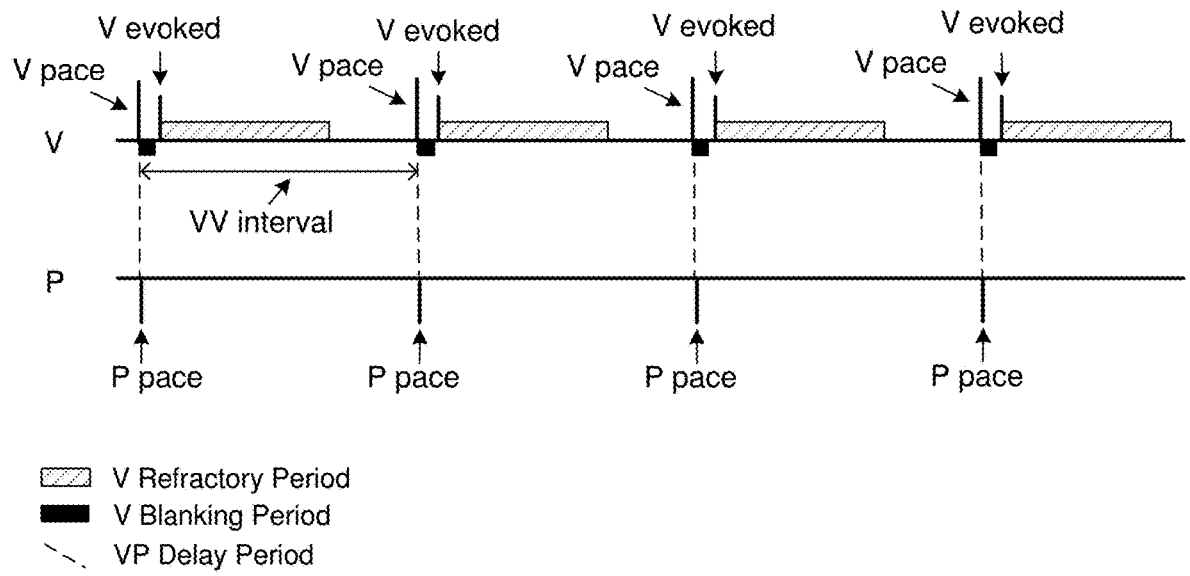

FIG. 14A illustrates early diaphragmatic electrical stimulation triggered by ventricular pacing stimuli.

Figure 14B:
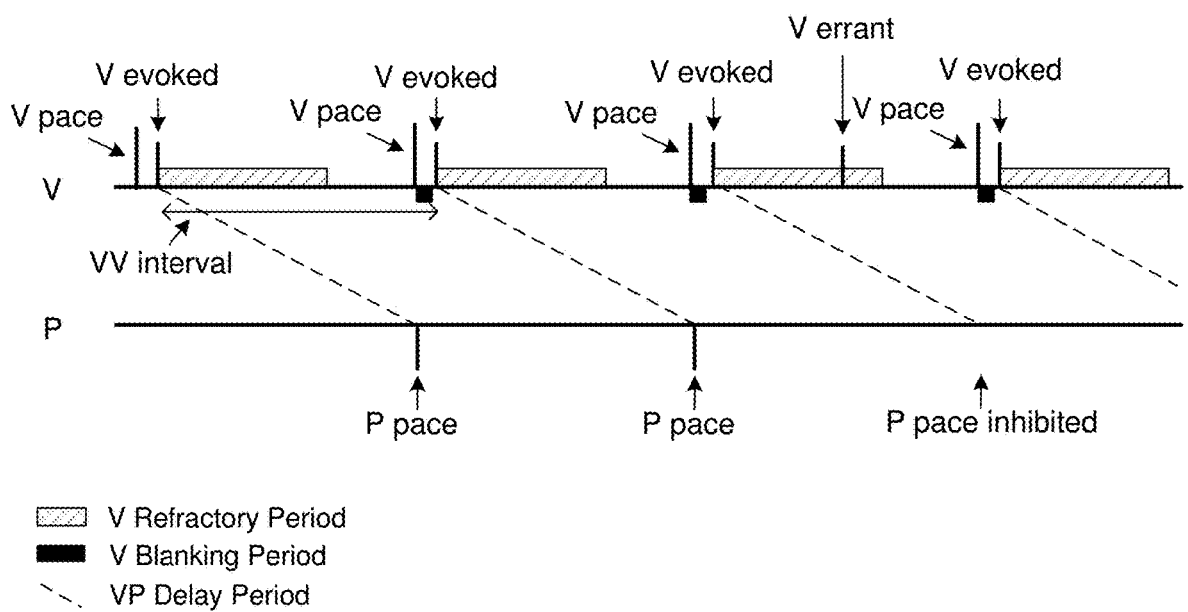

FIG. 14B illustrates early diaphragmatic electrical stimulation triggered by evoked ventricular events.

Figure 15A:
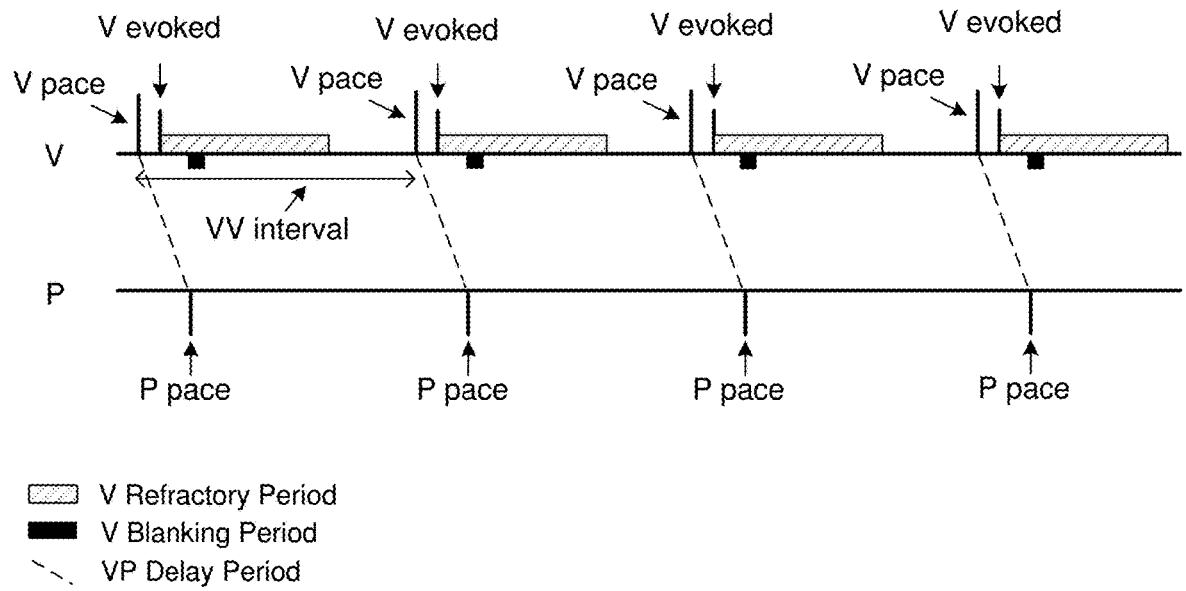

FIG. 15A illustrates late diaphragmatic electrical stimulation triggered by ventricular pacing stimuli.

Figure 15B:
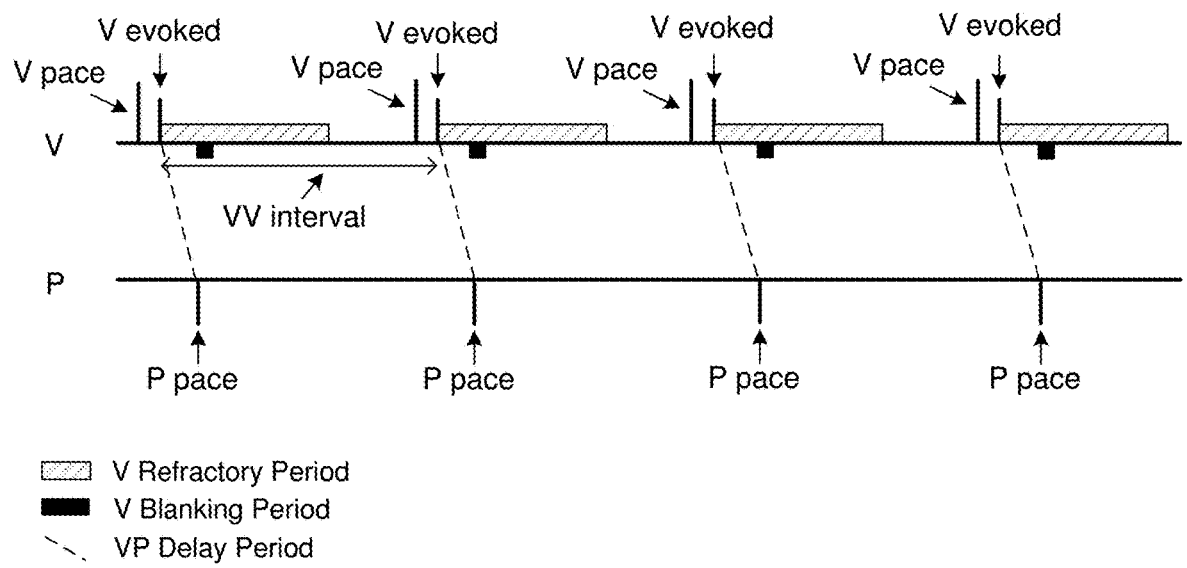

FIG. 15B illustrates late diaphragmatic electrical stimulation triggered by evoked ventricular events.

Figure 16A:
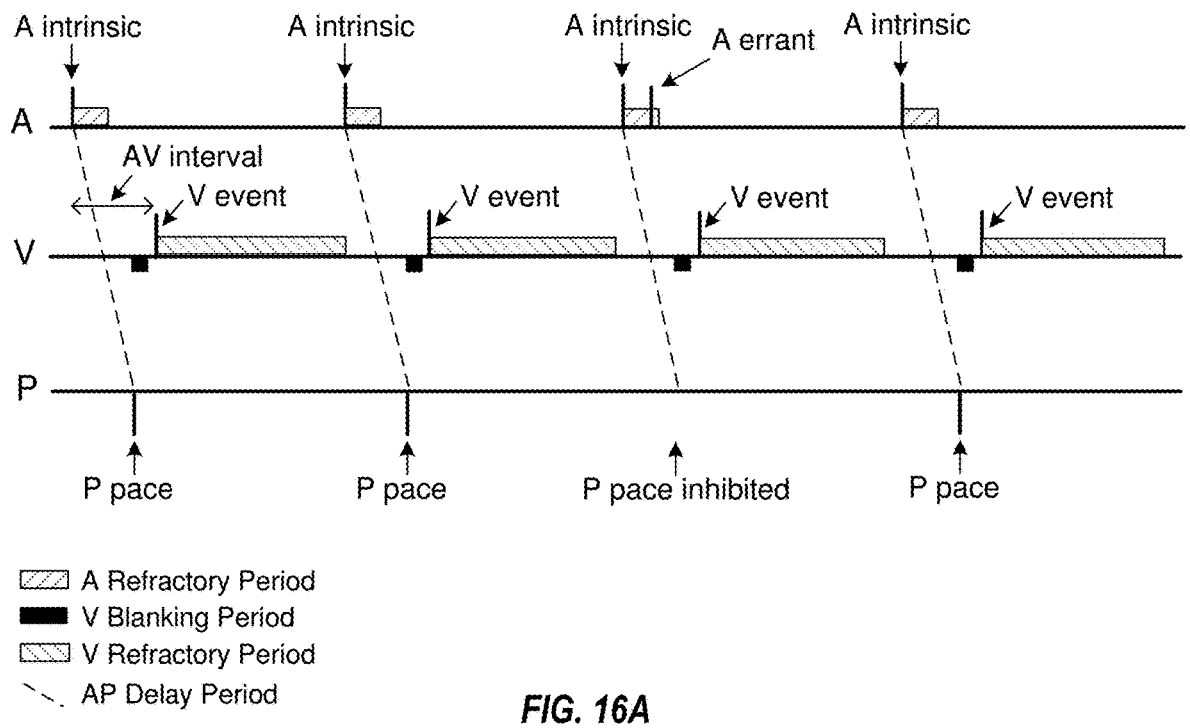
Figure 16B:
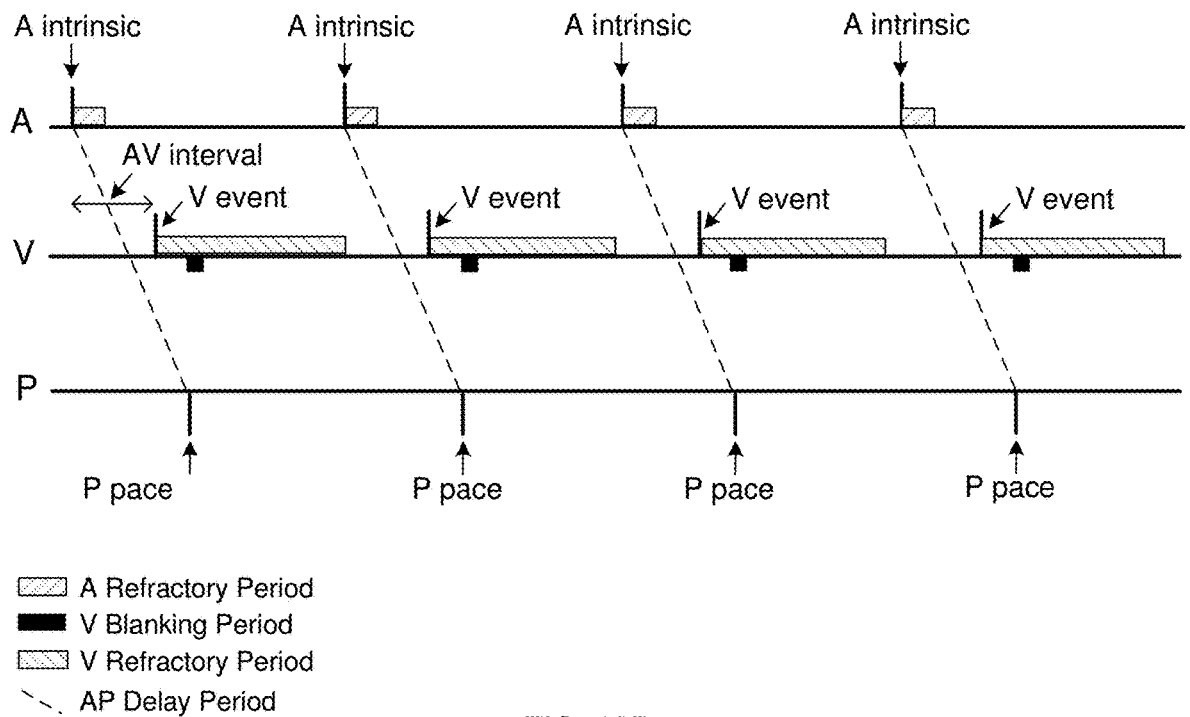

FIGS. 16A and 16B illustrate respectively, early diaphragmatic, and late diaphragmatic, electrical stimulation triggered by intrinsic atrial events.

Figure 17A:
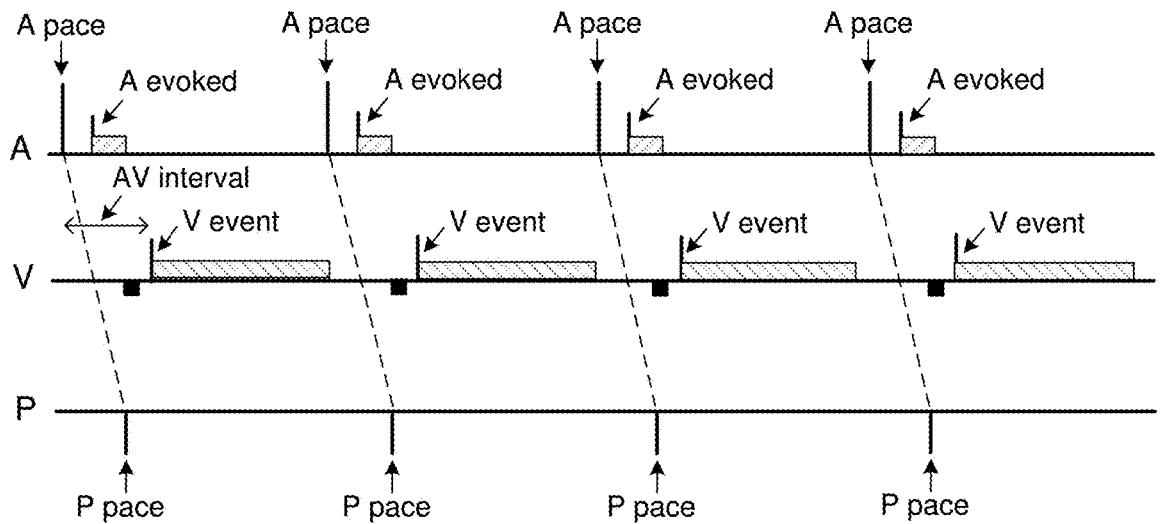

FIG. 17A illustrates early diaphragmatic electrical stimulation triggered by atrial pacing stimuli.

Figure 17B:
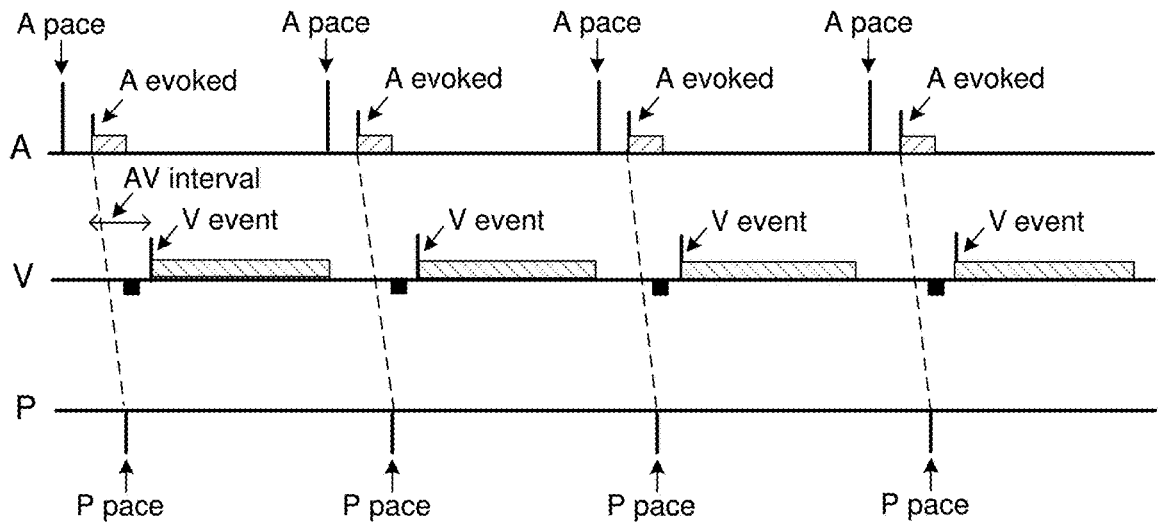

FIG. 17B illustrates early diaphragmatic electrical stimulation triggered by evoked atrial events.

Figure 18A:
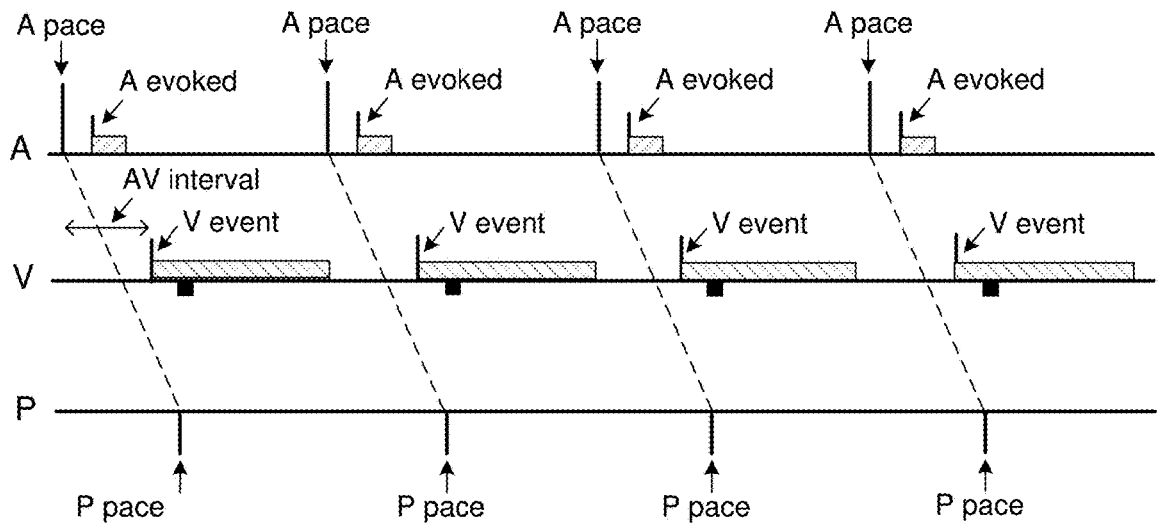

FIG. 18A illustrates late diaphragmatic electrical stimulation triggered by atrial pacing stimuli.

Figure 18B:
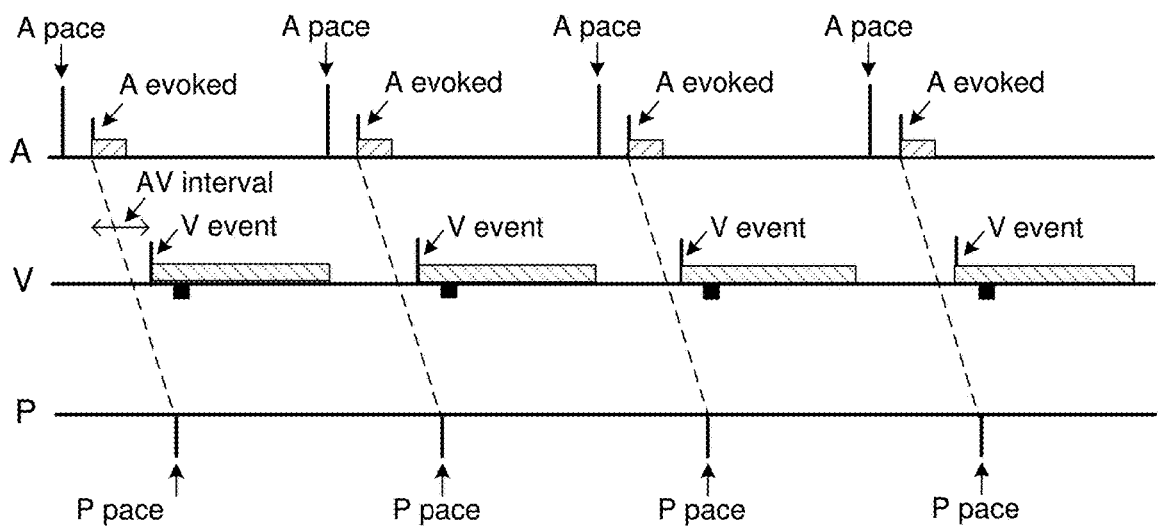

FIG. 18B illustrates late diaphragmatic electrical stimulation triggered by evoked atrial events.

FIGS. 19A-19D are flowcharts of various processes of a method of improving hemodynamic performance through diaphragmatic stimulation.

FIG. 20 is a flowchart of another method of improving hemodynamic performance through diaphragmatic stimulation.

FIG. 21 is a flowchart of a method of distinguishing between valid and non-valid cardiac events.

DETAILED DESCRIPTION

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure.

It should be understood that any aspect of the disclosure disclosed herein may be embodied by one or more elements of a claim.

The present disclosure pertains to an implantable medical device or system, and to an associated methodology, employing, and managed by electrical circuit structure, which features logic-including, internal-control circuitry referred to herein as computer structure, or more simply as a computer, for enhancing hemodynamic performance in subjects with cardiac disease through applying carefully timed, regular, per-cardiac-cycle, synchronized, asymptomatic, electrical pulsed stimulation to the diaphragm intended to induce short-term occurrences of biphasic diaphragmatic motion. In particular, it relates to such a device or system and methodology which, in relation to each such stimulation, and through operation of the included control circuitry (which forms part of what is referred to as electrical circuit structure), monitors and records information regarding resulting, induced diaphragmatic-motion for later review, and to accommodate potential, telemetry-adjusted, systemic-performance adaptation to improve diaphragmatic stimulation characteristics so as to maximize the sought hemodynamic-performance enhancement. The device or system may be configured for selective, remote-telemetry-implemented communication with a device from outside the anatomy, or from another implanted medical device within the anatomy, to allow for other kinds of system-behavioral adjustments, such as ones that relate to timing matters.

The term "hemodynamic performance" is used synonymously herein with the terms "cardiovascular performance" and "cardiac function". The biphasic diaphragmatic motion produced by electrical stimulation, in accordance with practice of the disclosed implantable medical device, is what is called herein caudal-followed-by-cranial motion of the diaphragm. The included "computer-structure" logic componentry, which may be hard-wired to perform its intended functions, or more preferably fully or partially programmable, as by telemetry, may also feature an appropriate microprocessor. It may also include, or be appropriately internally associated with, a suitable "state machine" for implementing various important timing controls, as will be explained below.

Pulsed stimulation of the type mentioned above, properly characterized and applied, triggers, in each case, a very short (only a few tens of milliseconds) pulse-like, biphasic (singular-caudal-followed-by-singular-cranial) motion of the diaphragm, and, relatedly also, a substantially following pumping-relevant motion of the left ventricle in the heart which rests on the diaphragm. This stimulation creates this motion-generating activity in a manner which, when properly and synchronously timed in relation to the onset of left-ventricular contraction, improves hemodynamic performance through enhancing the important cardiac pumping functions of both (a) late diastolic filling, and (b) early systolic contraction.

Asymptomatic stimulation implemented in the practice of the implantable medical device is also referred to herein as PIDS stimulation—the acronym PIDS standing for the phrase "pacing induced diaphragmatic stimulation". The mentioned monitoring and recording for later stimulation-characteristic review, and possible revision purposes, are linked with systemically control-circuitry-performed comparing of actual induced diaphragmatic-motion waveforms with a provided and internally stored reference waveform.

In some expressions of the implantable medical device, systemic and methodologic, are (1) that sensing of what is referred to herein as a valid cardiac event, which may, for example, be a valid electrical ventricular event (V-event), a valid mechanical V-event, a valid electrical atrial event (A-event), or a valid mechanical A-event, and (2) that related, sensing-based, ultimate applying of electrical stimulation to the diaphragm, take place, with the device installed for use with a subject, from an implanted systemic disposition directly adjacent, and preferably in contact with a selected surface region in the subject's diaphragm. This selected surface region, which may be either an inferior or a superior surface region in the diaphragm, and which may be chosen to be at many different, diaphragmatic surface locations, may be disposed either left-lateral, medial or right-lateral relative to the subject's anatomy.

A V-event, in either category (electrical or mechanical), is defined herein as being either the onset of left-ventricular contraction, or a cardiac electrical or mechanical event having a predictably known relationship to such an onset. In one configuration, a valid electrical V-event is treated as being either the electrical R wave or Q wave, and a valid mechanical V-event is treated as being the S1 heart sound. In other configurations, a valid electrical V-event may be a ventricular pacing stimuli or an evoked ventricular event that results from a ventricular pacing stimuli. Cardiac-cycle-by-cardiac-cycle, synchronized, diaphragmatic stimulation may be timed, selectively in different ways. For example, diaphragmatic stimulation may be timed to anticipate a next V-event or to follow a current V-event.

An A-event, in either category (electrical or mechanical), is defined herein as being either the onset of an atrial contraction, or a cardiac electrical or mechanical event having a predictably known relationship to such an onset. In one configuration, a valid electrical A-event is treated as being either the electrical P wave, and a valid mechanical A-event is treated as being the S4 heart sound. In other configuration, a valid electrical A-event may be an atrial pacing stimuli or an evoked atrial event that results from a ventricular pacing stimuli. Cardiac-cycle-by-cardiac-cycle, synchronized, diaphragmatic stimulation may be timed, selectively in different ways. For example, diaphragmatic stimulation may be timed to anticipate a V-event that follows the A-event, or to follow a V-event that follows the A-event.

In certain featural expressions of the present implantable medical device, systemic and methodologic, is the effective incorporation in the proposed device and associated methodology of a focus, through the use of a device-included accelerometer, preferably multi-axial in character, and even more preferably three-dimensional in nature, on the monitoring and recording of the mechanical waveform of per-cardiac-cycle, mechanical diaphragmatic biphasic motion which is actually produced by applied, diaphragmatic electrical stimulation in comparison with a pre-set, diaphragmatic-motion reference waveform. Information regarding non-conformance of these two waveforms—computer acquired and recorded by the implantable medical device— is used for periodic device-performance review, and in this context, is very useful to support the making of appropriate, per-cardiac-cycle, electrical stimulation-character modifications to enhance such performance.

It should be noted that while different embodiments of the implantable medical device may use different-axial-sensitivity accelerometers, preferred in most applications is the inclusion and use of a three-dimensional, i.e., three-axis, accelerometer. Accordingly, the preferred systemic and methodologic descriptions presented herein below are described in the context of employment of a three-dimensional accelerometer.

Various configurations of the implantable medical device are disclosed. One configuration features, as an entirety— i.e., as a singularity—a self-contained, self-powered, singular capsule construction configured to be placed in direct contact with the diaphragm. A second configuration features a distribution of components organized into two arrangements of components separated by an interconnecting lead structure. The lead structure includes electrodes and is configured to be implanted such that one or more electrodes are on or near the diaphragm. A third configuration features the incorporation of the electrical and mechanical componentry that implements diaphragmatic stimulation into an implantable cardiac device. An implantable cardiac device may be, for example, a CRM device, such as a pacemaker, or a defibrillator. In these configurations, the pacing or defibrillation functionality of the cardiac device may involve endovascular leads implanted within the heart or extravascular leads placed on or near the surface of the heart, while the diaphragmatic stimulation functionality of the device is provided by a lead placed in contact with the diaphragm.

Other forms of the implantable medical device, not pictured or discussed herein, and differing specifically from the two, just-mentioned forms, are recognized to be possible to address different implantation applications, wherein the various device components, described below for the two implantable medical device forms particularly set forth herein, become organized in different implantable ways.

Regarding systemic performance functionality in the context of the present disclosure, the same, basic methodology, in terms of the end-result achieving of hemodynamic/cardiovascular performance enhancement through triggered pulses of biphasic motion introduced into the diaphragm, is implemented in both of the disclosed forms of the implantable medical device.

Stimulation-induced diaphragmatic movements, as just generally described above, are, in relation to normal respiration-motion frequency (typically about 0.2-0.3-Hz), and as mentioned, short-term, relatively high-frequency (typically about 12-15-Hz), pulse-like motions. These quick motions are superimposed on the regular, and much lower frequency, diaphragmatic respiration movements. The initial, short-term caudal movement effected by diaphragmatic stimulation pulls on the left ventricle, and if well timed, such stimulation-resulting "pulling" increases the atrial contribution to left-ventricular filling during late diastole (i.e., a so-called "atrial kick") with a resulting subsequent increase in stroke volume via the recognized, Frank-Starling mechanism. The secondary, stimulation-induced movement of the diaphragm which is cranial, and which is also much faster than regular diaphragmatic respiratory motion, causes the left ventricle to be "kicked" upwardly, and if this secondary movement occurs in the early part of systole, and prior to the closure of the mitral valve, it enhances cardiac function further by increasing the momentum of ventricular contraction.

Accordingly, in relation to achieving desired hemodynamic enhancement, it is important to optimize the timing between the onset of ventricular contraction and diaphragmatic stimulation so that the actual timing and impact of the mentioned caudal and cranial components of motion as they affect cardiac function are maximized Such maximizing is subject-specific, in relation to a given subject's particular cardiac structure (electrically and mechanically), and accordingly, medically-determined, properly associated, subject-specific timing requirements are initially set or programmed into the device. When all operational parameters are properly put in place, the present implantable medical device successfully accomplishes appreciable hemodynamic-performance optimization.

As mentioned above, two fully implantable and self-powered, configurations of the device are illustrated and described herein, one of which, as stated above, is a single-unit, self-contained, capsule-form arrangement, and the other of which has a distributed-component, communication-lead-line-interconnecting form.

According to one manner of describing generally the structural nature of the implantable medical device, what is proposed is a device including (a) bi-modal (cardiac-electrical-activity sensing in one mode, and related diaphragmatic electrical stimulating in the other mode) electrode structure operatively connectable to a selected surface region in a subject's diaphragm, and (b) monitoring and controlling circuit structure which is connected to the electrode structure, and operable (1) to receive and process electrode-structure-sensed electrical cardiac activity when the electrode structure, under the influence of the circuit structure, is functioning in its sensing mode, and (2), based on such receiving and processing, to communicate to the diaphragm via the electrode structure, when the latter is functioning, also under the influence of the circuit structure, in its stimulating mode, appropriate diaphragmatic stimulation.

In another configuration of the implantable medical device, what is proposed is a device including (a) a set of electrodes configurable to from (1) a unipolar electrode arrangement including at least two electrodes, which when implanted in a subject are spaced apart by at least 2 cm, and (2) a bipolar electrode arrangement, including at least two electrodes, which when implanted in a subject are spaced apart by at least 0.1 cm, each electrode arrangement operatively connectable to a selected surface region of a subject's diaphragm, and (b) monitoring and controlling circuit structure which is connected to the unipolar electrode arrangement and the bipolar electrode arrangement, and operable (1) to receive and process electrical cardiac activity sensed by the unipolar electrode arrangement, and (2), based on such receiving and processing, to deliver through the bipolar electrode arrangement, diaphragmatic electrical stimulation.

In a more particular sense, (a) the selected, diaphragmatic surface region is disposed (1) at a location which is either left-lateral, medial, or right-lateral, within a subject's anatomy, and (2) in all instances out of contact with, the subject's heart, and (b) the mentioned circuit structure includes computer structure which specifically operates, relative to the circuit structure's delivery of electrical stimulation through the electrode structure, to control appropriately predetermined timed relationships relative to noted presences, in received and monitored cardiac-cycle electrical-activity information, of valid electrical cardiac events, e.g. electrical V-events. Additionally, contemplated in the practice of the implantable medical device are two, different categories of such predetermined timed, or timing relationships, one of which involves anticipation of a next-expected, valid, cardiac-cycle, electrical cardiac event, e.g., a V-event, and the other of which involves a following of the last-sensed, valid, cardiac-cycle, electrical cardiac event, e.g., a V-event. These same, two categories of timing relationships are equally applicable to another form of the device, discussed below, which further includes an accelerometer (single or plural-axis), also referred to herein as a mechanical sensing structure, that is designed to detect heart sounds, and in particular S1 heart sounds, as valid mechanical cardiac event, e.g., mechanical V-events.

An augmented form (the "another form" of the device mentioned immediately above) of this just-presented descriptions of the devices is one in which the proposed device further includes a three-dimensional accelerometer (called also a mechanical sensing structure), (a) disposed adjacent, and operatively associated with, the electrode structure for contact-associated disposition in a motion-sensing relationship with, and with respect to, the subject's diaphragm, (b) operatively connected to the mentioned circuit structure, and (c) constructed to be responsive to any motion produced in the subject's diaphragm as a consequence of diaphragmatic electrical stimulation, and in relation to such responsiveness, to generate and communicate to the circuit structure a diaphragmatic-motion confirmation signal possessing a waveform which is directly indicative of such motion.

In a further way of thinking about the accelerometer-including device, the circuit structure's included computer structure features a waveform monitoring and recording substructure for comparing the waveform of a communicated confirmation signal with a reference waveform, and recording the conformation-signal waveform for subsequent review.

Another way of thinking about the implantable medical device, in relation to the inclusion therein of an accelerometer, is that, in accordance with a modified form of the device, (a) an included accelerometer functions, additionally, for sensing, in a subject's cardiac cycles, cardiac-cycle, S1 heart-sound, mechanical activity, e.g., a valid mechanical V-event, which is discernible at the selected, diaphragmatic surface region, and that (b), the included circuit structure receives this mechanical valid V-event information from the accelerometer, and is operable, in predetermined timed relationships to noted presences, in such received mechanical S1-heart-sound, of valid V-event information, to deliver asymptomatic electrical stimulation through the electrode structure to the subject's diaphragm for the purpose of triggering the intended biphasic, caudal-followed-by-cranial, motion of the diaphragm.

A further modified form of the basic device, contemplated for implementation in certain applications, and representationally pictured, described and included herein in each of the two principal embodiments disclosed, is one wherein the computer structure which forms part of the included circuit structure possesses timing-adjustment substructure capable of making an adjustment periodically in the predetermined timed relationship which determines when, in relation to a sensed, valid V-event, diaphragmatic electrical stimulation occurs. This modification is versatile in its utility, offering the possibility of adjusting, either remotely, or internally automatically if desired, such stimulation timing in a manner aimed at further enhancing a subject's hemodynamic performance if, and as, the subject's heart-behavior conditions change over time.

From a methodologic point of view the implantable medical device offers a method for improving the hemodynamic performance of a subject's heart. In one implementation based on V-event, the method includes, from adjacent a selected surface region in the subject's diaphragm which is out of contact with, the heart, (1) sensing and noting the presences in the subject's cardiac cycles of a selected one of (a) per-cycle valid electrical, and (b) per-cycle valid mechanical, V-events, (2) based upon such sensing, and upon noting each of such selected, V-event presences, applying, in a predetermined timed relationship to such a noting, associated, asymptomatic electrical stimulation directly to the diaphragm, preferably at the selected diaphragmatic surface region, for the purpose of triggering biphasic, caudal-followed-by-cranial motion of the diaphragm, (3) following the applying step, monitoring the waveform of resulting diaphragmatic motion, (4) after performing the monitoring step, comparing the monitored diaphragmatic-motion waveform with a reference, diaphragmatic-motion waveform, and (5) on completion of the comparing step, recording the monitored, diaphragmatic-motion waveform for later review.

The methodology further includes (1) choosing the selected diaphragmatic surface region to be on one of (a) the inferior, and (b) the superior, side of the diaphragm, and (2) choosing the selected, per-cycle valid V-event whereby, if it is to be electrical, it may be one of (a) the R wave, and (b) the Q wave, and if mechanical, it is the S1 heart sound.

Self-Contained, Fully Implantable PIDS Device

Turning now to the drawings, and referring to FIGS. 1-5, there is shown a first form of a self-contained, self-powered, fully implantable medical device 20 configured to improve the hemodynamic performance of a subject's heart. The device 20, referred to herein as a pacing induced diaphragmatic stimulation (PIDS) device, accomplishes such improvement, as will be explained, through applying specially timed, cardiac-cycle-synchronized, asymptomatic, electrical stimulation to the subject's diaphragm directly to produce very short duration, relatively high-frequency, bi-phasic motion of the diaphragm, which motion becomes communicated/applied directly to the underside of the left ventricle in the heart to create, essentially, a diaphragmatic-motion-following, bi-phasic "pumping" motion in and for the underside of, and thus within the left-ventricle.

The PIDS device 20, as seen in FIGS. 1-4, has what is referred to herein as a singular capsule form 22. This form features a small, easily implantable, elongate, thin, non-electrically-conductive, and appropriately biocompatible capsule body, or capsule, 24 having the shape shown, with a length herein of about 1.25-inches, a width of about 0.5-inches, and a thickness of about 0.125-inches. Body 24, has a hollow interior 24*a* (see FIGS. 3 and 4), and possesses an elongate, outside, diaphragm-contacting face 24*b* (see FIGS. 1 and 2), also referred to herein as an electrode face, near the opposite ends of which are positioned two, spaced (by about 1-inches), and outwardly exposed, bimodal electrodes 26, 28, referred to collectively herein as bimodal electrode structure. Electrodes 26, 28 present exposed, circular faces 26*a*, 28*a*, each having a diameter herein of about 0.15-inches. Generally speaking, these electrodes function, in an implanted-condition operation of PIDS device 20, both to sense heart-related electrical activity—done in a so-called first, or one, mode of operation, and to apply controlled, asymptomatic, electrical stimulation to the diaphragm—done in a so-called second, or other, independent mode of operation.

The specific capsule shape illustrated in FIGS. 1-4, inclusive, and the several specific dimensions just mentioned, are not critical, and may be varied selectively according user wishes to suit different, particular implantation applications. What is important, of course, is that the shape and dimensions of capsule 24 be suitable and comfortable, and designed for minimally invasive placement for operational residence within a subject's anatomy. As will be explained below, while preferred placement involves, effectively, stabilized attachment to a surface region which is near the upper portion of a subject's diaphragm (inferior or superior), there may be other diaphragmatic locations that are suitable for placement. The same statements just made about shape and sizing, addressed initially specifically herein with respect to the capsule form of the device now being discussed, are also applicable to a still-to-be-described, second embodiment pictured in FIG. 8A, and third embodiment pictured in FIG. 8B. Respecting each of the embodiments of the PIDS device disclosed herein, while users/installers of it may readily choose various, different, appropriate, and preferably minimally-invasive, surgical procedures to carry out implantation within a subject's anatomy, laparoscopy is considered to be a good choice for device placement on the inferior side of the diaphragm, and thoracotomy, a good choice for such placement on the superior side of the diaphragm.

A suitable, conventional, non-electrically-conductive, biocompatible mesh 30 (see FIGS. 1 and 2), is affixed to the capsule face 24*b* to facilitate, following device implantation, natural-process anatomical bonding, for positional stabilization, to a selected surface region (inferior or superior) in/on a subject's diaphragm. Inclusion of such a mesh is optional, but useful. As will be further discussed, inferior surface-region placement on the diaphragm at a diaphragmatic location which is left-lateral, medial or right-lateral in a subject's anatomy is possible. Additionally, in circumstances involving superior surface-region placement, such placement should be one where the capsule 24 is out of direct contact with the heart.

Included in the PIDS device 20, housed within the hollow interior 24*a* in capsule body 24, are various electrical and mechanico-electrical, device-operational components, including an electrical circuit structure 32 which, through the included presence in it of logic-including, internal-control circuitry (still to be pointed out in the drawings), manages all device electrical-performance activity, a battery 34 which furnishes all needed operating power for the device, and a multi-axial (three-dimensional herein) accelerometer, or mechanical sensing structure 36 which, with the device in an appropriate anatomically implanted condition, senses a variety of mechanical and sound activities, such as diaphragmatic-motion activities, and heart sounds. Regarding the accelerometer's sensing of diaphragmatic-motion activity, a sensing capability enhanced by its proposed, and intended, implanted placement in what is referred to herein as a motion-sensing relationship directly on the diaphragm, it produces an important electrical, diaphragmatic-motion confirmation signal for delivery to electrical circuit structure 32, which signal is directly indicative of the waveform of such motion. This signal is useful for assuring that actually applied diaphragmatic electrical stimulation is as best-suited as possible for triggering the desired biphasic diaphragmatic movement intended to maximize hemodynamic performance enhancement. This assuring comes about because, according to the methodology of the present device, the waveform represented by the accelerometer's supplied confirmation signal is regularly compared with a reference waveform known to the device.

Heart sounds sensed by the included accelerometer are useful for many purposes, and especially the S1 heart sound which is used, in an already mentioned, modified form of the device to act, and be recognized as, a valid mechanical V-event in relation to which appropriate timing for the application of a diaphragmatic stimulation is measured.

Other interesting information which may be obtained from the response of the accelerometer, not directly related to the practice and methodology of the present device, but nevertheless available, for example to a physician monitoring various subject conditions that may, in different ways, have a relationship to hemodynamic performance, include subject activity levels, subject body posture, respiratory information, such as respiration rate, sleep-disordered breathing events, heart murmurs, and perhaps others.

Figure 1:
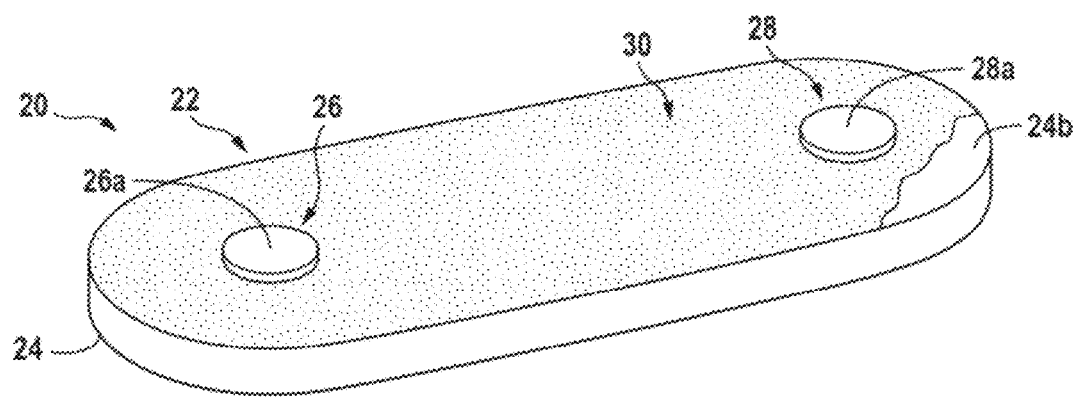
FIG. 1 is an isometric, electrode-side, facial view of a first embodiment of a fully implantable fully self-contained, self-powered, singular capsule-form embodiment of a device for improving hemodynamic performance through diaphragmatic stimulation, referred to herein as a pacing induced diaphragmatic stimulation (PIDS) device.
Figure 2:
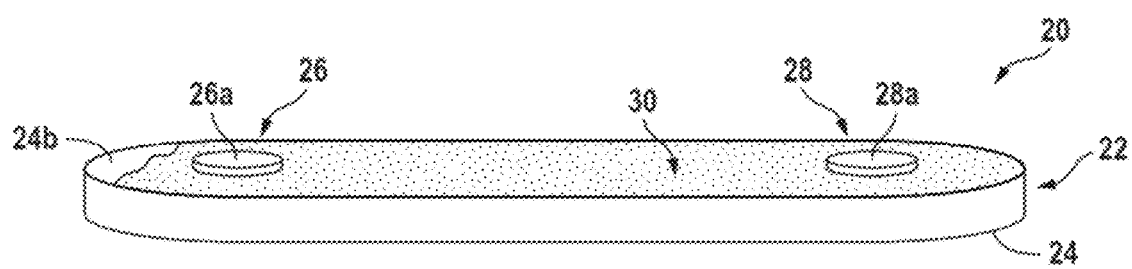
FIG. 2 is a same-scale, lateral isometric view of the PIDS device shown in FIG. 1, slightly rotated about two axes relative to what is seen in FIG. 1.
Figure 3:
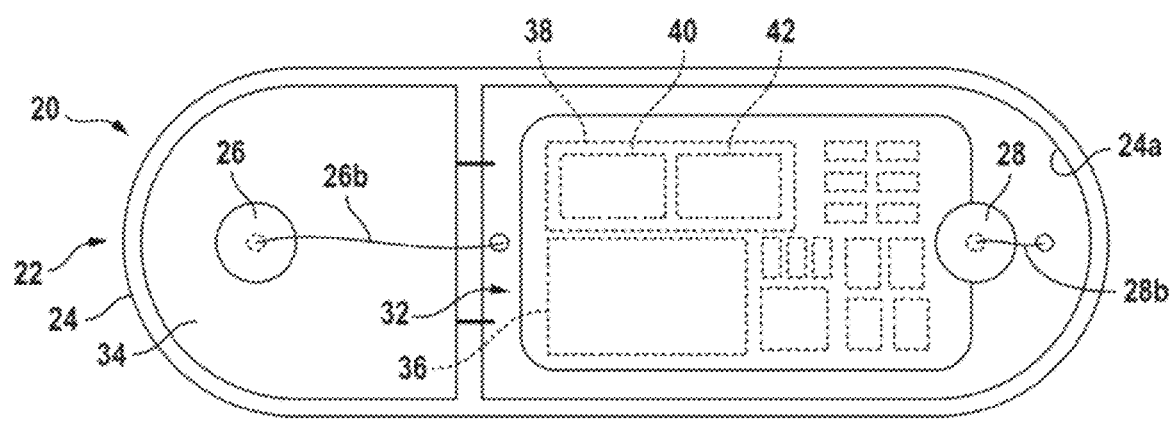
FIG. 3 is a plan view of the PIDS device shown in FIGS. 1 and 2, drawn on about the same scale used in these two figures, and pictured with the body of the capsule opened to show internally contained electrical circuitry, an accelerometer, and an included battery.
Figure 4:
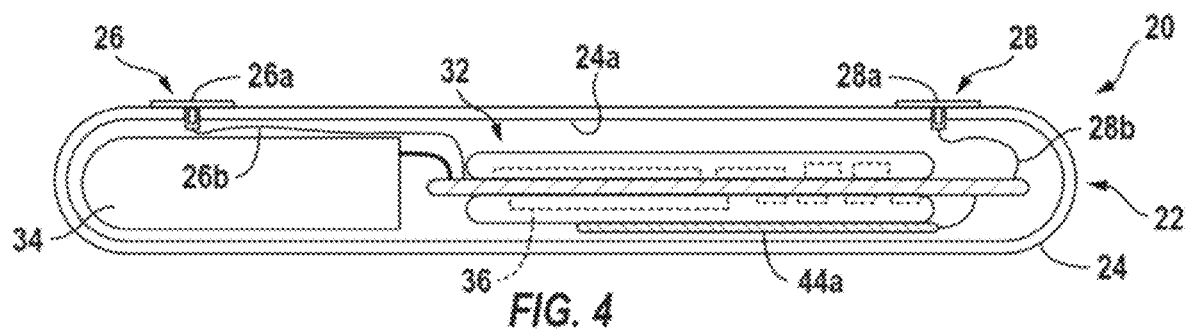
FIG. 4, which uses the same drawing scale as that seen in FIG. 3, is a lateral cross section taken generally from the lower side of FIG. 3.
Figure 5:
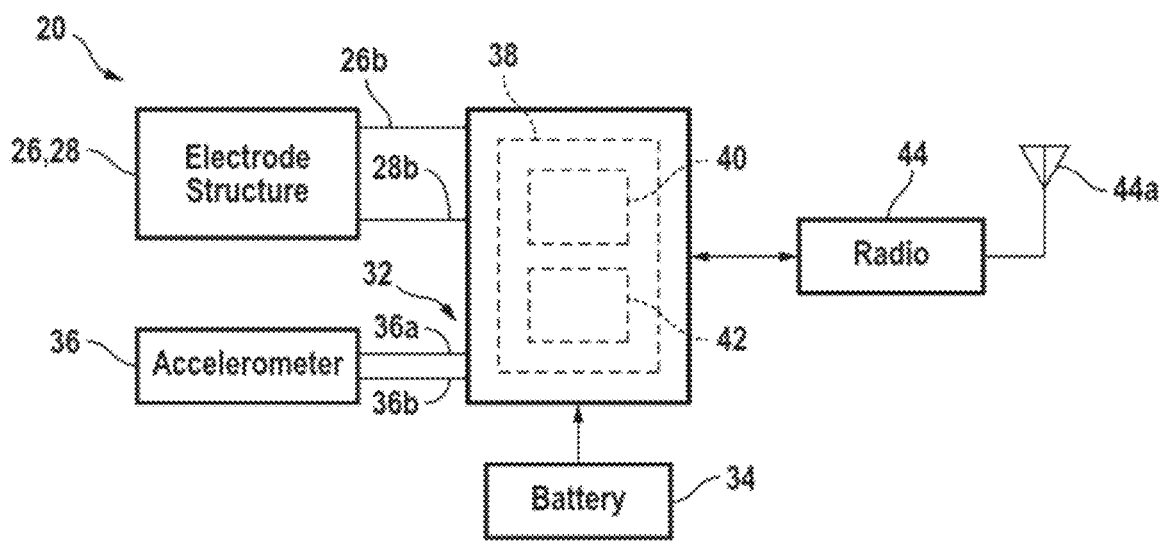
FIG. 5 is a basic block/schematic diagram illustrating electrical and mechanical componentry that implements diaphragmatic stimulation. The componentry may be incorporated in any of the embodiments of the PIDS device disclosed herein.

An operative connection between circuit structure 32 and accelerometer 36 is represented in FIG. 5 by conductors 36a, 36b.

Electrodes 26, 28 are operatively connected to circuit structure 32 for bimodal (sensing/stimulating) operation through what may be thought of as bi-directionally employed conductors 26b, 28b, respectively, and these electrodes, circuit structure 32, battery 34, and accelerometer 36 are all appropriately operatively interconnected to function collaboratively in manners shortly to be described.

Appropriate, conventional, analogue-to-digital, and digital-to-analogue converters, not specifically shown in the drawings, are incorporated where needed.

Electrical circuit structure 32, as mentioned generally above, features what is referred to as logic-including, internal-control circuitry, also referred to herein as computer structure, or more simply as a computer 38, possessing waveform monitoring and recording substructure 40, and optionally, timing adjustment substructure 42. Preferably, computer 38, which could be fully hard-wired to perform its intended functions, is herein incorporated and configured with a microprocessor, or the like, so as to be at least partially, if not fully, algorithmically software-programmable structure—programmable, in the device now being described, not only initially, but at later times, by close-proximity telemetry communication accommodated through a conventional, short-range radio 44 having an antenna 44a. Computer 38 also includes a suitable, conventionally designed state machine (not specifically, separately illustrated in the drawings) for implementing various important timing controls, as will be explained below herein.

Choices for, and appropriate organizations of, specific electrical circuitry elements, including logic-structure computer-associated elements, and all hard-wired-managed, and/or software-dictated-and-managed, operational programming which controls systemic and methodologic functioning of the device, are designable and includable employing conventional, state-of-the-art devices, algorithms, and other knowledge in the possessions of those persons who are generally skilled in the relevant arts, and for that reason are not specifically detailed herein. The systemic structural descriptions presented herein, as well as the methodological, operational features of the device discussed, will well arm those generally-skilled persons to practice all aspects of the present device.

Turning attention now to FIGS. 6A, 6B, 7A, 7B, along with continued references, as appropriate and helpful, to FIGS. 1-5, inclusive, FIG. 6A furnishes a frontal view of an internal portion 46 of a subject's anatomy illustrating, generally at 48, implanted positioning therein proposed for the PIDS device 20 pictured in FIGS. 1-4. In FIG. 6A, the PIDS device 20 is simply illustrated by a very evident, generally horizontally disposed, thickened, dark line, and specifically, what is illustrated, is that capsule 24 in this device is placed at a selected surface region 48a on the inferior side of the subject's diaphragm 50. More specifically, the capsule 24 of the PIDS device 20 is positioned left-laterally in the subject's anatomy, clearly out of contact with the subject's heart 52, and actually in a modest state of compression between the inferior side of diaphragm 50 and the subject's immediately underlying liver, seen generally, and fragmentarily only, at 54. The PIDS device 20 may also be placed medially or right-laterally. In a very specific sense, capsule 24 is disposed with its electrode face 24b (not specifically seen or marked in FIG. 6A) facing the inferior surface of the diaphragm, with electrodes 26, 28 (also not specifically seen in this figure) directly contacting diaphragmatic surface region 48a. In relation to what is seen in FIG. 6A, and as was mentioned earlier herein, capsule 24 may be implanted on the inferior side of the diaphragm 50 by accessing the abdominal cavity through conventional laparoscopy.

Turning attention to FIG. 6B, this figure also shows just-mentioned, internal, anatomical portion 46, and is similar to FIG. 6A, except that it shows an alternative placement in the subject's anatomy for the capsule 24 of the PIDS device 20. In FIG. 6B, the capsule 24 has been placed on the superior surface of diaphragm 50 at an implantation position generally shown at 56, and specifically on a selected, diaphragmatic surface region 56a, which has a left-lateral disposition in the subject's anatomy similar to the left-lateral implantation disposition pictured on the underside of diaphragm 50 in FIG. 6A. The PIDS device 20 may also be placed medially or right-laterally. In either location, the capsule 24 is disposed with its electrode face 24b (not specifically seen or marked) facing the superior surface of the diaphragm, and with electrodes 26, 28 (also not specifically shown in FIG. 6B) directly in contact with the diaphragm.

In the disposition shown in FIG. 6B for capsule 24, the capsule is slightly compressed between the superior surface of diaphragm 50 and the underside of the subject's left lung 58. In relation to the positioning shown for the capsule 24 in FIG. 6B, and as was mentioned earlier herein, this capsule may be implanted through conventional thoracotomy, or via a laparoscopic sub-xiphoid approach. In either case, access to reach the thoracotomy location for accessing the diaphragm 50 may be obtained using an extrathoracic subcutaneous tunneling technique.

Regarding the implantation dispositions for the PIDS device 20 shown in FIGS. 6A, 6B, in each of these dispositions the electrodes and the accelerometers are essentially in direct contact with the described and illustrated surface regions in the diaphragm, out of direct contact with the heart. Additionally, in each of the device dispositions, the electrodes of the respective devices are well positioned to detect easily heart-associated electrical activity, and the accelerometers are similarly positioned to detect easily heart sounds, and, of course, diaphragmatic movement/motion.

Distributed, Fully Implantable PIDS Device

Figure 8A:
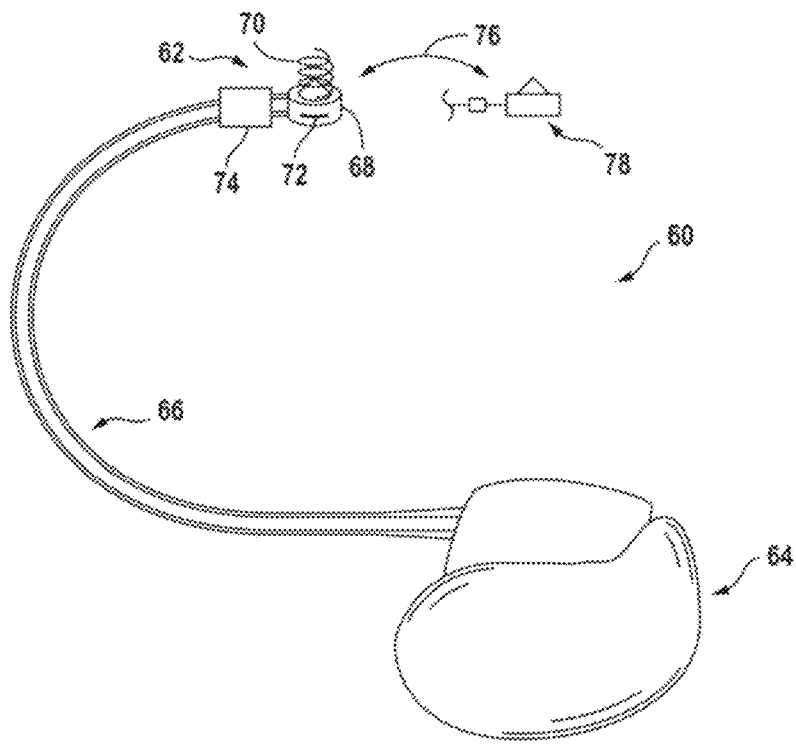
FIG. 8A illustrates a second embodiment of a fully implantable PIDS device for improving hemodynamic performance, including two assemblies that are separated from one another by an interconnecting communication lead structure.
Figure 8B:
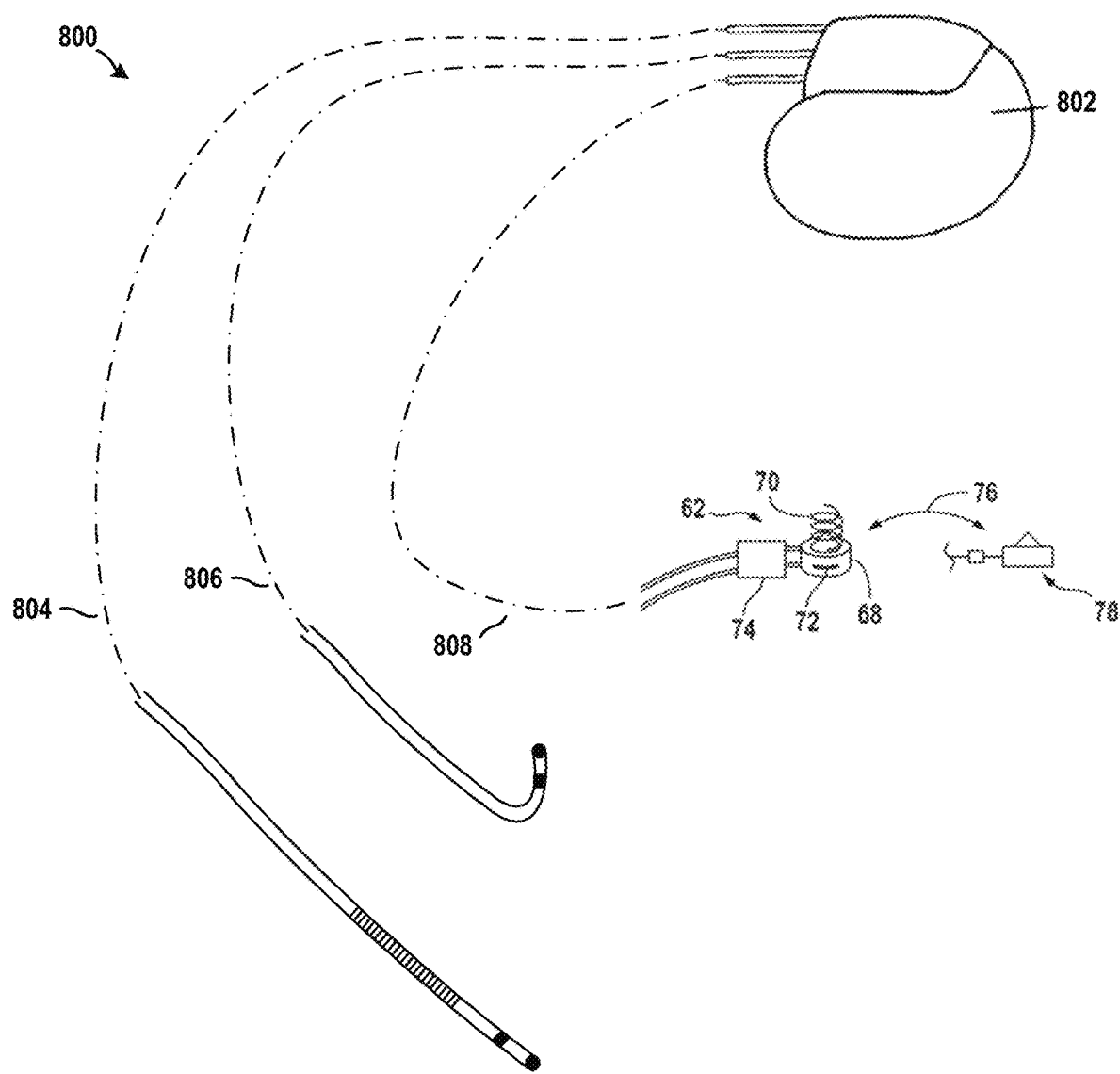
FIG. 8B illustrates a third embodiment of a PIDS device, wherein electrical and mechanical componentry that implements diaphragmatic stimulation is incorporated into a fully implantable cardiac device, e.g., a pacemaker or defibrillator.
Figure 9A:
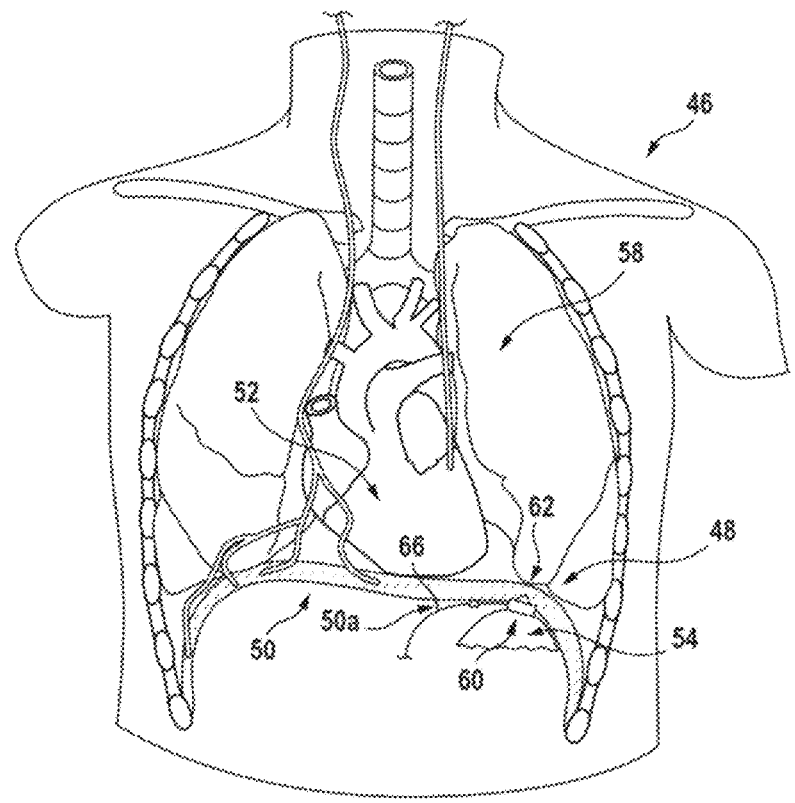
FIGS. 9A, 9B are similar to FIGS. 6A, 6B, differing in that they illustrate two, alternative, proposed implant locations for the second embodiment of the PIDS device illustrated in FIG. 8A.
Figure 9B:
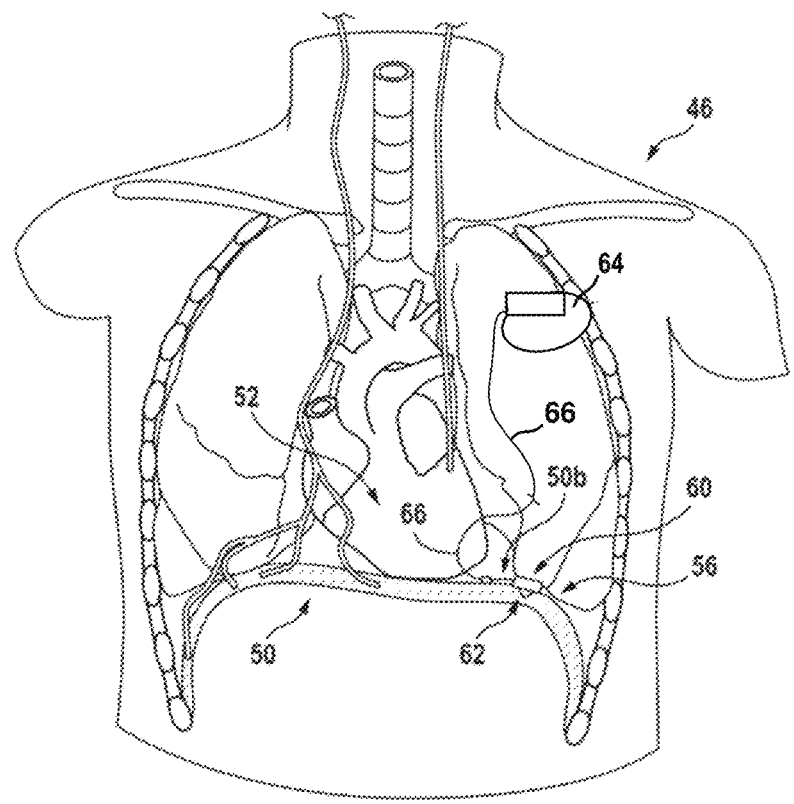

Turning now to FIGS. 8A, 9A, 9B, there is shown a second form of a self-contained, self-powered, fully implantable PIDS device 60 configured to improve the hemodynamic performance of a subject's heart. Focusing attention initially here on what is shown in the FIG. 8A, the second form of a PIDS device 60 is a self-powered, implantable, distributed PIDS device—distributed in the sense that it includes a first component assembly 62 and a second component assembly 64, operatively interconnected by appropriate, elongate, communication lead structure 66. Except for the fact that this form of the PIDS device has the just-mentioned distributed nature, and the further fact that its distributed componentry, when implanted in a subject's anatomy as pictured generally in FIGS. 9A, 9B is uniquely associated with this distributed embodiment form, it includes all of the operatively interconnected electrical and mechanico-electrical componentry described above for self-contained form of a PIDS device 20—interconnected as illustrated schematically in FIG. 5. Additionally, the performance of distributed PIDS device 60 is essentially identical to that of self-contained PIDS device 20.

Included within the first component assembly 62 are a cylindrical housing 68, from one side of which projects a spiral-form, diaphragm-attaching electrode 70, and in which is appropriately mounted a three-dimensional accelerometer 72 represented by a small thickened and darkened line in FIG. 8A, and next to the housing 68, and represented by a small rectangle, another electrode 74 which, together with the spiral electrode 70, form the previously mentioned bimodal electrodes. Collectively, the electrodes 70, 74 constitute the bimodal electrodes structure discussed above.

Shown immediately to the right of first component assembly 62 in FIG. 8A, and visually linked to the image of this component assembly by a curved, double-arrow-headed arrow 76, is a symbolic representation 78 of the first component assembly 62, which symbolic representation is employed (as can be seen) in each of FIGS. 9A, 9B to enable a simpler way of picturing there the respective presences of the first component assembly 62 in the anatomical images presented in these two figures.

The spiral-form electrode 70, is designed to enable spiral, attachable embedment into the structure of a subject's diaphragm for securing the first component assembly 62 in place, and in a manner whereby both electrodes 70, 74 will essentially be in contact with a selected surface region in the diaphragm, with accelerometer 72 in an appropriate motion-sensing relationship relative to, and effectively in contact with, the diaphragm. The lead structure 66 includes conductors (not illustrated in specific detail) which are appropriately connected to the electrodes 70, 74, and to the accelerometer 72, which conductors extend in the lead structure to the second component assembly 64.

The second component assembly 64 includes all of the device electrical circuitry, the device battery, and the device radio and antenna (not specifically pictured in FIG. 8A), such as those, same elements illustrated in FIG. 5. The second component assembly 64 may also include an electrode, which may be formed on the surface of the assembly, or integrated into the assembly. The length of the lead structure 66 is a matter of user choice, and will typically be chosen, of course, to accommodate intended implantation disposition of distributed PIDS device 60 within a particular subject's anatomy.

While the PIDS device 60 of FIG. 8A may be configured with a bi-modal electrode structure for sensing and stimulation, the distributed arrangement of this form of the PIDS device provides electrode spacing that allows for each of a unipolar sensing electrode arrangement and a bipolar stimulating electrode arrangement. For example, a unipolar electrode arrangement may be formed by a first electrode that is one of the electrodes 70, 74 of the lead, and a second electrode that is associated with the component assembly 64. A separate bipolar electrode arrangement may be formed by a first electrode that is one of the electrodes 70, 74 of the lead, and a second electrode that is the other of the electrodes 70, 74 on the lead.

Focusing now on FIGS. 9A and 9B, and beginning with what is shown in FIG. 9A, here, one can see that the distributed PIDS device 60, as was true for the illustration provided in FIG. 6A for the self-contained PIDS device 20, is disposed at previously mentioned implantation position 48 on also previously mentioned inferior diaphragmatic surface region 50a. One will note that only, within distributed PIDS device 60, the first component assembly 62 is shown in FIG. 9A, with lead structure 66 broken away, and the second component assembly 64 not specifically pictured. A reason for this is that what is important to note with respect to what is seen in FIG. 9A is the diaphragmatic positioning of first component assembly 62, with one recognizing that implantation of the other end of distributed PIDS device 60, namely, the second component assembly 64, can be located at the user's choice, and suitably, anywhere in the subject's anatomy below diaphragm 50. While the first component assembly 62 of the PID device 60 is shown in FIG. 9A in a left-lateral location, the first component assembly 62 may also be placed in a right-lateral location. In relation to what is seen in FIG. 9A, the first component assembly 62 may be implanted on the inferior side of the diaphragm 50 by accessing the abdominal cavity through conventional laparoscopy. Placement of the second component assembly 64 (not shown in FIG. 6A) may also be done through conventional laparoscopy.

FIG. 9B, which, as has already been mentioned, is very similar to FIG. 6B, shows the distributed PIDS device 60 disposed at previously mentioned implantation position 56 on also previously mentioned diaphragmatic surface region 50b, located on the superior side of diaphragm 50. In FIG. 9B, the first component assembly 62 has been placed on the superior surface of diaphragm 50 at an implantation position generally shown at 56, which has a left-lateral disposition in the subject's anatomy similar to the left-lateral implantation disposition pictured on the underside of diaphragm 50 in FIG. 9A. The first component assembly 62 may also be placed medially or right-laterally. The first component assembly 62 may be implanted through conventional thoracotomy accessing the thoracic cavity at a location near the second component assembly 64, or through a laparoscopic subxiphoid technique to access the thoracic cavity. The installer of distributed PIDS device 60 may choose an appropriate, above-the-diaphragm placement site for the second component assembly 64. For example, as shown in FIG. 9B, the second component assembly 64 may be implanted subcutaneously in a pocket formed within the pectoral region in accordance with standard pacemaker implant procedures. This enables the operator to place standard transvenous leads at a future date without the need to surgically create a new subcutaneous pocket for locating the component assembly. In this case, the lead structure 66 may be implanted by tunneling in an inferior direction parallel to the sternum to access the thoracic cavity via a sub xiphoid laparoscopic technique, or via a thoracotomy performed near the infraclavicular location somewhere between the $3^{rd}$ and $6^{th}$ ribs near a lateral position to connect the first component assembly 62 and the second component assembly 64. Alternatively, the second component assembly 64 may be implanted in the abdominal region.

Regarding the implantation dispositions shown in FIGS. 9A, 9B, for PIDS devices 60 in each of these dispositions the electrodes and the accelerometers are essentially in direct contact with the described and illustrated surface regions in the diaphragm, out of direct contact with the heart. Additionally, in each of the device dispositions, the electrodes of the respective devices are well positioned to detect easily heart-associated electrical activity, and the accelerometers are similarly positioned to detect easily heart sounds, and, of course, diaphragmatic movement/motion.

PIDS Device as Part of Fully Implantable Cardiac Device

Turning now to FIGS. 8B, 9C, 9D, and 9E, there is shown a third form of a fully implantable PIDS device 800 configured to improve the hemodynamic performance of a subject's heart. Focusing attention initially here on FIG. 8B, the third form of a PIDS device 800 is a cardiac device, e.g., pacemaker or defibrillator, having PIDS device functionality incorporated therein. In one configuration, the cardiac device 800 includes an electronics component 802, one or more cardiac leads 804, 806, and a PIDS lead 808. The one or more cardiac leads 804, 806 may support pacemaker functionality, defibrillation functionality, or both. The leads are placed using standard implant techniques via standard access points and unaffected with respect to implant access and technique by the PIDS device. The electronics component 802 includes electrical componentry configured to perform the cardiac functions of the device. The electronics component 802 and PIDS lead 808 may together include the electrical and mechanico-electrical componentry of FIG. 5 needed to perform the PIDS functionality. Some of the PIDS functionality may alternatively be provided by components that implement the cardiac functions. For example, in the case of a pacemaker, one or more of the cardiac leads 804, 806 may sense cardiac electrical activity directly from the heart. Details of the additional componentry for cardiac functionality are not provided herein, but reference is made to U.S. Pat. No. 9,295,852 for examples of such componentry, the disclosure of which is hereby incorporated by reference. In one configuration, the PIDS lead 808 includes the first component assembly 62, referred to below as the PIDS component assembly, and its various parts, as described above with reference to FIG. 8A.

Figure 9C:
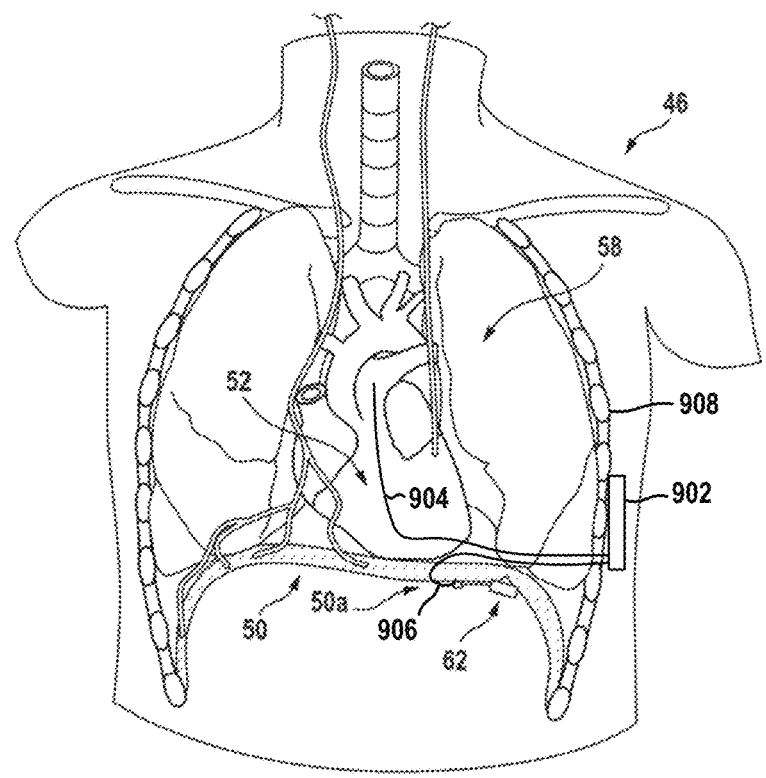
FIGS. 9C, 9D and 9E are similar to FIGS. 6A and 6B, differing in that they illustrate alternative implant locations for the third embodiment of the PIDS device illustrated in FIG. 8B.
Figure 9D:
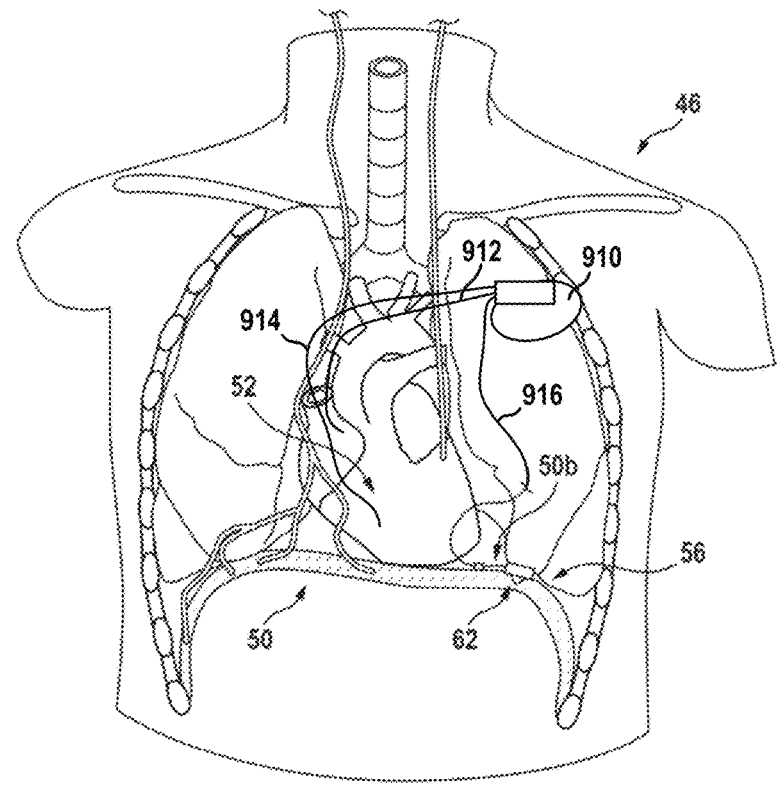

Focusing now on FIGS. 9C and 9D, and beginning with FIG. 9C, an implantable PIDS device in the form of a subcutaneous cardiac defibrillator placed in a lateral position exterior to the thoracic cavity is shown implanted in a patient, with a PIDS component assembly 62 disposed at an inferior diaphragmatic surface region 50a, in a left-lateral location. The subcutaneous cardiac defibrillator includes an electronics component 902 configured to generate defibrillation energy pulses for defibrillating the heart 52 and asymptomatic stimulation pulses for stimulating the diaphragm 50. The electronics component 902 may be implanted at the side of the rib cage 908.

The subcutaneous cardiac defibrillator also includes a defibrillator lead 904 and a PIDS lead 906, each electrically coupled to the electronics component 902. The defibrillator lead 904 is configured to be implanted over the heart 52 and to deliver defibrillation energy pulses. The PIDS lead 906 is configured to be implanted to place the PIDS componentry 62 at a location inferior to the diaphragm 50 thereby remaining extravascular in spirit with the subcutaneous defibrillator. In relation to what is seen in FIG. 9C, the electronics component 902 may be implanted in a subcutaneous space at the side of the rib cage 908 and the defibrillator lead 904 placed over the heart at an exterior thoracic location through a subcutaneous tunnel, such as described in U.S. Pat. No. 8,831,720. The PIDS component assembly 62 portion of the PIDS lead 906 may be implanted on the inferior side of the diaphragm 50 by accessing the abdominal cavity through conventional laparoscopy. The PIDS lead 906 may exit the abdominal cavity and connect to the electronics component 902 through a subcutaneous tunnel. The implanted system including PIDS device, leads, and subcutaneous defibrillator thereby remains wholly extravascular and extra-thoracic.

With reference to FIG. 9D, an implantable PIDS device in the form of a pacemaker/defibrillator is shown implanted in a patient, with a PIDS component assembly 62 disposed at a superior diaphragmatic surface region 50b, in a left-lateral location. The PIDS component assembly 62 may also be placed in a right-lateral location. The pacemaker/defibrillator includes an electronics component 910 configured to generate pacing pulses for pacing the heart 52, defibrillation energy pulses for defibrillating the heart, and asymptomatic stimulation pulses for stimulating the diaphragm 50. The electronics component 910 may be implanted subcutaneously in a surgically created pocket at an infraclavicular pectoral region in accordance with standard pacemaker implant procedures.

The pacemaker/defibrillator also includes a pacing lead 912, a defibrillator lead 914, and a PIDS lead 916, each electrically coupled to the electronics component 910. Each of the pacing lead 912 and the defibrillator lead 914 is configured to be implanted into the heart through the subclavian vein. The pacing lead 912 terminates in the right atrium, while the defibrillator lead 914 extends into the right ventricle. The PIDS lead 906 is configured to be implanted to place the PIDS componentry 62 at a location superior to the diaphragm 50. In relation to what is seen in FIG. 9D, the PIDS component assembly 62 portion of the PIDS lead 916 may be implanted on the superior side of the diaphragm 50 through conventional thoracotomy accessed near the infraclavicular pocket, or through a sub-xiphoid approach by creating a subcutaneous tunnel from the location of the electronics component placement 910 parallel to the sternum until reaching a sub sternal location from where a laparoscopic thoracotomy is performed at a subxiphoid location to reach the superior region of the diaphragm. In either case, extrathoracic tunneling is performed as needed to reach the location of the thoracotomy to access the superior surface of diaphragm 50. In this case, the lead structure 66 may be implanted using a tunneling technique to connect the first component assembly 62 and the second component assembly 64.

Figure 9E:
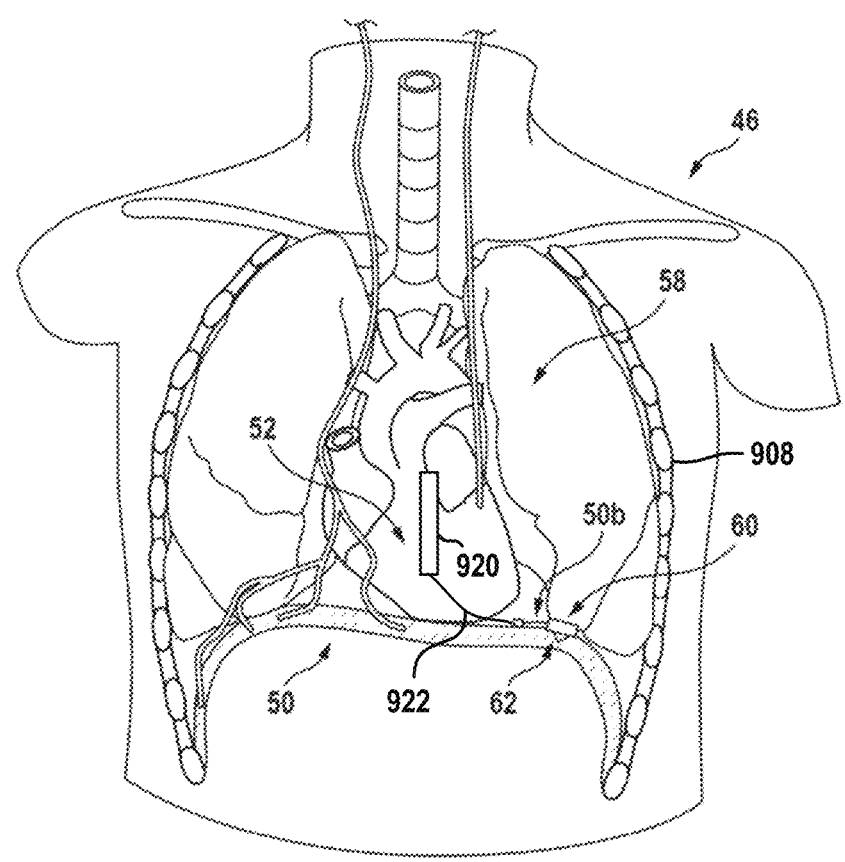

With reference to FIG. 9E, an implantable PIDS device in the form of a subcutaneous cardiac defibrillator placed in a medial position over the heart 52 is shown implanted in a patient, with a PIDS component assembly 62 disposed at a superior diaphragmatic surface region 50b, in a left-lateral location. The subcutaneous cardiac defibrillator includes an electronics component 920 configured to generate defibrillation energy pulses for defibrillating the heart 52 and asymptomatic stimulation pulses for stimulating the diaphragm 50.

The subcutaneous cardiac defibrillator also includes a PIDS lead 922 configured to be implanted to place the PIDS componentry 62 at a location superior to the diaphragm 50 thereby remaining extravascular in spirit with the subcutaneous defibrillator. In relation to what is seen in FIG. 9E, the electronics component 920 may be implanted at a medial, substernal location over the heart 52. The PIDS component assembly 62 portion of the PIDS lead 922 may be implanted on the superior side of the diaphragm 50 by accessing the abdominal cavity through conventional laparoscopy. The PIDS lead 922 may exit the abdominal cavity and connect to the electronics component 920 through a subcutaneous tunnel. The implanted system including PIDS device, leads, and subcutaneous defibrillator thereby remains wholly extra-vascular and extra-thoracic.

Effects of Pacing Induced Diaphragmatic Stimulation

Having now completed descriptions of what is illustrated in FIGS. 6A, 6B, 9A, 9B, reference is now made to FIGS. 7A and 7B. As a reminder, and as was pointed out in the text above regarding the descriptions of the drawings, in each of FIGS. 7A, 7B, device components have been omitted so that one can more easily focus on the motion-created nature of, and behaviors associated with, diaphragmatic electrical stimulation produced by operations of the devices. In each of these two figures, and recognizing that they present enlarged, and very small fragmentary regions drawn from the anatomical presentations seen in FIGS. 6A, 6B and 9A, 9B, the anatomical left side of diaphragm 50 is shown in solid outline in a non-stimulated condition relative to the adjacent anatomical components, and particularly relative to heart 52 and its left ventricle.

As indicated by a downwardly-pointing arrow 80 in FIG. 7A, on the initiation of an electrical stimulating pulse applied to diaphragm 50, the diaphragm moves downwardly rapidly in a caudal direction to a position which is somewhat exaggeratedly illustrated for it in dashed lines at 50A in this figure. This caudal movement of the diaphragm, because of the diaphragm's intimate association with the base of the left ventricle in heart 52, pulls downwardly on this ventricle to produce the position for the lower part of the heart and ventricle shown in dashed lines at 52A in FIG. 7A.

FIG. 7B pictures relevant, moved relationships which exist immediately following the conditions shown in FIG. 7A. More specifically, an upwardly pointing arrow 82 in FIG. 7B shows conditions wherein diaphragm 50 has moved upwardly in a cranial direction to the exaggerated, moved position for it shown in dashed lines at 50B—a diaphragmatic movement which drives upwardly on the underside of the left ventricle in the heart to create a heart and left ventricle moved condition pictured in dashed lines at 52B.

The time-sequential moved conditions pictured in FIGS. 7A, 7B are repeated synchronously in each cardiac cycle of a subject's heart in accordance with predetermined timing, and are triggered by a sensed occurrence of a valid cardiac event. A valid cardiac event may be a valid ventricular event (V-event) or a valid atrial event (A-event).

A valid V-event may be an electrical or mechanical event of a ventricle sensed either electrically by the PIDS device functioning in its sensing mode as established for it by operatively connected electrical circuit structure 32, or mechanically by the accelerometer. In one configuration, a valid electrical V-event may be an intrinsic depolarization of the ventricle that results from normal electrical conduction through the atrioventricular (AV) node. In ECG terminology, such a valid electrical V-event may be a normal R wave, a normal QRS complex, or a normal T wave. In another configuration, a valid electrical V-event may be a ventricular pacing stimulus delivered to the ventricle and sensed by the PIDS device. In yet another configuration, a valid electrical V-event may be an evoked response of the ventricle sensed by the PIDS device. In this regard, an evoked ventricular event corresponds to an electrical depolarization of the ventricle that results from the delivery of a ventricular pacing stimulus. Associated with a ventricular depolarization, whether intrinsic or evoked, is a physical contraction of the ventricle. Accordingly, each of an intrinsic ventricular depolarization and an evoked ventricular depolarization may be sensed by a mechanical sensor, e.g., in the form of an S1 heart sound or an S2 heart sound. In some cases, the PIDS device may be programmed to consider what would otherwise be a valid V-event, as a non-valid V-event if that V-event is associated with a non-normal cardiac episode. For example, if the otherwise valid V-event occurs during an episode of ventricular fibrillation or is followed by a premature ventricular contraction, the PIDS device may deem that V-event non-valid for purposes of delivering diaphragmatic stimulation.

A valid A-event may be an electrical event of an atrium, sensed either electrically by the PIDS device functioning in its sensing mode as established for it by operatively connected electrical circuit structure 32, or mechanically by the accelerometer. In one configuration, a valid electrical A-event may be an intrinsic depolarization of the atrium that originates from the sinoatrial (SA) node. In ECG terminology, such a valid electrical A-event may be a normal P wave. In another configuration, a valid electrical A-event may be an atrial pacing stimulus delivered to the atrium and sensed by the PIDS device. In yet another configuration, a valid electrical A-event may be an evoked response of the atrium sensed by the PIDS device. In this regard, an evoked atrial event corresponds to an electrical depolarization of the atrium that results from the delivery of an atrial pacing stimulus. Associated with atrial depolarization, whether intrinsic or evoked, is a physical contraction of the atrium. Accordingly, each of an intrinsic atrial depolarization and an evoked atrial depolarization may be sensed by a mechanical sensor, e.g., in the form of an S4 heart sound. In some cases, the PIDS device may be programmed to consider what would otherwise be a valid A-event, as a non-valid A-event if that A-event is associated with a non-normal cardiac episode. For example, if the otherwise valid A-event occurs during an episode of atrial tachycardia, atrial fibrillation, or atrial flutter, the PIDS device may deem that A-event non-valid for purposes of delivering diaphragmatic stimulation.

In one configuration, the PIDS device is programmed such that delivery of diaphragm electrical stimulation by the PIDS device is triggered by detections of valid cardiac events. However, while functioning in its sensing mode, the PIDS device may sense and detect cardiac events that are not valid. For example, in the case where diaphragmatic stimulation is triggered by valid V-events, in what may be referred to as a non-normal cardiac cycle an electrical V-event which looks like, but is not a valid electrical V-event, may occur during that cardiac cycle's associated ventricular refractory period. The occurrence of such a non-valid electrical V-event within a cardiac cycle's ventricular refractory period creates a situation where, in order to protect against lack of efficiency and potential difficulty, the PIDS device withholds delivery of diaphragmatic electrical stimulation during that cardiac cycle. In this case, despite the detection of a valid V-event, the PIDS device is programmed to withhold delivery of diaphragm electrical stimulation triggered by the valid V-event due to the detection of an intervening non-valid V-event, wherein intervening in this sense means within the period of time between triggering event and the scheduled time of delivery of diaphragm electrical stimulation. In other cases, the PIDS device may be programmed to ignore the detected intervening non-valid V-event and still deliver diaphragm electrical stimulation at the scheduled time.

Likewise, in the case where diaphragmatic stimulation is triggered by valid A-events, in what may be referred to as a non-normal cardiac cycle an electrical A-event which looks like, but is not a valid electrical A-event, may occur during that cardiac cycle's associated atrial refractory period. The occurrence of such a non-valid electrical A-event within a cardiac cycle's atrial refractory period creates a situation where, in order to protect against lack of efficiency and potential difficulty, the PIDS device withholds delivery of diaphragmatic electrical stimulation during that cardiac cycle. In this case, despite the detection of a valid A-event, the PIDS device is programmed to withhold delivery of diaphragm electrical stimulation triggered by the valid A-event due to the detection of an intervening non-valid A-event. In other cases, the PIDS device may be programmed to ignore the detected intervening non-valid A-event and still deliver diaphragm electrical stimulation at the schedule time.

Diaphragmatic Stimulation Based on V-Events

As noted above, electrical stimulation of the diaphragm may be triggered by sensed ventricular events that are valid ventricular events. A valid sensed ventricular event may be any one of: 1) an intrinsic ventricular event, e.g., an R wave or a Q wave of an electrocardiogram resulting from an intrinsic, naturally conducting ventricular depolarization, 2) a ventricular pacing spike of an electrocardiogram resulting from the delivery of a ventricular pacing stimulus, 3) an evoked ventricular depolarization of an electrocardiogram, which depolarization results from and follows the delivery of a ventricular pacing pulse, or 4) a sensed mechanical event, e.g., an S1 sound resulting from a ventricular contraction, which contraction may result from any one of an intrinsic ventricular depolarization or an evoked ventricular depolarization. In some cases, an otherwise valid sensed ventricular event corresponding to an intrinsic ventricular event or a mechanical ventricular event may be deemed invalid by the PIDS device if the valid sensed ventricular event is associated with a non-normal cardiac episode, such as described above. For example, if the valid V-event is closely followed by a premature ventricular contraction.

Intrinsic V-Events

FIGS. 10A and 10B, illustrate respectively, (a) early, or anticipatory PIDS, and (b) late, or following PIDS, wherein delivery of PIDS stimulations are triggered by sensed intrinsic V-events that are valid. In the description now following the term PIDS may be used in the text (and in the illustrating drawings) to identify diaphragmatic stimulation.

Each figure includes a pair of vertically spaced, horizontal time lines, labeled "V" and "P", where V stands for a V-event, and P stands for PIDS-event. The time lines in these two figures cover four, representative cardiac cycles, and each figure includes a graphical-symbol legend which is associated with the various, graphical indicia that are distributed along the time lines.

Except for the specific discussions now to follow which explain certain predetermined timing settings pictured in these drawings—settings that relate to notable operations of the PIDS device, those who are generally skilled in the relevant art will clearly understand the information conveyed by the related sequences of events pictured in FIGS. 10A and 10B, especially in the context of understanding that operation of the PIDS device involves cardiac-cycle-synchronized sensing of valid V-events, electrical or mechanical, and the using of such sensed and noted events as triggers for the implementation of a then-following, diaphragmatic electrical stimulation.

Continuing with FIGS. 10A and 10B, the upper time line in each of these figures represents a sequential series of sensed V-events, and the lower time line represents respectively associated, thereafter-following PIDS stimulations. Angular, sloping dashed lines which extend in each of FIGS. 10A and 10B downwardly and to the right between the upper and lower time lines relate to what are referred to herein as VP delay periods or VP coupling intervals, and also as predetermined timed relationships—parameters that are functional in the operation of the PIDS device in accordance either with (a) user-selected presetting of these delays, (b) used re-setting of these delays after a period of device operation, and/or (c) on-the-fly, device-internal, systemically self-effected adjustments of such delays, where such device-internal adjustments are permitted (i.e., user-selectively accommodated by appropriately device-included, conventional logic programming).

In embodiments of the PIDS device that are currently contemplated, adjustments in the VP delay period, both in a necessary pre-setting manner with the device in an implanted (or not) condition, and later, if desired, in a device-implanted re-setting situation, are permitted via remote telemetry, or otherwise. The graphically illustrated VP delay periods represented by the sloping, dashed lines in FIGS. 10A and 10B, are actually measureable, i.e. visualizable, graphically in these figures in a manner and direction which is horizontally parallel to the time lines, and not angularly.

Saying a little bit more in an orientation sense regarding FIGS. 10A and 10B, the relational, sensed V-events and associated PIDS stimulations pictured may now be thought of as being presented, for further and discussion illustration purposes herein, in the context of an implementation of the PIDS device wherein it is valid, electrical V-events have been selected to be the markers, i.e., the triggers, for PIDS stimulation.

Continuing with description relating to matters shown graphically in FIGS. 10A and 10B, there are two timing periods that are taken into account in the operation of the PIDS device, one of which, the VP delay period, has just been discussed, and the other of which is the length of the so-called refractory period that exists in each of a subject's cardiac cycles, immediately following a sensed, valid V-event in that cycle. The refractory period corresponds to a time during which the PIDS device may sense ventricular events but considers such sensed V-events to be non-valid and then ignores such events for purposes of PIDS stimulation delivery. Furthermore, the PIDS device may be programmed to respond to ventricular events sensed during the refractory period by withholding delivery of PIDS stimulation for the relevant cardiac cycle. In other words, the PID device may be programmed to treat an otherwise valid V-event that is closely followed by a non-valid V-event, as a non-valid V-event for purposes of diaphragmatic stimulation. In these two figures, the relevant refractory periods are represented graphically by elongate, vertically-thin, horizontal rectangles distributed along the time lines. The graphical legends presented in FIGS. 10A and 10B make clear which illustrated rectangles these are.

Timing operations, with respect to these two time periods are under the control of two, logic-based timers that are realized/implemented, and operated in appropriate timing-tracking manners by the previously-mentioned, included-logic state machine in its association with the electrical-circuitry-included logic, or computer, structure.

The time-period associated with the timer which deals with tracking a cardiac-cycle refractory period, a period which begins immediately following the sensing of a chosen, valid V-event, involves subject-specific data that is pre-known, for example, to a medical practitioner using the PIDS device, and who is familiar with the particular subject to be equipped with the device. For a given subject, and as a precursor typically to implantation, and certainly to activation, of the PIDS device with respect to that subject, two pieces of subject-specific information are relevant to establishing what will be, at least initially, a preset duration for a timed refractory period. Required for this determination are (1) knowledge of the expected likely heart-rate range of the subject, and (2) knowledge regarding the specifically chosen event (electrical in the situation now being discussed) in each of the subject's cardiac cycles which will be treated as the valid V-event from which a measured time will be observed to determine the application of a following, diaphragmatic stimulation. In the description now underway with respect to FIGS. 10A and 10B operation of the PIDS device will be described in the setting of a pre-selection having been made for the detected onset of the electrical R wave in each cardiac cycle being the valid, triggering V-event. A conventional, appropriately programmed, EGC-watching approach may be used herein to detect this onset in relation to ECG electrical information regularly sensed by the device bimodal electrode structure functioning in its sensing mode under the control of the device electrical circuit structure.

Of the two alternative PIDS therapy possibilities contemplated for operation of the PIDS device, in most applications, the so-called early PIDS stimulation is preferable, and it is for this reason that FIG. 10A, has been chosen to illustrate such stimulation. Early PIDS stimulation, and the relevant VP delay period associated with it, lead effectively to a condition for the application of diaphragmatic stimulation at the beginning of a short time interval which lies, in time, as a precursor to the onset of an anticipated V-event in a particular cardiac cycle. In a manner of thinking, therefore, one can imagine that the actual (precursor) time gap existing between such early PIDS stimulation and the shortly following onset of a valid, anticipated, and soon to be next-sensed, valid V-event constitutes a negative time interval in the cardiac cycle where stimulation is to take place. Because of this, and because such stimulation must be measured from an already-having-occurred, sensed valid V-event, the PIDS device performs this measurement beginning from the just previously sensed, valid V-event in the immediately prior cardiac cycle.

Continuing with this thought, and recognizing that proper establishment, for successful systemic operation, in an early-PIDS manner of functioning, of an appropriate VP delay period following the occurrence of the sensed V-event which is employed to trigger stimulation action, it is important to know, and this is done by an averaging technique, just how to anticipate a next-expected valid V-event. To this end, and employing conventional algorithmic programming well-known to those generally skilled in the relevant art, once the PIDS device has begun its operation, and after the first few cardiac cycles associated with that operation, a running average may be performed based upon a number (n) of prior cardiac cycles to assess an average timing expected between successive, valid V-events. The measure of time between successive valid V-events is referred to FIGS. 10A and 10B as a VV interval. For example, in a case where n=4, the average VV interval is made known within the logic componentry in the PIDS device for every successive cardiac cycle after the first four cycles which mark the beginning of device operation. Accordingly, a VP delay period, represented in FIG. 10A by the sloping dashed lines, may be calculated on-the-fly by performing a subtraction from the then-available averaged timing determined between successive, valid V-events, of the brief, precursor interval, the beginning of which is intended to define the moment of triggering of a PIDS stimulation in anticipation of the expected, very shortly following, next-valid, and sensed, V-event.

If desired, the PIDS device may be structured in a conventional manner to allow the making of a change associated with early PIDS stimulation through the making of a change in settings available to the device describing, differently, the short precursor (subtraction anticipatory) interval just discussed.

Continuing with the discussion regarding what is shown in FIG. 10A, this figure illustrates the potential problem-creating possibility of non-valid, errant V-event which occurs, outside of normal cardiac behavior, within a particular cardiac cycle's refractory period. Looking specifically toward the right side of what is shown in FIG. 10A, seen along the upper time line is a presentation of the occurrence of such an errant V-event 1002 which has taken place soon after a sensed valid V-event 1106 and during the illustrated refractory period 1004 of the cardiac cycle 1008. To the right of this indication in the upper time line, and specifically below the associated, lower time line, it is indicated 1012 that there is not to be an immediately-next-following PIDS stimulation at the end of the VP delay 1010—a protective measure, as noted earlier. Thus, the PIDS device may be configured to treat an otherwise valid V-event 1006 as a non-valid V-event when the otherwise valid V-event is closely followed by a non-valid V-event 1002, to thereby withhold diaphragmatic stimulation. In other configurations, the PIDS device may be programmed to still deliver diaphragmatic stimulation, despite the occurrence of the non-valid V-event 1002.

Directing attention now to FIG. 10B, and as a reminder about the nature of the teaching which is evident in this figure, FIG. 10B describes what has been referred to as a late PIDS stimulation situation. This situation is implemented by setting the VP delay period to a very short time, so that diaphragmatic electrical stimulation is delivered shortly following a sensed, valid V-event.

In relation to a final point to mention regarding FIGS. 10A and 10B, small blackened rectangles distributed along the V time lines in these figures mark short, conventionally-system-implemented ventricular blanking periods. The ventricular blanking periods correspond to times during which the sensing function of the PIDS device is temporarily disabled. Disabling the sensing function prevents a delivered PIDS stimulation from being sensed by the PIDS device and misinterpreted as cardiac electrical activity. In the early PIDS situation (FIG. 10A), these blanking periods fall outside of the cardiac-cycle refractory periods. In the late PIDS situation (FIG. 10B), the blanking periods occur during refractory periods.

Turning attention now to FIGS. 11 and 12, FIG. 11 illustrates, along two, vertically spaced, time-related time lines, (1) an upper graphical trace of an ECG waveform received from subject-implanted device electrodes, picturing a large plurality of successive subject cardiac cycles, including the evident presences of cycle-synchronized PIDS stimulations, and (2) a lower graphical trace of related output information received from the implanted-system-included accelerometer showing both the lower-frequency characteristic of normal respiration, and the superimposed, higher-frequency, cardiac-cycle-synchronized, biphasic diaphragmatic motions that have resulted from the PIDS stimulations shown above in the electrically illustrated cardiac cycles. The waveforms of these biphasic diaphragmatic motions, captured and recorded, as they are, for later reporting by the device, are importantly useful for helping a medical professional, in the setting of actually seeing the waveform of what biphasic, diaphragmatic, stimulation-produced motion looks like, to assess both, ultimately, the quality of a subject's hemodynamic performance, and also the quality of enhancement-assistance thereof furnished by the device.

FIG. 12 furnishes an enlarged, and time-stretched, view of fragments of the two traces presented in FIG. 11, selected from the region in FIG. 11 marked by the two, vertical, laterally-spaced dashed lines that mark a display region for FIG. 12 designated 84 in FIG. 11.

What can be seen by looking at these two drawing figures, very clearly, is that each illustrated PIDS stimulation, which is short-term and pulse-like in nature, produces, in the represented subject's diaphragm's movement, a related, cardiac-cycle-synchronized, relatively high frequency, biphasic, caudal-followed-by-cranial movement of the diaphragm. It is this relatively high-frequency, biphasic, diaphragmatic motion, caudal-followed-by-cranial in nature, which, in the context of there being a properly waveform-shaped motion of the diaphragm, enhances a subject's hemodynamic performance through the effective delivery of that diaphragmatic motion to the underside of the heart's left ventricle, as explained earlier.

As was mentioned earlier herein, internal programming, hard-wired and/or algorithmically programmed/programmable, is in many ways completely conventional in nature in terms of specific tasks that are performable during operation of the device. While, as has already been mentioned above, there are certain settings that, preferably, are introduced as initial settings introduced to the circuitry logic structure provided in the device—put there into place by the device user/installer/implanter—there are certain operational features and re-settings which may, over time, be adjusted and/or introduced, either remotely through short-range telemetry accommodated by radio 44, or automatically internally in association with a systemic capability, if such a capability is selectively provided, for the device to self-monitor and self-adjust various aspects of its own activities. With regard to telemetry-implemented operational modifications, as well as potentially internally self-implemented operational modifications, again, those generally skilled in the relevant arts will know how to do this based upon the systemic and methodologic descriptions presented in this text and pictured in the associated drawing figures.

An important and special feature of the device involves the capturing and recording of accelerometer data associated with the nature of actual, stimulation-produced diaphragmatic biphasic movement. This capture and recording, in association with an importantly implemented, and uniquely contemplated, comparison of captured, actual diaphragmatic motion waveforms with a device-stored, carefully chosen, reference waveform, yields reportable information that allows a device user to initiate stimulation adjustments to improve matters. This comparison activity produces device-stored comparison data which is retrievable by telemetry to furnish valuable confirmatory evidence of the viability of the implemented diaphragmatic stimulation respecting the maximizing and achieving of hemodynamic performance.

Before describing a typical operation of the device with respect to a particular subject, let us turn attention to FIG. 13 in the drawings which illustrates, in block/schematic form, both the basic, and a modified, form of the architecture of the methodology of the present device. The "overall" archaeology, as shown in FIG. 13, is illustrated generally at 86. It includes, as steps represented in block form, six different blocks, including block 88 (Sensing), block 90 (Applying), block 92 (Monitoring), block 94 (Comparing), block 96 (Recording), and block 98 (Choosing). Blocks 88-96, are drawn each with a solid-line outline to signify that they describe, effectively, the basic, or core, methodology of the device. Block 98, which is outlined with a dashed line, represents one modified form of the invented methodology. Reading from left to right in FIG. 13, the several blocks there pictured are connected in the order of associated behaviors, with arrow-headed, right-pointing lines connecting these blocks, as shown, to symbolize, the flow of methodologic activity.

The PIDS device thus offers a method for improving the hemodynamic performance of a subject's heart including, from adjacent a selected surface region in the subject's diaphragm which is out of contact with the heart, (1) sensing and noting (Block 88) the presences in the subject's cardiac cycles of a selected one of (a) per-cycle valid electrical cardiac events, e.g., electrical V-events, and (b) per-cycle valid mechanical cardiac events, e.g., mechanical V-events, (2) based upon such sensing, and upon noting each of such selected, V-event presences, applying (Block 90), in a predetermined timed relationship to such a noting, associated, asymptomatic electrical stimulation directly to the diaphragm, preferably at the selected diaphragmatic surface region, for the purpose of triggering biphasic, caudal-followed-by-cranial motion of the diaphragm, (3) following the applying step, monitoring (Block 92) the waveform of resulting diaphragmatic motion, (4) after performing the monitoring step, Comparing (Block 94) the monitored diaphragmatic-motion waveform with a reference, diaphragmatic-motion waveform, and (5) on completion of the comparing step, recording (Block 96) the monitored, diaphragmatic-motion waveform for later review.

The methodology of the PIDS device, in a modified form, further includes (1) choosing (Block 98) the selected diaphragmatic surface region to be on one of (a) the inferior, and (b) the superior, side of the diaphragm, and (2) choosing the selected, per-cycle valid V-event whereby, if it is to be electrical, it is one of (a) the R wave, and (b) the Q wave, and if mechanical, it is the S1 heart sound.

Presenting now a description of typical device preparation, implantation, and operation with respect to a particular, selected subject, this description will be based upon the implantation in a subject of that form of the device which is pictured in FIGS. 1-5, inclusive, and installed as illustrated in FIG. 6A. Further, this description will be based upon a predetermination that the triggering of diaphragmatic stimulation will be based upon the sensing, in the subject's cardiac cycles, of valid electrical V-events, with the chosen, valid electrical V-event being the onset of the R wave. The operational description which now follows will also rest upon a pre-decision that early PIDS stimulation is what is to take place, and that until, as will shortly be described, a more concrete idea is reached for defining an exact VP delay period, the device logic structure—effectively, the state machine portion of this structure—will be told to begin with a VP delay period of zero.

Also initially determined before device implantation, is what kind of a timing interval to pre-assign to the refractory period timer operated by the state machine, and this timing interval will be based upon subject-specific information drawn from pre-knowledge about the subject's expected likely heart-rate range, and typical refractory period time length beginning with the onset of the R wave, and ending with the end of that refractory period. Also predetermined will be device settings that establish, essentially fixedly, the character of electrical PIDS stimulation designed to be clearly asymptomatic in nature.

Much of this pre-implantation information, relevant to preparing the device for best-possible work with the selected subject, will involve a further category of information, known to the appropriate medical personnel, regarding how to assess, with the device operating, maximally-achievable, enhanced hemodynamic performance.

With device pre-settings based upon the just-described preliminary choices made, the device is implanted appropriately, as illustrated in FIG. 6A, and is switched into operation, with the device user immediately collecting appropriate data to assess needed adjustment, from zero, to establish in the state machine the most appropriate early-PIDS time interval now to be reset for per-cycle calculation of the important VP delay period. Those persons skilled in the medical arts will know well how to make this assessment, and with this knowledge in hand, will, through short-range telemetry, introduce into the logical structure of the state machine, as just mentioned, the appropriate VP delay period information.

With the early PIDS, VP delay period thus set, the device now simply regularly estimates, through the on-the-fly averaging technique described above, a proper point in time, following the sensing in one cardiac cycle of a valid electrical V-event, to apply diaphragmatic stimulation in the following cardiac cycle appropriately, and shortly, before the next-sensed, valid electrical V-event. Non-valid, errant electrical V-events sensed during a cardiac cycle's refractory period will not be used to trigger stimulation. Valid electrical V-event sensing will take place through the device-included, bimodal electrode structure placed by the device electrical circuit structure in its sensing mode, and electrical stimulation delivered to the diaphragm, under the controlling influence of the device electrical circuit structure, will be delivered by the same, efficiently employed, bimodal electrode operating in its stimulating mode. Interesting to note here, specifically, is that the incorporation in the device of the described, bimodal electrode structure offers the simplicity of utilizing simply one pair of electrodes to perform, seriatim, electrical-activity sensing, and diaphragmatic electrical stimulation. In another configuration, to be described further below, the electrode structure of the PIDS device may provide for separate electrode arrangements, wherein a first electrode arrangement is used for sensing, and a second electrode arrangement is used for stimulating.

Each sensed, valid electrical V-event will result in asymptomatic electrical stimulation of the subject's diaphragm to produce high-frequency, biphasic, caudal-followed-by-cranial diaphragmatic movement, and this cycle-by-cycle activity will synchronously drive the left ventricle of the subject's heart in a biphasic, pumping-assist manner which will enhance hemodynamic performance as described above.

The device accelerometer will accurately follow the stimulation-induced biphasic diaphragmatic movement which is associated with each diaphragmatic stimulation, and will, cycle-by-cycle, communicate to the electrical circuit structure the mentioned, related, diaphragmatic-motion confirmation signal whose associated waveform will be compared with that of the mentioned, carefully-chosen reference waveform to generate, for storage and later retrieval, cardiac-cycle-by-cardiac-cycle waveform comparison data. All of this activity will be occurring, as mentioned, entirely synchronously with the subject's cardiac-cycle-by-cardiac-cycle heart rate.

The operational description just presented, wherein the preselected, valid V-event has been chosen to be electrical and to be associated specifically with the detected onset of a cardiac cycle R wave, closely also describes both (a) an alternative device operation based upon selection of the Q wave as being the valid electrical V-event, and (b) another, alternative device operation based, instead, on mechanical V-event sensing, wherein a selected, valid mechanical V-event is chosen to be the S1 heart sound—an event which will be sensed by the device-included accelerometer. In this latter, alternative operational setting, the accelerometer plays the dual roles of sensing valid V-events, and tracking and reporting on stimulation-produced diaphragmatic movements.

Ventricular Pacing Stimuli and Evoked V-Events

As describe generally above, the PIDS device may be configured to trigger diaphragmatic electrical simulation based on valid V-events corresponding to ventricular pacing stimuli or evoked ventricular events. FIGS. 14A and 14B, illustrate respectively, (a) early, or anticipatory PIDS, wherein delivery of PIDS stimulations are triggered by ventricular pacing pulses applied to a patient's heart by another device separate and remote from the PIDS device or by another device having PIDS device functionality incorporated therein, and (b) early, or anticipatory PIDS, wherein delivery of PIDS stimulations are triggered by evoked ventricular events, resulting from the application of a pacing pulse to the heart. The other device may be a single chamber or multi-chamber CRM device, such as a pacemaker, or a pacemaker/defibrillator. FIGS. 15A and 15B, illustrate respectively, (a) late, or following PIDS, wherein delivery of PIDS stimulations are trigged by ventricular pacing pulses applied to a patient's heart by another device separate and remote from the PIDS device or by another device having PIDS device functionality incorporated therein, and (b) late, or following PIDS, wherein delivery of PIDS stimulations are trigged by evoked ventricular events, resulting from the application of a pacing pulse to the heart.

Each of these figures includes a pair of vertically spaced, horizontal time lines, labeled "V" and "P", where V stands for a V-event, and P stands for PIDS-event. The time lines in these figures cover four representative cardiac cycles, and each figure includes a graphical-symbol legend which is associated with various graphical indicia that are distributed along the time lines.

The upper time line in each of these figures illustrates a sequential series of V-events, e.g., a ventricular pacing stimuli (V pace) or a ventricular evoked response (V evoked), while the lower time line illustrates PIDS stimulations (P pace) that are triggered by a V-event. Angular, sloping dashed lines which extend downward and to the right between the upper and lower time lines represent VP delay periods or VP coupling intervals. While the VP delay periods are represented by the sloping, dashed lines, the VP periods are measureable graphically in these figures in a manner and direction which is parallel to the time lines, not angularly.

The VP delay periods define the time between a sensed valid V-event and a PIDS stimulation. The VP delay period may initially be programmed in the PIDS device during device implant based on patient-specific information obtained by the implanting physician prior to implant. After initial setting, the VP delay period may be automatically adjusted by the PIDS device itself, based on patient information obtained by the PIDS device. For example, as described further below, the PIDS device may detect a changing heart rate of the patient and adjust the VP delay accordingly.

The PIDS device may be configured to sense one or both of a ventricular pacing pulse or an evoked ventricular event, which trigger delivery of PIDS stimulations. Alternatively, the PIDS device may be coupled with a CRM device through wireless telemetry, so as to receive from the CRM device information corresponding to occurrences of V-events. For example, each time a ventricular pacing pulse is delivered to the heart by the CRM device, the PIDS device may receive an indication of such application, which in turn may trigger delivery of a PIDS stimulation. Also, each time an evoked ventricular event is sensed by the CRM device, the PIDS device may receive an indication of such sensing, which in turn may trigger delivery of a PIDS stimulation. As another example, the CRM device may transmit a current state of pacing parameters, such as a ventricular pacing rate, to the PIDS device. The PIDS device may, in turn, deliver PIDS stimulations based on the current pacing parameters.

As previously mentioned, of the two alternative PIDS possibilities contemplated for operation of the PIDS device, the early PIDS stimulation illustrated in FIGS. 14A and 14B are preferable. Early PIDS stimulation, and the relevant VP delay period associated with it, lead effectively to a condition for the application of diaphragmatic stimulation at the beginning of a short time interval which lies, in time, as a precursor to the onset of an anticipated V-event in a particular cardiac cycle.

In FIG. 14A, early PIDS stimulation is triggered by a ventricular pacing stimuli. In FIG. 14B, early PIDS stimulation is triggered by an evoked ventricular event. In each case, the VP delay period may be based on a VV interval. The VV interval may be the time between successive ventricular pacing stimuli (as shown in FIG. 14A) or the time between successive evoked ventricular events (as shown in FIG. 14B). In either case, the PIDS device may determine the VV interval by: 1) sensing over a number of cardiac cycles, successive ventricular pacing stimuli or successive evoked ventricular events, 2) calculating an VV interval based on the respective times of the sensed successive ventricular pacing stimuli or successive evoked ventricular events, and 3) determining an average of the individual VV intervals. Once the average VV interval is determined, the PIDS device may set the VP delay period so as to deliver PIDS stimulation (P pace) in the short time interval before a next-anticipated V-event.

In the scenario where PIDS stimulation is triggered by ventricular pacing stimuli and the VV interval is based on ventricular pacing stimuli, such as shown in FIG. 14A, the VP delay may be set so as to place the PIDS stimulation (P pace) in the short time interval before an evoked ventricular event (V evoked) that results from the delivery of a ventricular pacing stimuli. A typical time between an application of a ventricular pacing stimuli and a following evoked ventricular event is approximately 10-30 milliseconds. Because of this short time, in this instance the VP delay period may be set to zero so that PIDS stimulation occurs immediately after occurrence of a ventricular pacing stimuli (V pace).

In the scenario where PIDS stimulation is triggered by evoked ventricular events and the VV interval is based on evoked ventricular events, such as shown in FIG. 14B, the VP delay may be set so as to place the PIDS stimulation (P pace) in the short time interval before a next anticipated evoked ventricular event (V evoked). This may be done by setting the VP delay period to a period of time less than the VV interval. For example, the VP delay may be set to a value 20 milliseconds less than the determined VV interval.

With reference to FIGS. 15A and 15B, late PIDS stimulation, and the relevant VP delay period associated with it, lead effectively to a condition for the application of diaphragmatic stimulation at the beginning of a short time interval which lies, in time, just after the onset of a V-event in a particular cardiac cycle. As with the case of early PIDS triggered by intrinsic V-events (as described above with reference to FIG. 10B), the VP delay is set to a very short time, so that diaphragmatic electrical stimulation is delivered shortly following an occurrence of a ventricular pacing stimuli (FIG. 15A) or an occurrence of an evoked ventricular event (FIG. 15B). For example, the VP delay may be set to a value 20 milliseconds.

Diaphragmatic Stimulation Based on A-Events

As noted above, electrical stimulation of the diaphragm may be triggered by sensed atrial events that are valid atrial events. A valid sensed atrial event may include any one of: 1) an intrinsic atrial event, e.g., a P wave of an electrocardiogram resulting from an intrinsic atrial depolarization, 2) an atrial pacing stimulus of an electrocardiogram resulting from the delivery of an atrial pacing pulse, 3) an evoked atrial depolarization of an electrocardiogram, which depolarization results from and follows the delivery of an atrial pacing pulse, or 4) a sensed mechanical event, e.g., an S4 sound resulting from an atrial contraction, which contraction may result from any one of an intrinsic atrial depolarization or an evoked atrial depolarization. In some cases, an otherwise valid sensed atrial event corresponding to an intrinsic atrial event or a mechanical atrial event may be deemed invalid by the PIDS device if the valid sensed atrial event is associated with a non-normal cardiac episode. For example, if the valid A-event is closely followed by a premature atrial contraction the otherwise valid A-event may be considered non-valid.

Intrinsic A-Events

FIGS. 16A and 16B, illustrate respectively, (a) early, or anticipatory PIDS, and (b) late, or following PIDS, wherein delivery of PIDS stimulations are triggered by sensed intrinsic A-events. Each figure includes three vertically spaced, horizontal time lines, labeled "A", "V", and "P", where A stands for an A-event, V stands for a V-event, and P stands for PIDS-event. The time lines in these two figures cover four, representative cardiac cycles, and each figure includes a graphical-symbol legend which is associated with the various, graphical indicia that are distributed along the time lines.

The upper time line in each of FIGS. 16A and 16B represents a sequential series of intrinsic A-events, the middle line represents a sequential series of V-events, and the lower time line represents PIDS stimulations. The A-events may be any one of an intrinsic A-event, an atrial pacing stimuli, or an evoked A-event. Angular, sloping dashed lines which extend in each of FIGS. 16A and 16B downwardly and to the right between the upper and lower time lines relate to what are referred to herein as AP delay periods or AP coupling intervals, and also as predetermined timed relationships. While the AP delay periods are represented by the sloping, dashed lines, the AP periods are measureable graphically in these figures in a manner and direction which is parallel to the time lines, not angularly.

The AP delay periods define the time between a sensed intrinsic A-event and a PIDS stimulation. The AP delay period may initially be programmed in the PIDS device during device implant based on patient-specific information obtained by the implanting physician prior to implant. After initial setting, the AP delay period may be automatically adjusted by the PIDS device itself, based on patient information obtained by the PIDS device. For example, as described further below, the PIDS device may detect a changing heart rate of the patient and adjust the AP delay accordingly.

The PIDS device may be configured to sense one or both of an atrial pacing pulse or an evoked atrial event, which trigger delivery of PIDS stimulations. Alternatively, the PIDS device may be coupled with a cardiac pacing device through wireless telemetry, to thereby receive from the pacing device information corresponding to occurrences of A-events.

Continuing with FIGS. 16A and 16B, there are two timing periods that are taken into account in the operation of the PIDS device, one of which is the previously described AP delay period, and the other of which is the length of an atrial refractory period that exists in each of a subject's cardiac cycles, immediately following a sensed, valid A-event in that cycle. The atrial refractory period corresponds to a time during which the PIDS device may sense atrial events but ignores such events for purposes of PIDS stimulation delivery. More specifically, the PIDS device considers atrial events sensed during the atrial refractory period to be non-valid A-events and responds by withholding delivery of PIDS stimulation for that cardiac cycle.

The atrial refractory period, which begins immediately following the sensing of a valid A-event, may be based on patient-specific data that is known, for example, to the physician overseeing operation of the PIDS device, and who is familiar with the patient in which the PIDS device is or will be implanted. Two pieces of patient-specific information are relevant to establishing an initial value of an atrial refractory period. Required for this determination are (1) knowledge of the expected likely heart-rate range of the subject, and (2) knowledge regarding the specifically chosen event (electrical in the situation now being discussed) in each of the patient's cardiac cycles which will be treated as the valid A-event from which a measured time will be observed to determine the application of a following, diaphragmatic stimulation.

As previously mentioned, of the two alternative PIDS possibilities contemplated for operation of the PIDS device, the early PIDS stimulation illustrated in FIG. 16A is preferable. Early PIDS stimulation, and the relevant AP delay period associated with it, lead effectively to a condition for the application of diaphragmatic stimulation at the beginning of a short time interval which lies, in time, as a precursor to the onset of an anticipated V-event in a particular cardiac cycle.

The AP delay period may be based on an AV interval. The AV interval may be the time between an intrinsic A event and the following V event. The V-event may be either of an intrinsic V-event or a paced V-event. In either case, the PIDS device may determine the AV interval by: 1) sensing over a number (n) of cardiac cycles, an intrinsic A-event and its following V-event, 2) calculating an AV interval based on the respective times of the sensed intrinsic A-event and its following V-event, and 3) determining an average of the individual AV intervals. Once the average AV interval is determined, the PIDS device may set the AP delay period so as to place the diaphragmatic stimulations (P pace) in the short time interval before a V-event. This may be done by setting the AP delay period to a period of time less than the AV interval. For example, the AP delay may be set to a value 20 milliseconds less than the determined AV interval.

Continuing with FIG. 16A, there is illustrated the potential of a non-valid, errant A-event, which occurs outside of normal cardiac behavior, within a particular cardiac cycle's atrial refractory period. An errant A-event is an atrial event that occurs outside of normal cardiac behavior, and may be for example, an atrial event resulting from atrial tachycardia, atrial flutter, atrial fibrillation. Looking specifically toward the right side of FIG. 16A, seen along the upper time line is an occurrence of an errant A-event during a cycle's atrial refractory period. To the right of errant A-event and in the associated, lower time line, is an indication that the PIDS stimulation triggered by the previous intrinsic A event, and to be delivered at the end of the AP period, is withheld.

With reference to FIG. 16B, late PIDS stimulation, and the relevant AP delay period associated with it, lead effectively to a condition for the application of diaphragmatic stimulation at the beginning of a short time interval which lies, in time, just after the onset of an anticipated V-event in a particular cardiac cycle. As with the case of early PIDS, the AP delay is set by first determining an average AV interval for the patient. Once the average AV interval is determined, the PIDS device may set the AP delay period so as to place the diaphragmatic stimulation (P pace) in the short time interval just after a V-event anticipated to follow the triggering intrinsic atrial event. This may be done by setting the AP delay period to a period of time greater than the AV interval. For example, the AP delay may be set to a value 20 milliseconds greater than the determined AV interval.

In relation to a final point to mention regarding FIGS. 16A and 16B, small blackened rectangles distributed along the V time lines in these figures mark short, conventionally-system-implemented ventricular blanking periods. The ventricular blanking periods correspond to times during which the sensing function of the PIDS device is temporarily disabled. Disabling the sensing function prevents a delivered PIDS stimulation from being sensed by the PIDS device and misinterpreted as cardiac electrical activity. In the early PIDS situation, these blanking periods fall outside of the cardiac-cycle refractory periods. In the late PIDS situation, the blanking periods occur during refractory periods.

Atrial Pacing Pulses/Evoked A-Events

FIGS. 17A and 17B, illustrate respectively, (a) early, or anticipatory PIDS, wherein delivery of PIDS stimulations are triggered by atrial pacing pulses applied to a patient's heart by another device separate and remote from the PIDS device or by another device having PIDS device functionality incorporated therein, and (b) early, or anticipatory PIDS, wherein delivery of PIDS stimulations are triggered by evoked atrial events, resulting from the application of a pacing pulse to the heart. The other device may be a single chamber or multi-chamber CRM device, e.g., a pacemaker, or a pacemaker/defibrillator. FIGS. 18A and 18B, illustrate respectively, (a) late, or following PIDS, wherein delivery of PIDS stimulations are trigged by atrial pacing pulses applied to a patient's heart by another device separate and remote from the PIDS device, and (b) late, or following PIDS, wherein delivery of PIDS stimulations are trigged by evoked atrial events, resulting from the application of a pacing pulse to the heart.

Each figure includes three vertically spaced, horizontal time lines, labeled "A", "V", and "P", where A stands for an A-event, V stands for a V-event, and P stands for PIDS-events. The time lines in these two figures cover four, representative cardiac cycles, and each figure includes a graphical-symbol legend which is associated with the various, graphical indicia that are distributed along the time lines.

The upper time line in each of these figures represents a sequential series of A-events, e.g., an atrial pacing pulse (A pace) or an atrial evoked event (A evoked), the middle line represents a sequential series of V-events, and the lower time line represents PIDS stimulations. Angular, sloping dashed lines which extend in each of figures downwardly and to the right between the upper and lower time lines relate to what are referred to herein as AP delay periods or AP coupling intervals, and also as predetermined timed relationships. While the AP delay periods are represented by the sloping, dashed lines, the AP periods are measureable graphically in these figures in a manner and direction which is parallel to the time lines, not angularly.

The AP delay periods define the time between a sensed intrinsic A-event and a PIDS stimulation. The AP delay period may initially be programmed in the PIDS device during device implant based on patient-specific information obtained by the implanting physician prior to implant. After initial setting, the AP delay period may be automatically adjusted by the PIDS device itself, based on patient information obtained by the PIDS device. For example, as described further below, the PIDS device may detect a changing heart rate of the patient and adjust the AP delay accordingly.

The PIDS device may be configured to sense one or both of an atrial pacing pulse or an evoked atrial event, which trigger delivery of PIDS stimulations. Alternatively, the PIDS device may be coupled with a CRM device through wireless telemetry, so as to receive from the CRM device information corresponding to occurrences of A-events. For example, each time an atrial pacing pulse is applied to the heart by the pacing device, the PIDS device may receive an indication of such application, which in turn may trigger delivery of a PIDS stimulation. Also, each time an evoked atrial event is sensed by the pacing device, the PIDS device may receive an indication of such sensing, which in turn may trigger delivery of a PIDS stimulation. As another example, the CRM device may transmit a current state of pacing parameters, such as an atrial pacing rate, to the PIDS device. The PIDS device may, in turn, deliver PIDS stimulations based on the current pacing parameters.

As previously mentioned, of the two alternative PIDS possibilities contemplated for operation of the PIDS device, the early PIDS stimulation illustrated in FIGS. 17A and 17B are preferable. In FIG. 17A, early PIDS stimulation is triggered by atrial pacing stimuli. In FIG. 17B, early PIDS stimulation is triggered by an evoked atrial event. Early PIDS stimulation, and the relevant AP delay period associated with it, lead effectively to a condition for the application of diaphragmatic stimulation (P pace) at the beginning of a short time interval which lies, in time, as a precursor to the onset of a V-event anticipated to follow the triggering A-event in a particular cardiac cycle.

In each case, the AP delay period may be based on an AV interval. The AV interval may be the time between an atrial pacing stimuli and a following V-event (as shown in FIG. 17A) or the time between an evoked atrial event and a following V-event (as shown in FIG. 17B). The V-event may be either of an intrinsic V-event or a paced V-event. In either case, the PIDS device may determine the AV interval by: 1) sensing over a number of cardiac cycles, an A-event and its following V-event, 2) calculating an AV interval based on the respective times of the sensed A-event and its following V-event, and 3) determining an average of the individual AV intervals. Once the average AV interval is determined, the PIDS device may set the AP delay period so as to place the P pace in the short time interval before a V-event anticipated to follow the triggering atrial pacing stimuli, in a particular cardiac cycle.

In the scenario where PIDS stimulation is triggered by atrial pacing stimuli and the AV interval is based on atrial pacing stimuli, such as shown in FIG. 17A, the AP delay may be set so as to place the PIDS stimulation (P pace) in the short time interval before the next anticipated V-event that follows the atrial pacing stimuli (A pace). This may be done by setting the AP delay period to a period of time less than the AV interval. For example, the AP delay may be set to a value 20 milliseconds less than the determined AV interval.

In the scenario where PIDS stimulation is triggered by an evoked atrial event and the AV interval is based on evoked atrial events, such as shown in FIG. 17B, the AP delay may be set so as to place the PIDS stimulation (P pace) in the short time interval before a next anticipated V-event that follows the atrial evoked event (A pace). This may be done by setting the AP delay period to a period of time less than the AV interval. For example, the AP delay may be set to a value 20 milliseconds less than the determined AV interval.

With reference to FIGS. 18A and 18B, late PIDS stimulation, and the relevant AP delay period associated with it, lead effectively to a condition for the application of diaphragmatic stimulation at the beginning of a short time interval which lies, in time, just after the onset of an anticipated V-event in a particular cardiac cycle. As with the case of early PIDS, the AP delay is set by first determining an average AV interval for the patient. Once the average AV interval is determined, the PIDS device may set the AP delay period so as to place the P pace in the short time interval just after a V-event anticipated to follow the triggering A-event.

In the scenario where PIDS stimulation is triggered by atrial pacing stimuli and the AV interval is based on atrial pacing stimuli, such as shown in FIG. 18A, the AP delay may be set so as to place the PIDS stimulation (P pace) in the short time interval just after the V-event that follows the atrial pacing stimuli (A pace). This may be done by setting the AP delay period to a period of time greater than the AV interval. For example, the AP delay may be set to a value 20 milliseconds greater than the determined AV interval.

In the scenario where PIDS stimulation is triggered by evoked atrial events and the AV interval is based on evoked atrial events, such as shown in FIG. 18B, the AP delay may be set so as to place the PIDS stimulation (P pace) in the short time interval just after the V-event that follows the atrial evoked event (A evoked). This may be done by setting the AP delay period to a period of time greater than the AV interval. For example, the AP delay may be set to a value 20 milliseconds greater than the determined AV interval.

Diaphragmatic Stimulation Therapy

Figure 19A:
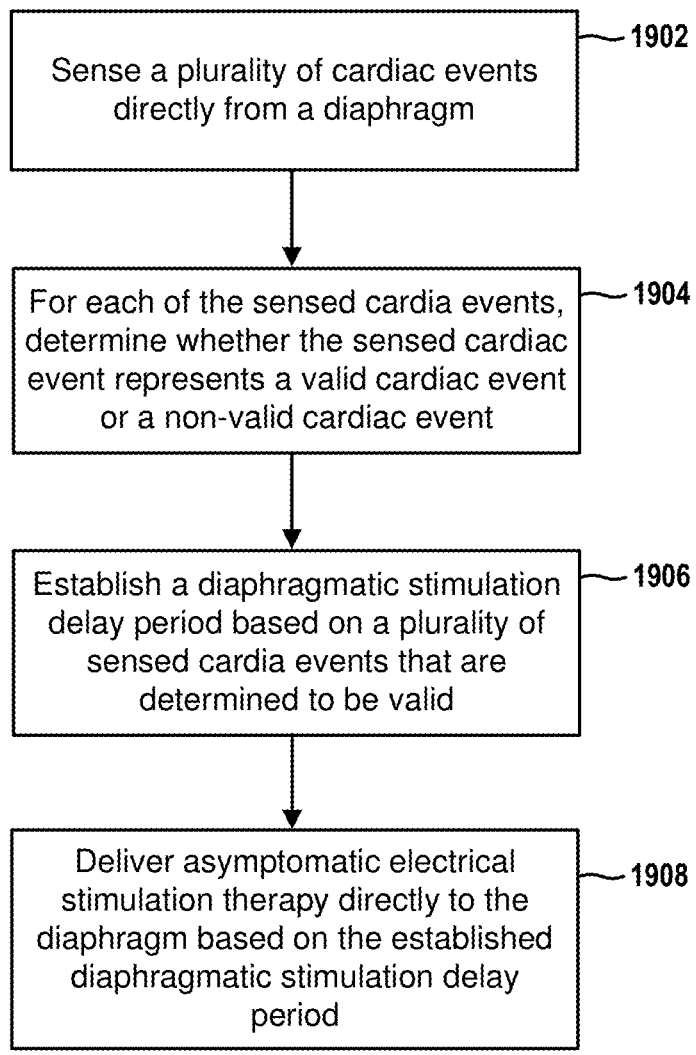

FIG. 19A is a flowchart of a method of improving hemodynamic performance of a heart. The method may be implemented by a PIDS device, configured as shown and described with reference to FIGS. 1-5, 8A, and 8B, implanted in a patient so as to provide for the sensing of cardiac activity, either directly from the patient's diaphragm or directly from the patient's heart, and delivery of electrical stimulation directly to the patient's diaphragm. For example, the PIDS device may be implanted in a patient in locations that allow for direct sensing and stimulation from and to the diaphragm, as described above with reference to FIGS. 6A, 6B, 9A, and 9B. Alternatively, the PIDS device may be implanted in a patient in locations that allows for direct sensing of cardiac activity from the heart, and direct stimulation to the diaphragm, as described above with reference to FIG. 9D.

At block 1902 of FIG. 19A, the PIDS devices senses a plurality of cardiac events directly from a diaphragm. To this end, electrical signals corresponding to cardiac events may be sensed through an electrode arrangement formed by at least two electrodes of the PIDS device. In one implementation, a unipolar electrode arrangement may be used to sense electrical cardiac events. For example, with reference to FIGS. 8A and 8B, a unipolar electrode arrangement may be formed between an electrode on the component assembly 64 of the PIDS device 60 and an electrode 70, 74 that is implanted in or on diaphragm tissue so as to establish a direct contact with the diaphragm. In another implementation, a bipolar electrode arrangement may be used to sense electrical cardiac events. For example, with reference to FIGS. 8A and 8B, a bipolar electrode arrangement may be formed between two electrodes 70, 74 implanted in or on diaphragm tissue so as to establish a direct contact with the diaphragm.

With respect to sensing by a unipolar electrode arrangement, since the component assembly 64 and its associated electrode may be implanted in the region of the diaphragm near or under the rib cage, and the tip, electrode bearing portion of the lead implanted in or on the diaphragm spaced apart from the can assembly, it is possible to have a unipolar electrode arrangement with sufficiently spaced apart electrodes that allows for the sensing of electrical cardiac activity from either of the ventricle and the atrium. To this end, the circuitry of the PIDS device may include a sensing filter that receives signals from the unipolar electrode arrangement. The sensing filter may be tuned to detect ventricular events, including either of intrinsic V-events (R waves), ventricular pacing stimuli, or evoked V-events. For example, the sensing filter may be tuned to detect R waves in the 70-200 Hz range Alternatively, the sensing filter may be tuned to detect atrial events, including either of intrinsic A-events (P waves), atrial pacing stimuli, or evoked A-events. For example, the sensing filter may be tuned to detect P waves in the 25-35 Hz range.

At block 1904 of FIG. 19A, for each of the cardiac events sensed by the sensing electrode arrangement, the PIDS device processes the electrical signals corresponding to the sensed cardiac event to determine whether the sensed cardiac event represents a valid cardiac event or a non-valid cardiac event. For purposes of the method of FIG. 19A, valid cardiac events are subsequently used (next in block 1906) to establish a diaphragmatic stimulation delay period.

Electrical cardiac events sensed by the electrodes of a PIDS device may include one or both of electrical atrial events (A-events) and electrical ventricular events (V-event). A valid electrical V-event may be an intrinsic depolarization of the ventricle that results from normal electrical conduction through the atrioventricular (AV) node. In ECG waveform terminology, such a valid electrical V-event may be a normal R wave, a normal QRS complex, or a normal T wave. A valid electrical V-event may be a ventricular pacing stimulus delivered to the ventricle and sensed by the PIDS device. A valid electrical V-event may also be an evoked ventricular event sensed by the PIDS device. In this regard, an evoked ventricular event corresponds to an electrical depolarization of the ventricle that results from the delivery of a ventricular pacing stimulus. In ECG waveform terminology, a ventricular pacing stimulus would appear as a spike, while an evoked ventricular event would appear as a sudden waveform defection very soon after the ventricular spike. In some cases, the PIDS device may be programmed to consider what would otherwise be a valid V-event, as a non-valid V-event if that V-event is associated with a non-normal cardiac episode. For example, if the otherwise valid V-event is followed by a premature ventricular contraction, the PIDS device may deem that V-event non-valid for purposes of establishing a diaphragmatic stimulation delay period.

A valid electrical A-event may be an intrinsic depolarization of the atrium that originates from the sinoatrial (SA) node. In ECG terminology, such a valid electrical A-event may be a normal P wave. In another configuration, a valid electrical A-event may be an atrial pacing stimulus delivered to the atrium and sensed by the PIDS device. A valid electrical A-event may also be an evoked atrial event sensed by the PIDS device. In this regard, an evoked atrial event corresponds to an electrical depolarization of the atrium that results from the delivery of an atrial pacing stimulus. In ECG waveform terminology, an atrial pacing stimulus would appear as a spike, while an evoked atrial event would appear as a sudden waveform defection very soon after the atrial spike. In some cases, the PIDS device may be programmed to consider what would otherwise be a valid A-event, as a non-valid A-event if that A-event is associated with a non-normal cardiac episode. For example, if the otherwise valid A-event is closely followed by a premature atrial contraction, the PIDS device may deem that A-event non-valid for purposes of establishing a diaphragmatic stimulation delay period.

In one configuration, the PIDS device may determine whether the sensed cardiac event represents a valid cardiac event or a non-valid cardiac event based on a morphology analysis. "Morphology" in this context refers to the shape characteristics of a waveform of a sensed cardiac event. A waveform of a sensed cardiac event may be an ECG waveform. Typical morphology characteristics of an ECG waveform include waveform amplitude characteristics and waveform width characteristics. Waveform amplitude characteristics may be, for example, the amplitude of an intrinsic atrial depolarization (a P wave), or the amplitude of an intrinsic ventricular depolarization (a QRS complex or a R wave). Waveform width characteristics may be, for example, the width of a P wave or the width of a QRS complex or R wave.

Further regarding waveform morphology analysis, the PIDS device may process a waveform of an entire cardiac cycle—as opposed to just a cardiac event within the cardiac cycle. Specifically, a waveform of an entire typical cardiac cycle includes a P wave event, a QRS complex event, and a T wave event, up until the following P wave event, wherein each of these individual events is considered a cardiac event. In this case, the morphology characteristics of the ECG waveform further include waveform interval characteristics. Examples of waveform interval characteristics include the time between the beginning of atrial depolarization and the beginning of ventricular depolarization (a PQ interval), or the time between the onset of ventricular depolarization and the end of ventricular repolarization (a QT interval).

The PIDS device may analyze the morphology of a sensed cardiac event by comparing a present characteristic of a waveform, e.g., waveform amplitude or waveform interval, of the sensed cardiac event to a baseline characteristic of a waveform of a valid cardiac event. The PIDS device determines that a sensed cardiac event is a non-valid cardiac event when the comparison outcome fails to satisfy a morphology criterion. The morphology criterion may correspond to an acceptable percentage difference between the waveform characteristic, e.g. amplitude or interval, of the sensed cardiac event and a corresponding baseline waveform characteristic. In this case, the criterion may be considered satisfied and the sensed cardiac event valid, when the percentage difference between the waveform characteristic, of the sensed cardiac event and the baseline waveform characteristic is less than the acceptable percentage. Alternatively, the morphology criterion may correspond to a baseline waveform-characteristic range. In this case, the criterion may be considered satisfied and the sensed cardiac event valid, when the waveform characteristic of the sensed cardiac event is within the baseline waveform-characteristic range. The baseline waveform characteristic and baseline waveform-characteristic ranges are maintained in the PIDS device and may be updated periodically.

In another configuration, the PIDS device may determine whether the sensed cardiac event represents a valid cardiac event or a non-valid cardiac event based on a rhythm analysis. "Rhythm" in this context may refer to the timing of a sensed cardiac event relative to a prior sensed cardiac event of the same type, or the sequence of cardiac events within an entire cardiac cycle.

Regarding timing analysis, also referred to herein as rate analysis, the PIDS device may analyze the rhythm associated with a sensed cardiac event by comparing a present timing between the sensed cardiac event and a prior sensed cardiac event of the same type, to a baseline timing between successive baseline valid cardiac events. The present timing may correspond to a present heart rate, while the baseline timing may correspond to a baseline heart rate or heart rate range. The PIDS device then determines that a sensed cardiac event is a non-valid cardiac event when the present timing fails to satisfy a timing criterion or rate criterion. The rate criterion may correspond to an acceptable percentage difference between the timing between sensed cardiac events, e.g., the present heart rate, and a baseline heart rate. In this case, the criterion may be considered satisfied and the sensed cardiac event valid, when the percentage difference between the present hear rate and the baseline rate is less than the acceptable percentage. Alternatively, the rate criterion may correspond to a baseline heart rate range. In this case, the criterion may be considered satisfied and the sensed cardiac event valid, when the present heart rate is within the baseline heart rate range. The baseline heart rate and baseline heart rate ranges are maintained in the PIDS device and may be updated periodically. In an example of a percentage based criterion, a sensed cardiac event that establishes a current heart rate that deviates from the baseline heart rate by at least 20% may be considered a non-valid cardiac event. Considering a case where the PIDS device has previously determined a baseline timing between successive R waves to be 1 second, i.e., a baseline heart rate of 60 bpm, if the PIDS device senses a next R wave 0.5 seconds after the sensing of a prior R wave, i.e., a sensed heart rate of 120 bpm, the PIDS device may conclude that the next R wave is a non-valid cardiac event since the sensed heart rate deviates from the baseline heart rate by more that 20%. For example, the R wave may be the result of a premature ventricular contraction.

With respect to sequence analysis, the PIDS device may process a waveform of an entire cardiac cycle including the sensed cardiac event, to determine if the sensed cardiac event appears in a proper sequence of cardiac events. For example, in the case of a sensed cardiac event corresponding to a QRS complex wave, the PIDS device may process the entire cardiac cycle that includes the sensed QRS complex wave to determine the sequence of events within the entire cardiac cycle. The entire cardiac cycle may span between the P wave that precedes the sensed QRS complex wave to the T wave that follows the sensed QRS complex wave. If the sequence of events within the entire cardiac cycle consists of PQRST events, with the sensed R wave of the QRS complex wave being immediately preceded by a P wave, the PIDS device may conclude that the sensed R wave is a valid R wave. In this case, a proper PR sequence is present. However, if the sensed R wave of the QRS complex wave is immediately preceded by another R wave, the PIDS device may conclude that the sensed R wave is a non-valid R wave. In this case, an improper RR sequence is present. The RR sequence may be the result of a premature ventricular contraction.

Returning to FIG. 19A, at block 1906, the PIDS device establishes a diaphragmatic stimulation delay period based on a number of sensed cardia events that are determined to be valid. To this end, the PIDS device determines a number of measures of time. Each of the measures of time is a measure of time between a pair of successive sensed cardia events that are determined to be valid.

In one implementation, the pair of successive sensed cardiac events that are determined to be valid includes a valid atrial event followed by a valid ventricular event. Examples of pairs consisting of a valid atrial event followed by a valid ventricular event are shown in FIGS. 16A, 16B, 17A, 17B, 18A, and 18B. In each of these example, the determined measures of time are referred to as AV intervals.

In another example, the pair of successive cardiac events that are determined to be valid include a first valid ventricular event of a first type followed by a second valid ventricular event of the same type. Examples of pairs consisting of a first valid ventricular event followed by a second valid ventricular event of the same type are shown in FIGS. 10A, 10B, 14A, 14B, 15A, and 15B. In each of these example, the determined measures of time are referred to as VV intervals. The ventricular events of the same type may be one of intrinsic ventricular events (V sense, as shown in FIGS. 10A and 10B), ventricular pacing stimuli events (V pace, as shown in FIGS. 14A and 15A), or evoked ventricular events (V evoked, as shown in FIGS. 14B and 15B).

After determining a number of the same type of measures of time, e.g., AV intervals or VV intervals, the PIDS device sets the diaphragmatic stimulation delay period based on a statistical value of the measures of time. The statistical value may be an average of the number of measures of time. With reference to FIGS. 10A, 14A, 14B, 16A, 17A, 17B, the PIDS device may implement early diaphragmatic stimulation, wherein stimulation (P pace, in the figures) is delivered to the diaphragm in a short time interval before a next anticipated ventricular event. This timing of the diaphragmatic electrical stimulation may be achieved by setting the diaphragmatic stimulation delay period (AP delay period, in the figures) to a value less than the statistical value of the AV intervals.

With reference to FIGS. 10B, 15A, 15B, 16B, 17B, 18B, the PIDS device may implement late diaphragmatic stimulation, wherein stimulation (P pace in the figures) is delivered to the diaphragm in a short time interval after a next anticipated ventricular event. This timing of the diaphragmatic electrical stimulation may be achieved by setting the diaphragmatic stimulation delay period (AP delay period, in the figures) to a value greater than the statistical value of the AV intervals.

Figure 19B:
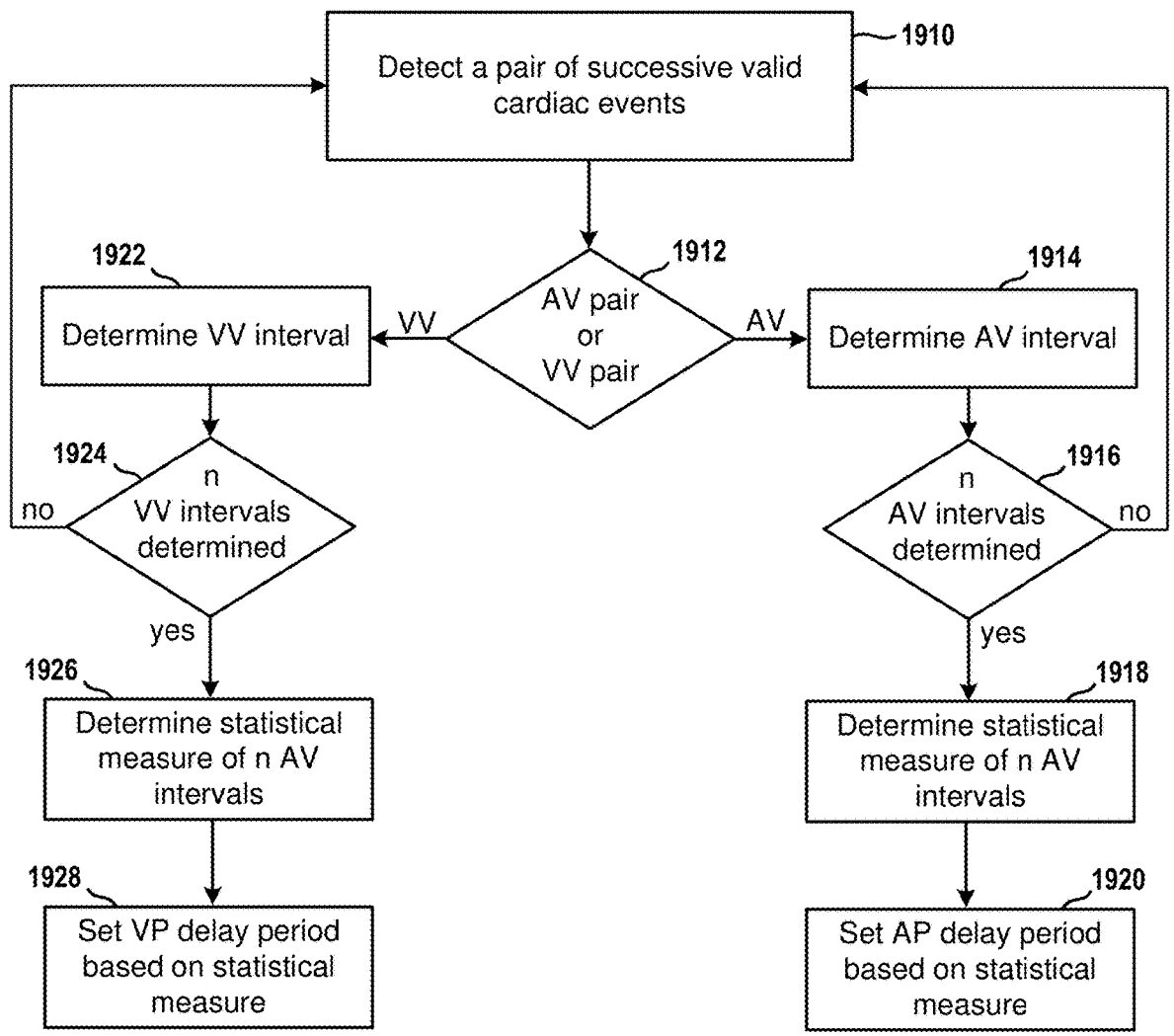

With reference to FIG. 19B, details of a method of establishing a diaphragmatic stimulation delay period based on a number (n) of measures of time is illustrated. The method may be implemented by a PIDS device, configured as shown and described with reference to FIGS. 1-5, 8A, and 8B. At block 1910, the PIDS device detects a pair of successive valid cardiac events. Successive in this regard means that a first valid cardiac event is followed by a second valid cardiac event, without an intervening non-valid cardiac event or occurrence of a non-normal cardiac episode. For example, if a first valid V-event corresponding to a normal R wave is followed by a second valid V-event corresponding to a normal R wave, and there is no detection of a PVC between the first and second valid V-events, then the first and second V-events qualify as a pair of successive valid cardiac events. However, if a PVC is present between the first and second valid V-events, the first and second V-events do not qualify as a pair of successive valid cardiac events.

At block 1912, the PIDS device determines if the pair of successive valid cardiac events corresponds to a valid A-event followed by a valid V-event or a first valid V-event followed by a second valid V-event of the same type. If the pair of successive valid cardiac events is a valid A-event followed by a valid V-event, at block 1914, the PIDS device determines a measure of time, e.g., AV interval, between the pair of valid cardiac events.

At block 1916, the PIDS device determines if a number (n) of AV intervals has been determined. The number (n) may be 1 or any number greater than 1. If a number (n) of AV intervals has not been determined, the process returns to block 1910, where the PIDS device detects another pair of successive valid cardiac events. If a number (n) of AV internals has been determined, then at block 1918, the PIDS device determines a statistical value of the number of AV intervals. At block 1920, the PIDS device sets the AP delay based on the statistical value of AV intervals. The PIDS device may set a first AP delay to achieve early diaphragmatic stimulation, and a second AP delay to achieve late diaphragmatic stimulation. Having each of an early AP delay and a late AP delay provides the PIDS device the flexibility to choose between early and late diaphragmatic stimulation based on patient response.

Returning to block 1912, if the pair of successive valid cardiac events is a first valid V-event followed by a second valid V-event of the same type, at block 1922, the PIDS device determines a measure of time, e.g., VV interval, between the pair of valid cardiac events. At block 1924, the PIDS device determines if a number (n) of VV intervals has been determined. The number (n) may be 1 or any number greater than 1. If a number (n) of VV intervals has not been determined, the process returns to block 1910, where the PIDS device detects another pair of successive valid cardiac events. If a number (n) of VV internals has been determined, then at block 1926, the PIDS device determines a statistical value of the number of VV intervals. At block 1928, the PIDS device sets the VP delay based on the statistical value of VV intervals. Again, the PIDS device may set a first VP delay to achieve early diaphragmatic stimulation, and a second VP delay to achieve late diaphragmatic stimulation.

Returning to FIG. 19A, at block 1908, the PIDS device delivers asymptomatic electrical stimulation therapy directly to the diaphragm based on the established diaphragmatic stimulation delay period. To this end, the PIDS device may be configured or programmed to consider a particular type of cardiac event to be a triggering event, which triggers delivery of stimulation to the diaphragm. For example, the triggering event may be an atrial event or a ventricular event. Upon detection of a triggering event, the PIDS device delivers a stimulation at the end of the established diaphragmatic stimulation delay period, provided the triggering event is a valid cardiac event. To this end, the PIDS device may be configured with a timer that is set to the value of the established diaphragmatic stimulation delay period. At detection of the triggering event, the timer begins to run and upon expiration of the timer, the stimulation is delivered to the diaphragm if the triggering event is a valid cardiac event. If, however, the triggering event turns out to be non-valid, the PIDS device withholds stimulation at expiration of the timer.

In the case of atrial triggered diaphragm stimulation, shown in FIGS. 16A, 16B, 17A, 17B, 18A, and 18B, the PIDS device detects a valid atrial event. To this end, the PIDS device may sense an atrial event, and then determine whether the sensed atrial event is a valid event or a non-valid event. Methodologies for distinguishing between valid and non-valid atrial events are described further below. In response to each detection of a valid atrial event, the PIDS device delivers electrical stimulation at the end of the diaphragmatic stimulation delay period (AP delay period, in the figures) timed relative to the detection of the valid atrial event. Describing this terminology, the diaphragmatic stimulation delay period may be considered to have a start and an end, and the phrase "timed relative to" means the start of the diaphragmatic stimulation delay period may be considered to occur at or soon after detection of the valid atrial event.

In the case of ventricular triggered diaphragm stimulation, shown in FIGS. 10A, 10B, 14A, 14B, 15A, and 15B, the PIDS device detects a valid ventricular event. To this end, the PIDS device may sense a ventricular event, and then determine whether the sensed ventricular event is a valid event or a non-valid event. Methodologies for distinguishing between valid and non-valid ventricular events are described further below. In response to each detection of a valid ventricular event, the PIDS device delivers electrical stimulation at the end of the diaphragmatic stimulation delay period (AP delay period, in the figures) timed relative to the detection of the valid ventricular event. As described above, the diaphragmatic stimulation delay period may be considered to have a start and an end, and the phrase "timed relative to" means the start of the diaphragmatic stimulation delay period may be considered to occur at or soon after detection of the valid ventricular event.

As described above, delivery of asymptomatic electrical stimulation to the diaphragm is triggered by detection of valid cardiac events. Thus, delivery of stimulation to the diaphragm depends on whether a sensed cardiac event corresponding to the triggering event, is valid or non-valid. The PIDS device may be considered to operate in a continuous mode where cardiac events corresponding to the type of triggering cardiac event are continuously sensed for by the PIDS device. For example, if the triggering cardiac event is an atrial event, the PIDS device continuously senses for atrial cardiac events. For each sensed cardiac event corresponding to a triggering event, the PIDS device determines whether the sensed cardiac event represents a valid cardiac event or a non-valid cardiac event.

A sensed cardiac event may be considered a valid cardiac event if the processing of the electrical signal corresponding to the cardiac event determines that the cardiac event is an intrinsic depolarization of the ventricle that results from normal electrical conduction through the atrioventricular (AV) node, or an intrinsic depolarization of the atrium that originates from the sinoatrial (SA) node. In ECG waveform terminology, such a valid electrical V-event may be a normal R wave, a normal QRS complex, or a normal T-wave, and such a valid electrical A-event may be a normal P wave. The sensed cardiac event may also be considered valid if the processing of the signal determines that the cardiac event is a ventricular pacing stimulus delivered to the ventricle, or an evoked ventricular event corresponding to an electrical depolarization of the ventricle that results from the delivery of a ventricular pacing stimulus, or an atrial pacing stimulus delivered to the atrium, or an evoked atrial event corresponds to an electrical depolarization of the atrium that results from the delivery of an atrial pacing stimulus.

In some cases, the PIDS device may be programmed to consider what would otherwise be a valid V-event, as a non-valid V-event if that otherwise valid V-event is associated with a non-normal cardiac episode. For example, if the otherwise valid V-event is followed by a premature ventricular contraction, the PIDS device may deem that V-event non-valid for purposes of establishing a diaphragmatic stimulation delay period. Likewise, the PIDS device may be programmed to consider what would otherwise be a valid A-event, as a non-valid A-event if that otherwise valid A-event is associated with a non-normal cardiac episode. For example, if the otherwise valid A-event is closely followed by a premature atrial contraction, the PIDS device may deem that A-event non-valid for purposes of establishing a diaphragmatic stimulation delay period.

After determining whether the sensed cardiac event is valid or non-valid, the PIDS device delivers asymptomatic electrical stimulation therapy when the sensed cardiac event is a valid cardiac event. If, however, the sensed cardiac event is a non-valid cardiac event, the PIDS device withholds delivery of asymptomatic electrical stimulation therapy at the end of the delay period. The process then repeats for a next sensed cardiac event corresponding to the triggering event. Thus, the PIDS device controls deliver of stimulation on a beat-by-beat basis or on a cardiac cycle basis.

As described above, the PIDS device may be configurable to have unipolar electrode arrangement, formed of a first pair of electrodes, for sensing cardiac electrical activity, and a separate bipolar electrode arrangement, formed of a second pair of electrode different from the first pair, for use delivering diaphragmatic stimulation. Thus, the just described diaphragmatic stimulation may be delivered through a bipolar electrode arrangement. This is advantageous in that the effect of electrical artifact sensed by the unipolar electrode arrangement and resulting from the delivery of stimulation through the bipolar electrode arrangement, would be minimal since the electrodes and associated electronics of the unipolar arrangement or separate from the electrodes of the bipolar arrangement.

Figure 19C:
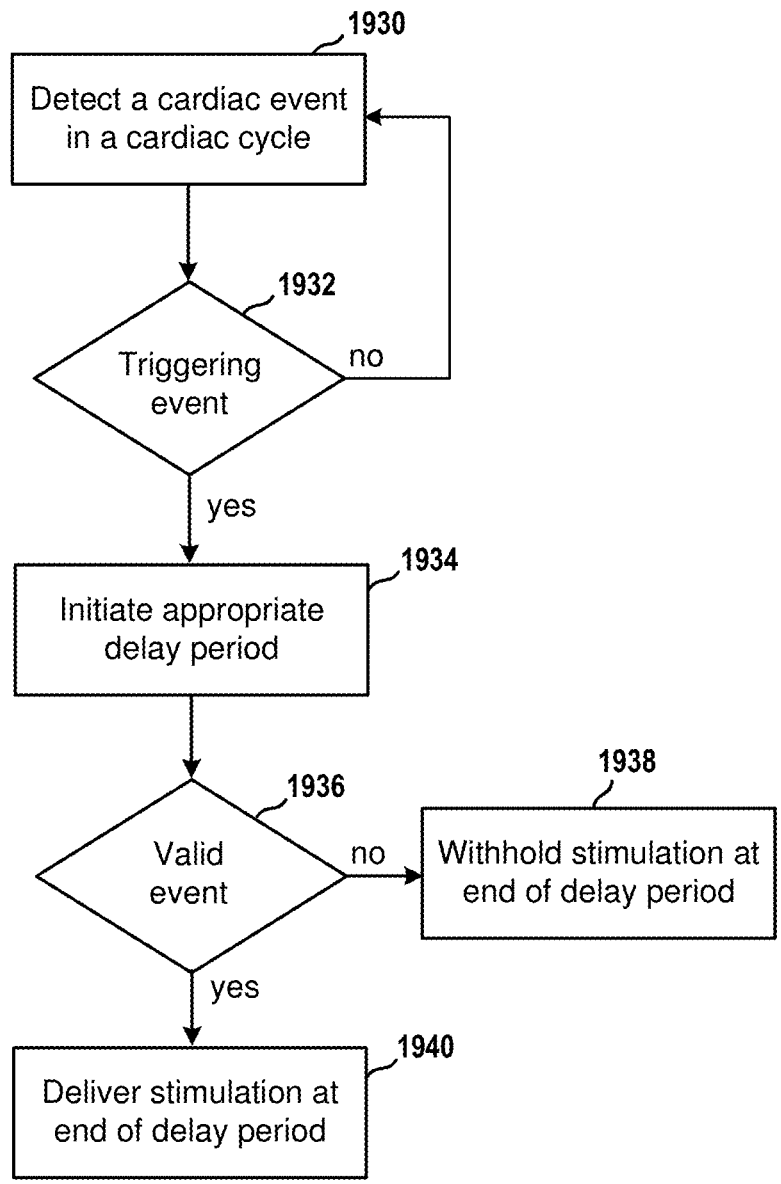

With reference to FIG. 19C, a method of delivering diaphragmatic stimulation on a cardiac-cycle basis is illustrated. The method may be implemented by a PIDS device, configured as shown and described with reference to FIGS. 1-5, 8A, and 8B. At block 1930, the PIDS devices detects a cardiac event in a current cardiac cycle. To this end, the PIDS device may be configured to sense one or both of atrial cardiac events and ventricular cardiac events. At block 1932, the PIDS device determines if the detected cardiac event corresponds to a triggering event, wherein a triggering event corresponds to a type of cardiac event, which if valid, would trigger diaphragmatic stimulation. For example, if the PIDS device is configured to trigger stimulation on a valid atrial event, then a detected atrial event would be triggering event. Likewise, if the PIDS device is configured to trigger stimulation on a valid ventricular event, then a detected ventricular event may be a triggering event. If the PIDS device is configured to trigger on either a valid ventricular event or a valid atrial event, then a detected atrial cardiac event or detected ventricular event would be a triggering event.

If the detected cardiac event does not correspond to a triggering event, the process returns to block 1930. If the detected cardiac event does correspond to a triggering event, the process proceeds to block 1934 where the PIDS device initiates an appropriate delay period based on the triggering event. For example, if the triggering event is an atrial event, then the PIDS device would initiate the AP delay period. If the triggering event is a ventricular event, then the PIDS device would initiate the VP delay period. Initiation of the delay period may be implemented through the start of a timer upon detection of the triggering event.

At block 1936, while the timer is running, the PIDS device determines whether the detected cardiac event corresponding to the triggering event is a valid cardiac event or a non-valid cardiac event. A detected cardiac event may be considered a valid cardiac event if the processing of the electrical signal corresponding to the cardiac event determines that the cardiac event is an intrinsic depolarization of the ventricle that results from normal electrical conduction through the atrioventricular (AV) node, or an intrinsic depolarization of the atrium that originates from the sinoatrial (SA) node. In ECG waveform terminology, such a valid electrical V-event may be a normal R wave, a normal QRS complex, or a normal T wave and such a valid electrical A-event may be a normal P wave. The sensed cardiac event may also be considered valid if the processing of the signal determines that the cardiac event is a ventricular pacing stimulus delivered to the ventricle, or an evoked ventricular event corresponding to an electrical depolarization of the ventricle that results from the delivery of a ventricular pacing stimulus, or an atrial pacing stimulus delivered to the atrium, or an evoked atrial event corresponds to an electrical depolarization of the atrium that results from the delivery of an atrial pacing stimulus.

In some cases, the PIDS device may be programmed to consider what would otherwise be a valid V-event, as a non-valid V-event if that otherwise valid V-event is associated with a non-normal cardiac episode. For example, if the otherwise valid V-event is followed by a premature ventricular contraction, the PIDS device may deem that V-event non-valid for purposes of delivering diaphragmatic stimulation. Likewise, the PIDS device may be programmed to consider what would otherwise be a valid A-event, as a non-valid A-event if that otherwise valid A-event is associated with a non-normal cardiac episode. For example, if the otherwise valid A-event is closely followed by a premature atrial contraction, the PIDS device may deem that A-event non-valid for purposes of delivering diaphragmatic stimulation.

Continuing with block 1936, if the detected cardiac event corresponds to a non-valid cardiac event, the process proceeds to block 1938, where diaphragmatic stimulation is withheld at the end of the delay period. If the detected cardiac event corresponds to a valid cardiac event, the process proceeds to block 1940, where diaphragmatic stimulation is delivered the end of the delay period.

Figure 19D:
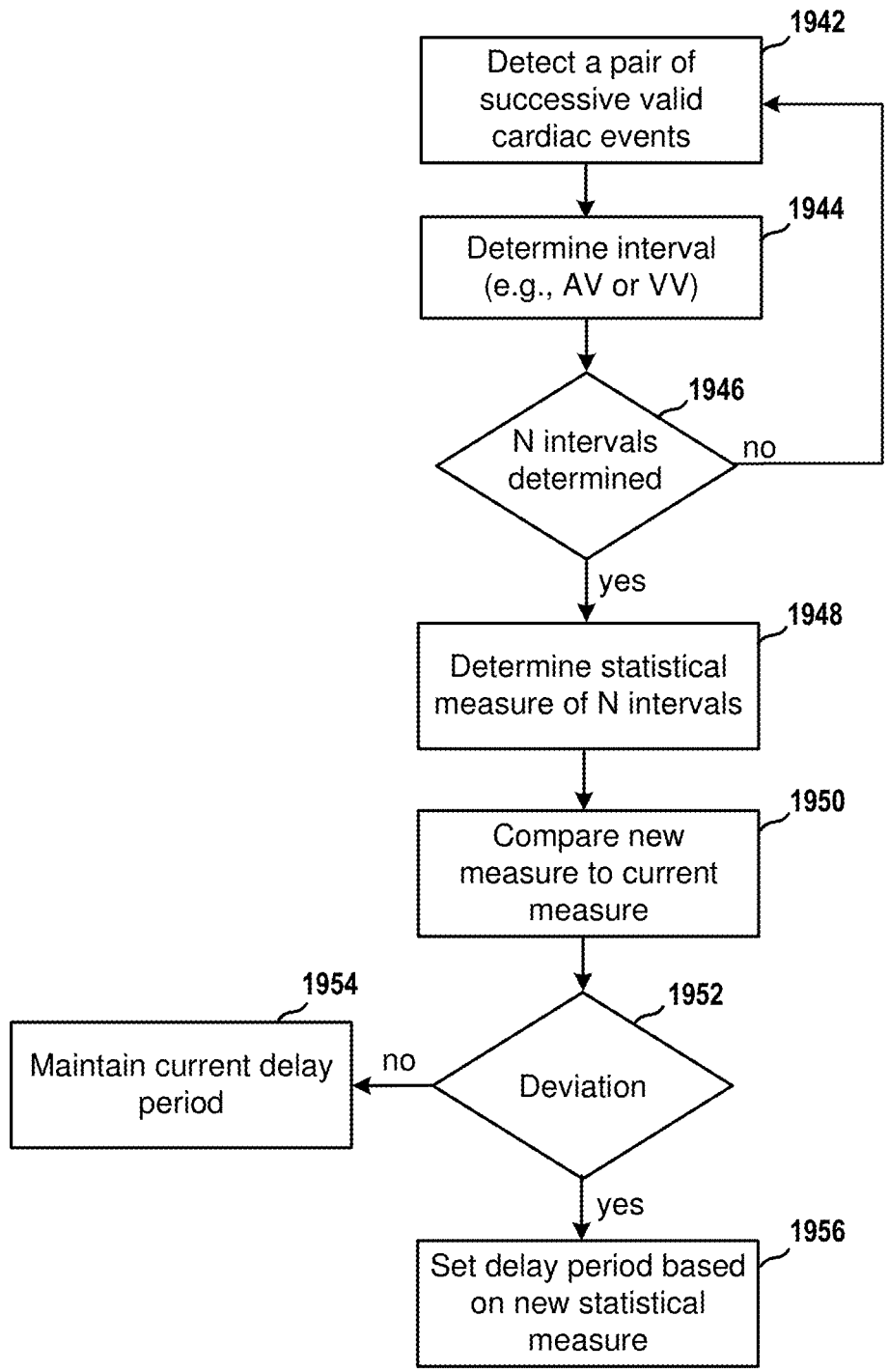

With reference to FIG. 19D, as an additional advantageous feature, the PIDS device may periodically or continuously monitor the timings between pairs of successive cardiac events to detect changes that may warrant an increase or decrease in the diaphragmatic stimulation delay period. Changes in the timings between pairs of successive cardiac events may reflect changes in hemodynamic demand of the patient. For example, during strenuous activity, hemodynamic demand increases. As a result, the patient's heart rate increases and with that, the timings between pairs of successive cardiac events decrease.

In one configuration, the PIDS device implements a method of automatically adjusting the diaphragmatic stimulation delay period to account for changes in hemodynamic demand. The method may be implemented by a PIDS device, configured as shown and described with reference to FIGS. 1-5, 8A, and 8B. To this end, at block 1942 the PIDS device detects a relevant pair of successive valid cardiac events. In the case of a diaphragmatic stimulation delay period corresponding to an AP delay period, the relevant pair of cardiac events would be a valid atrial event and a following valid ventricular event. In the case of a diaphragmatic stimulation delay period corresponding to an VP delay period, the relevant pair of cardiac events would be a first valid ventricular event of a first type and a following second valid ventricular event, also of the first type.

When determining the diaphragmatic stimulation delay period, non-valid cardiac events are excluded from the determining process. Inclusion of non-valid cardiac events in the delay period determination process may result in the delivery of diaphragmatic stimulation at a time that does not benefit hemodynamic performance but rather leads to counterproductive application of intrathoracic pressure changes to the cardiovascular system during the cardiac cycle which may result in reduction in cardiac output and/or increases in left ventricular end-diastolic pressure.

At block 1944, the PIDS device determines the appropriate interval, e.g., AV interval or VV interval, between the pair of successive valid cardiac events. At block 1946, the PIDS device determines if a number (N) of the intervals has been determined. The number (N) may be 1 or any number greater than 1. For example, the number (N) may be between 2 and 10. If a number (N) of intervals has not been determined, the process returns to block 1942, where the PIDS device detects another pair of successive valid cardiac events. If a number (N) of internals has been determined, then at block 1948, the PIDS device determines a new statistical value, e.g., average interval, based on the number of intervals.

At block 1950, the PIDS device compares the new statistical value to the current statistical value that was used to set the current delay period. In order to facilitate the comparison, the PIDS device stores the current statistical value. At block 1952, the PIDS device determines if there is a significant deviation between the new statistical value and the current statistical value. A deviation may be a difference between the two measures, and the deviation may be considered significant if the difference is above a certain threshold. The threshold may be the magnitude of the difference or a percentage based on the difference between the two. The intervals being measured, AV interval or VV interval, are indicative of the heart rate of the patient. Accordingly, a difference between a new statistical value and a current statistical value may be considered to indicate a change in heart rate.

In one configuration, the PIDS device implements a VP delay rate compensation algorithm, wherein the delay period is changed, and the amount of change is a linear and inverse function of a comparison outcome between a current moving average value of VV intervals and a past moving average value. The moving average value is determined based on the following:

$$VVMA = \frac{1}{N}\sum_{i=1}^{N} VV_i$$

where: VV MA=VV interval moving average
N=number of VV intervals, or cardiac cycles
VV=VV interval value In one example, the moving average value is updated each cardiac cycle as a function of changes in moving average values. The VP delay time period is adjusted whenever there is a difference between the current moving average value and the past moving average value, wherein the amount of adjustment depends on a measure (e.g. ratio) of the moving average values. In cases where the current moving average value is greater than the past moving average value, which corresponds to an instance of decreasing heart rate, the VP delay period is increased. For example, if the past VV interval moving average corresponds to a heart rate of 120 bpm, for which the VP delay period is set to 10 milliseconds, and the current moving average corresponds to a heart rate of 60 bpm, the delay rate compensation algorithm will adjust the VP delay period by a factor equal to the inverse of the ratio of the current VV interval moving average to the past VV interval moving average. Thus, the VP delay period would be set to 2 (i.e., the inverse of 60/120) times 10 milliseconds, which equals 20 milliseconds. Conversely, in cases where the current moving average value is less than the past moving average value, which corresponds to an instance of increasing heart rate, the VP delay period is decreased. For example, if the past VV interval moving average corresponds to a heart rate of 60 bpm, for which the VP delay period is set to 20 milliseconds, and the current moving average corresponds to a heart rate of 120 bpm, the delay rate compensation algorithm will adjust the VP delay period by a factor equal to the inverse of the ratio of the current VV interval moving average to the past VV interval moving average. Thus, the VP delay period would be set to ½ (i.e., the inverse of 120/60) times 20 milliseconds, which equals 10 milliseconds.

Continuing with FIG. 19D, if the deviation between the new statistical value and the current statistical value is not significant, the process proceeds to block 1954, where the PIDS device maintains the appropriate delay period at its current setting. If, however, the deviation between the new statistical value and the current statistical value is significant, the PIDS device concludes there is a need for a change in diaphragmatic stimulation delay periods, and the process proceeds to block 1956, where the PIDS device sets the delay period based on the new statistical value of intervals.

As an optional feature, the PIDS device may monitor signals from a motion sensor, e.g., accelerometer, to determine a measure of patient movement activity. The PIDS device may use the measures to confirm a need for changes in diaphragmatic stimulation delay periods.

FIG. 20 is a flowchart of a method of improving hemodynamic performance of a heart. The method may be implemented by a PIDS device, configured as shown and described with reference to FIGS. 1-5, 8A, and 8B, implanted in a patient in manner so as to provide for the sensing of cardiac activity either directly from the patient's diaphragm or directly from the patient's heart, and delivery of electrical stimulation directly to the patient's diaphragm. For example, the PIDS device may be implanted in a patient in locations that allow for direct sensing and stimulation from and to the diaphragm, as described above with reference to FIGS. 6A, 6B, 9A, and 9B.

Alternatively, the PIDS device may be implanted in a patient in locations that allows for direct sensing of cardiac activity from the heart, and direct stimulation to the diaphragm, as described above with reference to FIG. 9D. Implementation of the method by a PIDS device—in and of itself—is referred to as a stand-alone implementation.

The method may also be implemented by an implantable medical system that includes a PIDS device and a separate cardiac rhythm management (CRM) device, e.g., pacemaker. In this system arrangement, the PIDS device and CRM device are configured for real-time communication, with the CRM device configured to sense cardiac activity directly from the heart and transmit indications of sensed cardiac events to the PIDS device. Implementation of the method by a PIDS device together with another device is referred to as a system implementation.

At block 2002 of FIG. 20, the PIDS device determines, from a location associated with a diaphragm, an occurrence of a valid cardiac event. The valid cardiac event may be considered a triggering event for diaphragmatic stimulation. In a stand-alone implementation, the PIDS device may determine an occurrence of a valid cardiac event by first sensing a signal corresponding to the cardiac event, and then processing the signal to determine whether the sensed cardiac event is valid or non-valid. In a system implementation, the PIDS device may determine an occurrence of a valid cardiac event by receiving information from the other implanted medical device that indicates that the cardiac event is valid.

A sensed cardiac event may be considered a valid cardiac event if the processing of the electrical signal corresponding to the cardiac event determines that the cardiac event is an intrinsic depolarization of the ventricle that results from normal electrical conduction through the atrioventricular (AV) node, or an intrinsic depolarization of the atrium that originates from the sinoatrial (SA) node. In ECG waveform terminology, such a valid electrical V-event may be a normal R wave, a normal QRS complex, or a normal T wave and such a valid electrical A-event may be a normal P wave. The sensed cardiac event may also be considered valid if the processing of the signal determines that the cardiac event is a ventricular pacing stimulus delivered to the ventricle, or an evoked ventricular event corresponding to an electrical depolarization of the ventricle that results from the delivery of a ventricular pacing stimulus, or an atrial pacing stimulus delivered to the atrium, or an evoked atrial event corresponds to an electrical depolarization of the atrium that results from the delivery of an atrial pacing stimulus.

In some cases, the PIDS device may be programmed to consider what would otherwise be a valid V-event, as a non-valid V-event if that otherwise valid V-event is associated with a non-normal cardiac episode. For example, if the otherwise valid V-event is followed by a premature ventricular contraction, the PIDS device may deem that V-event non-valid for purposes of delivering diaphragmatic stimulation. Likewise, the PIDS device may be programmed to consider what would otherwise be a valid A-event, as a non-valid A-event if that otherwise valid A-event is associated with a non-normal cardiac episode. For example, if the otherwise valid A-event is associated with a premature atrial contraction, the PIDS device may deem that A-event non-valid for purposes of delivering diaphragmatic stimulation.

At block 2004, the PIDS device delivers asymptomatic electrical stimulation therapy directly to the diaphragm at termination of a delay period that is timed relative to the occurrence of the valid cardiac event. Timed relative, in this context, means that the delay period begins or is initiated upon, or immediately after, the occurrence of the valid cardiac event. For example, the PIDS device may have a timer that is set to the duration of the delay period, and the timer may start to count down upon, or immediately after, the occurrence of the valid cardiac event.

As described in more detail above, a valid cardiac event may be one of a normal intrinsic atrial event, an atrial pacing pulse, an evoked atrial event, a normal intrinsic ventricular event, a ventricular pacing pulse, and an evoked ventricular event, with an additional optional qualification that the cardiac event not be associated with a non-valid cardiac event, e.g., PVC, or a premature atrial contraction. In a stand-alone implementation, the occurrence of a valid cardiac event may be determined through sensing capabilities of the PIDS device. For example, the PIDS device may be configured to sense directly from the diaphragm electrical activity of the heart, including intrinsic atrial events, atrial pacing stimuli delivered to the heart, and evoked atrial events resulting from the delivery of atrial pacing stimuli, intrinsic ventricular events, ventricular pacing stimuli delivered to the heart, and evoked ventricular events resulting from the delivery of atrial pacing stimuli.

Alternatively, in a system implementation, the PIDS device may operate in conjunction with an implanted CRM device, e.g., pacemaker. In this configuration, the PIDS device and CRM device communicate through wireless telemetry, such that the PIDS device receives real-time information from the CRM device. The information may indicate the sensing of an intrinsic cardiac event by the CRM device, the delivery of a pacing pulse by the CRM device, and sensing of an evoked cardiac event by the CRM device.

In one configuration, an occurrence of a valid atrial cardiac event is determined directly by the PIDS device sensing an intrinsic atrial event at the location associated with the diaphragm, and processing the signal corresponding to the sensed intrinsic atrial event to determine whether the intrinsic atrial event is a normal intrinsic atrial event, and preferably one that is not associated with a non-valid atrial event, e.g., a premature atrial contraction. Alternatively, an occurrence of valid atrial cardiac event may be determined indirectly by the PIDS device, through reception of a signal from an implanted CRM device, which signal indicates that a valid intrinsic atrial event has been detected by the implanted CRM device. In either case, the delay period after which diaphragmatic stimulation is delivered by the PIDS device is based on a time between an occurrence of an intrinsic atrial event and an occurrence of a following intrinsic ventricular event. Examples of delay periods, e.g., AP delay periods, based on times between an occurrence of an intrinsic atrial event and an occurrence of a following intrinsic ventricular event, e.g., AV intervals, are shown in FIGS. 16A and 16B.

In another configuration, an occurrence of a valid atrial cardiac event is determined directly by the PIDS device sensing an atrial pacing stimulus at the location associated with the diaphragm, and processing the signal corresponding to the sensed atrial pacing stimulus to confirm that the signal represents a pacing stimulus as opposed to a noise spike or intrinsic atrial activity associated with a premature atrial contraction. Alternatively, an occurrence of valid atrial cardiac event may be determined indirectly by the PIDS device, through reception of a signal from an implanted CRM device, which signal indicates that an atrial pacing stimulus has been delivered by the implanted CRM device. In either case, the delay period after which diaphragmatic stimulation is delivered by the PIDS device is based on a time between an occurrence of an atrial pacing stimulus and an occurrence of a following intrinsic ventricular event. Examples of delay periods, e.g., AP delay periods, based on times between an occurrence of an atrial pacing stimulus and an occurrence of a following intrinsic ventricular event, e.g., AV intervals, are shown in FIGS. 17A and 18A.

In yet another configuration, an occurrence of an atrial cardiac event is determined directly by the PIDS device sensing an atrial evoked response at the location associated with the diaphragm, and processing the signal corresponding to the sensed evoked atrial event to confirm that the signal represents an evoked atrial event as opposed to a noise spike or atrial activity associated with a premature atrial contraction. Alternatively, an occurrence of a valid atrial cardiac event may be determined indirectly by the PIDS device, through reception of a signal from an implanted CRM device, which signal indicates that a valid atrial evoked event has been sensed by the implanted CRM device. In either case, the delay period after which diaphragmatic stimulation is delivered by the PIDS device is based on a time between an occurrence of an evoked atrial event and an occurrence of a following intrinsic ventricular event. Examples of delay periods, e.g., AP delay periods, based on times between an occurrence of an atrial pacing stimulus and an occurrence of a following intrinsic ventricular event, e.g., AV intervals, are shown in FIGS. 17B and 18B.

In one configuration, an occurrence of a ventricular cardiac event is determined directly by the PIDS device sensing an intrinsic ventricular event at the location associated with the diaphragm, and processing the signal corresponding to the sensed intrinsic ventricular event to determine whether the intrinsic ventricular event is a normal intrinsic ventricular event, and preferably one that is not associated with a non-valid ventricular event, e.g., a premature ventricular contraction. Alternatively, an occurrence of a valid ventricular cardiac event may be determined indirectly by the PIDS device, through reception of a signal from an implanted CRM device, which signal indicates that a valid intrinsic ventricular event has been detected by the implanted CRM device. In either case, the delay period after which diaphragmatic stimulation is delivered by the PIDS device is based on a time between an occurrence of an intrinsic ventricular event of a first type, and an occurrence of a following intrinsic ventricular event of the same type. Examples of delay periods, e.g., VP delay periods, based on times between an occurrence of an intrinsic ventricular event of a first type, and an occurrence of a following intrinsic ventricular event of the same type, e.g., VV intervals, are shown in FIGS. 10A and 10B.

In another configuration, an occurrence of a valid ventricular cardiac event is determined directly by the PIDS device sensing ventricular pacing stimulus at the location associated with the diaphragm, and processing the signal corresponding to the sensed ventricular pacing stimulus to confirm that the signal represents a pacing stimulus as opposed to a noise spike or intrinsic ventricular activity associated with a non-valid V-event, e.g., a PVC. Alternatively, an occurrence of a valid ventricular cardiac event may be determined indirectly by the PIDS device, through reception of a signal from an implanted CRM device, which signal indicates that a ventricular pacing stimulus has been delivered by the implanted CRM device. In either case, the delay period after which diaphragmatic stimulation is delivered by the PIDS device is based on a time between an occurrence of a ventricular pacing stimulus and an occurrence of a following ventricular pacing stimulus. Examples of delay periods, e.g., VP delay periods, based on times between an occurrence of a ventricular pacing stimulus and an occurrence of a following ventricular pacing, e.g., VV intervals, are shown in FIGS. 14A and 15A.

In yet another configuration, an occurrence of a ventricular cardiac event is determined directly by the PIDS device sensing an evoked ventricular event at the location associated with the diaphragm, and processing the signal corresponding to the sensed evoked ventricular event to confirm that the signal represents an evoked ventricular event as opposed to a noise spike or ventricular activity associated with a non-valid V-event, e.g., ectopic ventricular tachycardia. Alternatively, an occurrence of ventricular cardiac event may be determined indirectly by the PIDS device, through reception of a signal from an implanted CRM device, which signal indicates that an evoked ventricular event has been sensed by the implanted CRM device. In either case, the delay period after which diaphragmatic stimulation is delivered by the PIDS device is based on a time between an occurrence of an evoked ventricular event and an occurrence of a following evoked ventricular event. Examples of delay periods, e.g., VP delay periods, based on times between an occurrence of an evoked ventricular event and an occurrence of a following evoked ventricular event, e.g., VV intervals, are shown in FIGS. 14B and 15B.

Sensing and Detecting Cardiac Events

Disclosed above are various scenarios for delivering PIDS stimulation based on the detection of various cardiac events, and the distinction of cardiac events as valid or non-valid. While techniques for detecting such cardiac events—and distinguishing between valid and non-valid cardiac events—are known within the field of cardiac rhythm management, through the placement of sensors in, on, or immediately adjacent the heart, techniques for detecting and distinguishing these cardiac events from locations remote from the heart, including in particular, the diaphragm are not known.

As described above, the PIDS device may be configured to sense cardiac events using either of a unipolar sensing arrangement or a bipolar sensing arrangement. A unipolar sensing arrangement is preferred in that it provides for the sensing of atrial cardiac events and ventricular cardiac events. For example, the unipolar sensing arrangement of the PIDS device may allow for the sensing of an electrical A-event that corresponds to one of: an intrinsic depolarization of the atrium (a P wave), a delivery of a pacing stimulus to the atrium (an A pacing spike), or an evoked depolarization of the atrium resulting from a delivery of a pacing stimulus. Likewise, the unipolar sensing arrangement of the PIDS device may allow for the sensing of an electrical V-event that corresponds to one of: an intrinsic depolarization of the ventricle (a R wave), a delivery of a pacing stimulus to the ventricle (a V pacing spike), or an evoked depolarization of the ventricle resulting from a delivery of a pacing stimulus.

Upon sensing a cardiac event, the PIDS device processes the signal corresponding to the sensed cardiac event, possibly together with signals corresponding to the cardiac cycle of which the sensed cardiac event is included in, to determine whether the sensed cardiac event is a valid cardiac event or a non-valid cardiac event. To this end, the PIDS device may process the signal by initially filtering the signal to remove noise, and then comparing one or more of: 1) an amplitude of the sensed cardiac event to a reference amplitude, 2) a timing of the sensed cardiac event relative to other similar sensed cardiac events to a reference timing, and 3) a morphology of a waveform representation of the sensed signal to a reference waveform of normal intrinsically conducted cardiac event. The cardiac signal may be filtered using, for example, a bandpass filter of regular occurrence with high frequencies above 5 Hz.

With respect to amplitude, the PIDS device may determine the amplitude of the sensed cardiac event and compare it to one or more reference amplitudes, each being of a different value and corresponding respectively to one of a pacing stimulus threshold amplitude, an evoked response threshold amplitude, and a normal intrinsic depolarization threshold amplitude. A different set of thresholds would be present for each of ventricular events and atrial events. The PIDS device may compare the amplitude of the sensed cardiac event to each of the threshold amplitudes, to determine if the sensed cardiac event is a valid event, e.g., a pacing stimulus, an evoked event, or a normal intrinsic event, or a non-valid event.

For example, a ventricular pacing spike may be characterized by a first threshold range bound by an upper limit and a lower limit, an evoked ventricular event may be characterized by a second threshold range bound by an upper limit and a lower limit, and a ventricular intrinsic event may be characterized by a third threshold range bound by an upper limit and a lower limit. Assuming there is no overlap between the first threshold range, the second threshold range, and the third threshold range, then the PIDS device would consider a sensed cardiac event having an amplitude within the first threshold range to be a pacing stimulus, a sensed cardiac event having an amplitude within the second threshold range to be an evoked ventricular event, and a sensed cardiac event having an amplitude within the third threshold range to be an intrinsic ventricular event.

In each of these cases, because the amplitude of the sensed cardiac event falls within one of the threshold ranges, the cardiac event may be considered a valid cardiac event. Alternatively, additional criteria may be required to be met before concluding that the event is a valid cardiac event. Such additional criteria may be one or more of the timing based criterion and morphology based criterion described below. If the amplitude of the sensed cardiac event does not fall within a threshold range, the cardiac event may be considered a non-valid cardiac event. Alternatively, additional criteria may be required to be met before concluding that the event is a non-valid cardiac event. Such additional criteria may be one or more of the timing based criterion and morphology based criterion described below.

With respect to timing, in the case of a sensed electrical V-event corresponding to an intrinsic depolarization of the ventricle (a R wave), the PIDS device may determine if the timing of the sensed R wave is too close to a previous sensed R wave such that it occurs during a ventricular refractory period. Likewise, in the case of a sensed electrical A-event corresponding to an intrinsic depolarization of the atrium (a P wave), the PIDS device may determine if the timing of the sensed A wave is too close to a previous sensed A wave such that it occurs during an atrial refractory period. A scenario with respect to ventricular timing is shown in FIG. 10A, wherein a second sensed R wave 1002 occurs during a ventricular refractory period 1004 and is too close to a prior sensed R wave 1006. In this case, the second sensed R wave 1002 may be characterized as a non-valid cardiac event and therapy would be withheld due to the second sensed R wave 1002 being out of acceptable timing range. Also, for purposes of PIDS device operation, the otherwise valid prior sensed R wave 1006 may also be treated as a non-valid event for purposes of diaphragm stimulation because it is part of a cardiac cycle 1008 that includes the non-valid, second sensed R wave 1002. Thus, diaphragm stimulation timed to the prior sensed R wave 1006 is withheld.

In another aspect related to timing, the PIDS device determines whether a current sensed cardiac event is valid or non-valid based on a heart rate criterion. To this end, the PIDS device may determine the heart rate based on a number of sense cardiac events, including the current sensed cardiac event, compare it to the heart rate criterion, and conclude that the current sensed cardiac event is valid if the rate criterion is satisfied and non-valid otherwise. A heart rate criterion may exist for each of atrial cardiac events and ventricular cardiac events. For example, if the current sensed cardiac event being evaluated for validity is an atrial cardiac event, an atrial rate criterion may be considered to be satisfied if a heart rate based on sensed atrial events (including the current sensed atrial cardiac event) is below a certain value indicative of atrial tachycardia. Likewise, if the current sensed cardiac event being evaluated for validity is a ventricular cardiac event, ventricular rate criterion may be considered to be satisfied if the heart rate based on sensed ventricular events (including the current sensed ventricular cardiac event) is below a certain value indicative of ventricular tachycardia. If the heart rate does not to satisfy the criterion, e.g. is greater than the value, the PIDS device concludes that the sensed cardiac event is non-valid.

With respect to morphology, the PIDS device may determine if the morphology of a sensed QRS complex deviates from a baseline morphology of a normal, naturally conducted intrinsic ventricular event. To this end, the PIDS device processes the signal corresponding to the sensed QRS complex by first filtering the signal to remove noise. One or more amplitudes associated with the sensed QRS complex are then compared to corresponding baseline amplitudes. To this end, the QRS complex may be divided into a number of segments of either the same duration or different duration, with each segment having an associated amplitude. Each segment amplitude may be compared to a corresponding amplitude of a similarly segmented baseline QRS complex. Differences, if any, between the various amplitudes of the sensed QRS complex segments and corresponding baseline QRS complex segments are collectively processed to arrive at over measure of similarity between the sensed and baseline QRS complexes. If the similarity measure satisfies a morphology-similarity criterion, the sensed QRS complex is determined to be valid. While the foregoing description has focused on morphology analysis of ventricular events, the PIDS device may be configured to perform a similar analysis with respect to sensed atrial events.

While the foregoing descriptions ways to distinction between valid and non-valid cardiac events has focused on analysis of cardiac electrical activity, e.g., intrinsic events, pacing stimuli, and evoked event, heart sounds may be employed to complement and verify the distinctions. To this end, S1 heart sounds may be processed in parallel with, or in lieu of ventricular electrical activity, to detect an occurrence of a valid V-event. Likewise, S4 heart sounds may be processed in parallel with, or in lieu of ventricular electrical activity, to detect an occurrence of a valid A-event. In one implementation, heart sounds may be used to determine heart rate, prior to any cardiac electrical signal analysis. If the heart rate is indicative of a normal, baseline cardiac rhythm, e.g., heart rate of 60 bpm, the sensed cardiac event is considered a valid event and no further processing for purposes of valid/non-valid distinction is necessary. Alternatively, if the heart rate is indicative of a non-normal cardiac episode, e.g., atrial tachycardia, ventricular tachycardia, etc., the sensed cardiac event is considered a non-valid event and no further processing for purposes of valid/non-valid distinction is necessary.

FIG. 21 is a flowchart of a method performed by a PIDS device to distinguish between valid and non-valid sensed cardiac events. The method may be implemented by a PIDS device, configured as shown and described with reference to FIGS. 1-5, 8A, and 8B. At block 2102, the PIDS device obtains data corresponding to a present sensed cardiac event. The data may be, for example, signal data representative of cardiac electrical activity. For example, the signal data may include data samples from which an ECG waveform may be constructed. The data may also be signals representative of mechanical activity of the heart.

At block 2104, the PIDS device performs an initial rate analysis. To this end, the PIDS device processes the signal data of the present sensed cardiac event, and other sensed cardiac events occurring before and after the present sensed cardiac event to obtain a present heart rate. The PIDS device then determines whether the present heart rate is at or near a baseline, normal, heart rate of the patient. The baseline heart rate may correspond to a normal, at-rest heart rate, e.g., 60 bpm. At block 2106, if the present heart rate is at or near the baseline rate, the process proceeds to block 2108, where the PIDS device concludes that the sensed cardiac event is valid.

At block 2106, if the present heart rate is not at or near the baseline rate, the process proceeds to block 2110, where the PIDS device performs an amplitude analysis of the sensed cardiac event. A detailed description of an amplitude analysis is provided above and is not repeated here. At block 2112, if an amplitude of the sensed cardiac event satisfies an amplitude criterion, e.g., falls within a threshold range corresponding to a valid cardiac event, the process proceeds to block 2108, where the PIDS device concludes that the sensed cardiac event is a valid cardiac event. The amplitude of the sensed cardiac event may be the peak amplitude of the event.

If the amplitude of the sensed cardiac event does not satisfy an amplitude criterion, the process proceeds to block 2114, where the PIDS device performs a timing/rate analysis based on the sensed cardiac event. A detailed description of a timing/rate analysis is provided above and is not repeated here. As part of this timing/rate analysis, the PIDS device may filter the signal corresponding to the sensed cardiac event, and then determine a heart rate based on the sensed cardiac event and other cardiac events. At block 2116, if the determined heart rate determined satisfies a relevant heart rate criterion, the process proceeds to block 2108, where the PIDS device concludes that the sensed cardiac event is a valid cardiac event.

If the determined heart rate does not satisfy a relevant heart rate criterion, the process proceeds to block 2118, where the PIDS device performs a morphology analysis. A detailed description of a morphology analysis is provided above and is not repeated here. As part of the morphology analysis, the PIDS device determines a morphology measure of the sensed cardiac event. At block 2120, if the morphology measure satisfies a relevant morphology criterion, the process proceeds to block 2108, where the PIDS device concludes that the sensed cardiac event is a valid cardiac event. If the morphology measure does not satisfy a relevant morphology criterion, the process proceeds to block 2122, where the PIDS device concludes that the sensed cardiac event is a non-valid cardiac event.

While FIG. 21 and the described method to determine the validity of a sensed cardiac includes various analyses presented in a particular order, not all of the analyses may need to be performed. For example, the PIDS device may be programmed such that, when a particular analysis is not satisfied, e.g., the outcome of the relevant decision block is "no", the device concludes that the sensed cardiac event is non-valid, rather than proceeding to the next analysis. Furthermore, the PIDS device may be programmed to perform the analyses in a different order.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

What is claimed is:

1. An implantable cardiac device comprising:
   a diaphragm lead configured to be implanted on or adjacent a diaphragm;
   one or more cardiac leads configured to be implanted in or on a heart; and
   an electronics component having an electrical circuit structure configured to electrically couple with the diaphragm lead and the one or more cardiac leads, the electrical circuit structure configured to:
      detect a cardiac event in a cardiac cycle based on a signal sensed through the one or more cardiac leads, and
      deliver asymptomatic electrical stimulation therapy to the diaphragm through the diaphragm lead in response to the cardiac event.

2. The implantable cardiac device of claim 1, wherein:
   the one or more cardiac leads comprise a defibrillation lead configured to be implanted over the heart and to deliver defibrillation energy pulses, and
   the electronics component is configured to be implanted subcutaneously and exterior to a thoracic cavity, and to deliver defibrillation energy pulses to the defibrillation lead.

3. The implantable cardiac device of claim 2, wherein:
   the diaphragm lead is configured to be implanted at a location inferior to the diaphragm.

4. The implantable cardiac device of claim 1, wherein:
   the one or more cardiac leads comprise a pacing lead configured to be implanted in the heart and to deliver pacing pulses, and
   the electronics component is configured to be implanted subcutaneously in a surgically created pocket, and to deliver pacing pulses to the pacing lead.

5. The implantable cardiac device of claim 4, wherein:
   the diaphragm lead is configured to be implanted at a location superior to the diaphragm.

6. The implantable cardiac device of claim 1, wherein:
   the one or more cardiac leads comprise a defibrillation lead configured to be implanted in the heart and to deliver defibrillation energy pulses, and
   the electronics component is configured to be implanted subcutaneously in a surgically created pocket, and to deliver defibrillation energy pulses to the defibrillation lead.

7. The implantable cardiac device of claim 6, wherein:
   the diaphragm lead is configured to be implanted at a location superior to the diaphragm.

8. The implantable cardiac device of claim 1, wherein the asymptomatic electrical stimulation therapy is delivered in accordance with a diaphragmatic stimulation delay period.

9. The implantable cardiac device of claim 8, wherein the diaphragmatic stimulation delay period is derived from a plurality of cardiac events that are detected by the electrical circuit structure.

10. The implantable cardiac device of claim 8, wherein the electrical circuit structure is configured to deliver asymptomatic electrical stimulation therapy directly to the diaphragm by being further configured to:
    determine that the detected cardiac event is valid or non-valid;
    in response to a determination that the detected cardiac event is a valid cardiac event, deliver an electrical stimulation pulse at the end of the diaphragmatic stimulation delay period timed relative to the occurrence of the valid cardiac event; and in response to a determination that the detected cardiac event is a non-valid cardiac event, withhold delivery of electrical stimulation at the end of the diaphragmatic stimulation delay period.

11. The implantable cardiac device of claim 1, wherein:
the cardiac event in a cardiac cycle corresponds to an intrinsic ventricular event of an electrocardiogram resulting from an intrinsic, naturally conducting ventricular depolarization.

12. The implantable cardiac device of claim 1, wherein:
the electrical circuit structure is configured to deliver a ventricular pacing pulse through at least one of the one or more cardiac leads, and
the cardiac event in a cardiac cycle corresponds to a ventricular pacing spike of an electrocardiogram resulting from a delivery of a ventricular pacing pulse.

13. The implantable cardiac device of claim 1, wherein:
the electrical circuit structure is configured to deliver a ventricular pacing pulse through at least one of the one or more cardiac leads, and
the cardiac event in a cardiac cycle corresponds to an evoked ventricular depolarization of an electrocardiogram, which depolarization results from and follows a delivery of a ventricular pacing pulse.

14. The implantable cardiac device of claim 1, wherein:
the cardiac event in a cardiac cycle corresponds to an intrinsic atrial event of an electrocardiogram resulting from an intrinsic, naturally conducting atrial depolarization.

15. The implantable cardiac device of claim 1, wherein:
the electrical circuit structure is configured to deliver an atrial pacing pulse through at least one of the one or more cardiac leads, and
the cardiac event in a cardiac cycle corresponds to an atrial pacing spike of an electrocardiogram resulting from a delivery of an atrial pacing pulse.

16. The implantable cardiac device of claim 1, wherein:
the electrical circuit structure is configured to deliver an atrial pacing pulse through at least one of the one or more cardiac leads, and
the cardiac event in a cardiac cycle corresponds to an evoked atrial depolarization of an electrocardiogram, which depolarization results from and follows a delivery of an atrial pacing pulse.

* * * * *